(12) United States Patent
Gong et al.

(10) Patent No.: US 8,114,616 B2
(45) Date of Patent: Feb. 14, 2012

(54) METHODS FOR DIAGNOSING IRRITABLE BOWEL SYNDROME

(75) Inventors: Hua Gong, San Diego, CA (US); Shui Long Wang, San Diego, CA (US); Sharat Singh, Rancho Santa Fe, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 0 days.

(21) Appl. No.: 12/862,707

(22) Filed: Aug. 24, 2010

(65) Prior Publication Data

US 2011/0159521 A1 Jun. 30, 2011

Related U.S. Application Data

(63) Continuation of application No. PCT/US2010/039866, filed on Jun. 24, 2010.

(60) Provisional application No. 61/220,525, filed on Jun. 25, 2009, provisional application No. 61/252,094, filed on Oct. 15, 2009.

(51) Int. Cl.
*G01N 33/53* (2006.01)
*G01N 31/00* (2006.01)

(52) U.S. Cl. ......... 435/7.21; 435/4; 435/7.1; 435/287.9; 436/501; 436/518; 436/525; 436/529; 436/535; 436/809; 427/287; 427/337; 427/338; 530/300; 530/350

(58) Field of Classification Search ..................... None
See application file for complete search history.

(56) References Cited

U.S. PATENT DOCUMENTS

| | | |
|---|---|---|
| 6,867,197 B1 | 3/2005 | Davis et al. |
| 2002/0197661 A1 | 12/2002 | Niles et al. |
| 2008/0057590 A1 | 3/2008 | Urdea et al. |
| 2008/0085524 A1 | 4/2008 | Lois |

OTHER PUBLICATIONS

Barbara, G. et al. "Activated Mast Cells in Proximity to Colonic Nerves Correlate with Abdominal Pain in Irritable Bowel Syndrome," American Gastroenterological Association, 2004, vol. 126, pp. 693-702.

*Primary Examiner* — Lisa Cook
(74) *Attorney, Agent, or Firm* — Kilpatrick Townsend & Stockton LLP

(57) ABSTRACT

The invention provides an ELISA assay for the determination of serum mast cell β-tryptase levels using rabbit anti-tryptase as the capture antibody and alkaline phosphatase conjugated G3 as the detecting antibody. Luminescent substrate CPSD was used to enhance the assay sensitivity. Also provided are methods for aiding in the diagnosis of irritable bowel syndrome by detecting the serum level of β-tryptase, histamine and/or prostaglandin $E_2$.

10 Claims, 13 Drawing Sheets

Optimize the Detecting Ab

Development of Sensitive Human Tryptase ELISA for the Detection of Tryptase in Human Serum

Human tryptase concentration in serum from healthy control (n=156), IBS-D (n=209), IBS-C (n=119), and IBS-A ( n=57)
Values are expressed as mean (SEM), p<0.05 for IBS-D; Mann Whitney U test

METHODS FOR DIAGNOSING IRRITABLE BOWEL SYNDROME

CROSS-REFERENCES TO RELATED APPLICATIONS

This application is a continuation of PCT/US2010/039866, which application claims priority to U.S. Provisional Application No. 61/220,525, filed Jun. 25, 2009 and U.S. Provisional Application No. 61/252,094, filed Oct. 15, 2009, the disclosures of which are herein incorporated by reference in their entirety for all purposes.

BACKGROUND OF THE INVENTION

Irritable bowel syndrome (IBS) is the most common of all gastrointestinal disorders, affecting 10-20% of the general population and accounting for more than 50% of all patients with digestive complaints. However, studies suggest that only about 10% to 50% of those afflicted with IBS actually seek medical attention. Patients with IBS present with disparate symptoms such as, for example, abdominal pain predominantly related to defecation, diarrhea, constipation or alternating diarrhea and constipation, abdominal distention, gas, and excessive mucus in the stool. More than 40% of IBS patients have symptoms so severe that they have to take time off from work, curtail their social life, avoid sexual intercourse, cancel appointments, stop traveling, take medication, and even stay confined to their house for fear of embarrassment. The estimated health care cost of IBS in the United States is $8 billion per year (Talley et al., *Gastroenterol.*, 109:1736-1741 (1995)).

The precise pathophysiology of IBS is not well understood. Nevertheless, there is a heightened sensitivity to visceral pain perception, known as peripheral sensitization. This sensitization involves a reduction in the threshold and an increase in the gain of the transduction processes of primary afferent neurons, attributable to a variety of mediators including monoamines (e.g., catecholamines and indoleamines), substance P, and a variety of cytokines and prostanoids such as E-type prostaglandins (see, e.g., Mayer et al., *Gastroenterol.*, 107:271-293 (1994)). Also implicated in the etiopathology of IBS is intestinal motor dysfunction, which leads to abnormal handling of intraluminal contents and/or gas (see, e.g., Kellow et al., *Gastroenterol.*, 92:1885-1893 (1987); Levitt et al., *Ann. Int. Med.*, 124:422-424 (1996)). Psychological factors may also contribute to IBS symptoms appearing in conjunction with, if not triggered by, disturbances including depression and anxiety (see, e.g., Drossman et al., *Gastroenterol. Int.*, 8:47-90 (1995)).

The causes of IBS are not well understood. The walls of the intestines are lined with layers of muscle that contract and relax as they move food from the stomach through the intestinal tract to the rectum. Normally, these muscles contract and relax in a coordinated rhythm. In IBS patients, these contractions are typically stronger and last longer than normal. As a result, food is forced through the intestines more quickly in some cases causing gas, bloating, and diarrhea. In other cases, the opposite occurs: food passage slows and stools become hard and dry causing constipation.

The precise pathophysiology of IBS remains to be elucidated. While gut dysmotility and altered visceral perception are considered important contributors to symptom pathogenesis (Quigley, Scand. J. Gastroenterol., 38(Suppl. 237):1-8 (2003); Mayer et al., Gastroenterol., 122:2032-2048 (2002)), this condition is now generally viewed as a disorder of the brain-gut axis. Recently, roles for enteric infection and intestinal inflammation have also been proposed. Studies have documented the onset of IBS following bacteriologically confirmed gastroenteritis, while others have provided evidence of low-grade mucosal inflammation (Spiller et al., Gut, 47:804-811 (2000); Dunlop et al., Gastroenterol., 125:1651-1659 (2003); Cumberland et al., Epidemiol. Infect., 130:453-460 (2003)) and immune activation (Gwee et al., Gut, 52:523-526 (2003); Pimentel et al., Am. J. Gastroenterol., 95:3503-3506 (2000)) in IBS. The enteric flora has also been implicated, and a recent study demonstrated the efficacy of the probiotic organism *Bifidobacterium* in treating the disorder through modulation of immune activity (O'Mahony et al., Gastroenterol., 128:541-551 (2005)).

The hypothalamic-pituitary-adrenal axis (HPA) is the core endocrine stress system in humans (De Wied et al., Front. Neuroendocrinol., 14:251-302 (1993)) and provides an important link between the brain and the gut immune system. Activation of the axis takes place in response to both physical and psychological stressors (Dinan, Br. J. Psychiatry, 164:365-371 (1994)), both of which have been implicated in the pathophysiology of IBS (Cumberland et al., Epidemiol. Infect., 130:453-460 (2003)). Patients with IBS have been reported as having an increased rate of sexual and physical abuse in childhood together with higher rates of stressful life events in adulthood (Gaynes et al., Baillieres Clin. Gastroenterol., 13:437-452 (1999)). Such psychosocial trauma or poor cognitive coping strategy profoundly affects symptom severity, daily functioning, and health outcome.

Although the etiology of IBS is not fully characterized, the medical community has developed a consensus definition and criteria, known as the Rome II criteria, to aid in the diagnosis of IBS based upon patient history. The Rome II criteria requires three months of continuous or recurrent abdominal pain or discomfort over a one-year period that is relieved by defecation and/or associated with a change in stool frequency or consistency as well as two or more of the following: altered stool frequency, altered stool form, altered stool passage, passage of mucus, or bloating and abdominal distention. The absence of any structural or biochemical disorders that could be causing the symptoms is also a necessary condition. As a result, the Rome II criteria can be used only when there is a substantial patient history and is reliable only when there is no abnormal intestinal anatomy or metabolic process that would otherwise explain the symptoms. Similarly, the Rome III criteria recently developed by the medical community can be used only when there is presentation of a specific set of symptoms, a detailed patient history, and a physical examination.

It is well documented that diagnosing a patient as having IBS can be challenging due to the similarity in symptoms between IBS and other diseases or disorders. In fact, because the symptoms of IBS are similar or identical to the symptoms of so many other intestinal illnesses, it can take years before a correct diagnosis is made. For example, patients who have inflammatory bowel disease (IBD), but who exhibit mild signs and symptoms such as bloating, diarrhea, constipation, and abdominal pain, may be difficult to distinguish from patients with IBS. As a result, the similarity in symptoms between IBS and IBD renders rapid and accurate diagnosis difficult. The difficulty in differentially diagnosing IBS and IBD hampers early and effective treatment of these diseases. Unfortunately, rapid and accurate diagnostic methods for definitively distinguishing IBS from other intestinal diseases or disorders presenting with similar symptoms are currently not available. The present invention satisfies this need and provides related advantages as well.

BRIEF SUMMARY OF THE INVENTION

The present invention provides methods, assays, systems, and code for accurately classifying whether a sample from an individual is associated with irritable bowel syndrome (IBS). As a non-limiting example, the present invention is useful for classifying a sample from an individual as an IBS sample using a statistical algorithm and/or empirical data. Similarly, the present invention also provides methods, assays, systems, and code for aiding in the diagnosis of irritable bowel syndrome (IBS) in a subject. The present invention is also useful for ruling out one or more diseases or disorders that present with IBS-like symptoms and ruling in IBS using a combination of statistical algorithms and/or empirical data. Thus, the present invention provides an accurate diagnostic prediction of IBS and prognostic information useful for guiding treatment decisions.

In one aspect, the present invention provides a method for aiding in the diagnosis of irritable bowel syndrome (IBS) in a subject, the method comprising: (a) contacting a blood or serum sample from the subject with a β-tryptase binding moiety under conditions suitable to transform β-tryptase present in the sample into a complex comprising β-tryptase and the β-tryptase binding moiety; and (b) determining the level of the complex, thereby determining the level of β-tryptase present in the sample.

In another aspect, the present invention provides a method for aiding in the diagnosis of IBS in a subject, the method comprising: (a) contacting a blood or serum sample from the subject with a histamine binding moiety under conditions suitable to transform histamine present in the sample into a complex comprising histamine and the histamine binding moiety; and (b) determining the level of the complex, thereby determining the level of histamine present in the sample.

In yet another aspect, the present invention provides a method for aiding in the diagnosis of IBS in a subject, the method comprising: (a) contacting a blood or serum sample from the subject with a prostaglandin E2 (PGE2) binding moiety under conditions suitable to transform PGE2 present in the sample into a complex comprising PGE2 and the PGE2 binding moiety; and (b) determining the level of the complex, thereby determining the level of PGE2 present in the sample.

In one aspect, the present invention provides a method for monitoring the progression or regression of irritable bowel syndrome (IBS) in a subject, the method comprising: (a) contacting a first blood or serum sample taken from the subject at a first time with a β-tryptase binding moiety under conditions suitable to transform β-tryptase present in the sample into a complex comprising β-tryptase and the β-tryptase binding moiety; (b) determining the level of the complex, thereby determining the level of β-tryptase present in the first sample; (c) contacting a second blood or serum sample taken from the subject at a second time with a β-tryptase binding moiety under conditions suitable to transform β-tryptase present in the sample into a complex comprising β-tryptase and the β-tryptase binding moiety; (d) determining the level of the complex, thereby determining the level of β-tryptase present in the second sample; and (e) comparing the level of β-tryptase present in the first sample to the level of β-tryptase present in the second sample, wherein a higher level of β-tryptase in the second sample relative to the first sample is indicative of the progression of IBS in the subject and a lower level of β-tryptase in the second sample relative to the first sample is indicative of the regression of IBS in the subject.

In another aspect, the present invention provides a method for monitoring the progression or regression of irritable bowel syndrome (IBS) in a subject, the method comprising: (a) contacting a first blood or serum sample taken from the subject at a first time with a histamine binding moiety under conditions suitable to transform histamine present in the sample into a complex comprising histamine and the histamine binding moiety; (b) determining the level of the complex, thereby determining the level of histamine present in the first sample; (c) contacting a second blood or serum sample taken from the subject at a second time with a histamine binding moiety under conditions suitable to transform histamine present in the sample into a complex comprising histamine and the histamine binding moiety; (d) determining the level of the complex, thereby determining the level of histamine present in the second sample; and (e) comparing the level of histamine present in the first sample to the level of histamine present in the second sample, wherein a higher level of histamine in the second sample relative to the first sample is indicative of the progression of IBS in the subject and a lower level of histamine in the second sample relative to the first sample is indicative of the regression of IBS in the subject.

In yet another aspect, the present invention provides a method for monitoring the progression or regression of irritable bowel syndrome (IBS) in a subject, the method comprising: (a) contacting a first blood or serum sample taken from the subject at a first time with a prostaglandin E2 (PGE2) binding moiety under conditions suitable to transform PGE2 present in the sample into a complex comprising PGE2 and the PGE2 binding moiety; (b) determining the level of the complex, thereby determining the level of PGE2 present in the first sample; (c) contacting a second blood or serum sample taken from the subject at a second time with a PGE2 binding moiety under conditions suitable to transform PGE2 present in the sample into a complex comprising PGE2 and the PGE2 binding moiety; (d) determining the level of the complex, thereby determining the level of PGE2 present in the second sample; and (e) comparing the level of PGE2 present in the first sample to the level of PGE2 present in the second sample, wherein a higher level of PGE2 in the second sample relative to the first sample is indicative of the progression of IBS in the subject and a lower level of PGE2 in the second sample relative to the first sample is indicative of the regression of IBS in the subject.

In one aspect, the present invention provides a computer-readable medium comprising code for controlling one or more processors to classify whether a serum or blood sample from an subject is associated with irritable bowel syndrome (IBS), the code comprising instructions to apply a statistical process to a data set comprising a diagnostic marker profile to produce a statistically derived decision classifying the sample as an IBS sample or non-IBS sample based upon the diagnostic marker profile, wherein the diagnostic marker profile indicates the level of at least one diagnostic marker selected from the group consisting of β-tryptase, histamine, prostaglandin E2 (PGE2), and a combination thereof.

In another aspect, the present invention provides a system for classifying whether a serum or blood sample from a subject is associated with irritable bowel syndrome (IBS), the system comprising: (a) a data acquisition module configured to produce a data set comprising a diagnostic marker profile, wherein the diagnostic marker profile indicates the presence or level of at least one diagnostic marker selected from the group consisting of β-tryptase, histamine, prostaglandin E2 (PGE2), and a combination thereof; (b) a data processing module configured to process the data set by applying a statistical process to the data set to produce a statistically derived decision classifying the sample as an IBS sample or non-IBS sample based upon the diagnostic marker profile; and (c) a display module configured to display the statistically derived decision.

In yet another aspect, the present invention provides a method for the detection of β-tryptase in a blood or serum sample, the method comprising the steps of: (a) coating a solid phase surface with a first anti-β-tryptase capture antibody; (b) contacting the solid phase surface with a blood or serum sample under conditions suitable to transform β-tryptase present in the sample into a complex comprising β-tryptase and the anti-β-tryptase capture antibody; (c) contacting the β-tryptase and the anti-β-tryptase complex with a second detecting antibody conjugated to alkaline phosphatase under conditions suitable to form a ternary complex; and (d) contacting the ternary complex with a CPSD luminescent substrate.

In one aspect, the present invention provides a method for classifying whether a sample from an individual is associated with IBS, the method comprising: (a) determining a diagnostic marker profile by detecting the presence or level of at least one diagnostic marker in the sample; and (b) classifying the sample as an IBS sample or non-IBS sample using an algorithm based upon the diagnostic marker profile.

In preferred embodiments of the various methods and assays of the present invention, the presence or level of 1, 2, 3, 4, 5, 6, 7, 8, 9, 10, 11, 12, 13, 14, 15, 16, 17, 18, 19, 20, 21, 22, 23, 24, 25, or more of the biomarkers shown in Table 1 is detected to generate a diagnostic marker profile that is useful for predicting IBS. In certain instances, the biomarkers described herein are analyzed using an immunoassay such as an enzyme-linked immunosorbent assay (ELISA) or an immunohistochemical assay.

TABLE 1

Exemplary diagnostic markers suitable for use in IBS classification.

| Family | Biomarker |
|---|---|
| Cytokine | CXCL8/IL-8 |
| | IL-1β |
| | TNF-related weak inducer of apoptosis (TWEAK) |
| | Leptin |
| | Osteoprotegerin (OPG) |
| | CCL19/MIP-3β |
| | CXCL1/GRO1/GROα |
| | CXCL4/PF-4 |
| | CXCL7/NAP-2 |
| Growth Factor | Epidermal growth factor (EGF) |
| | Vascular endothelial growth factor (VEGF) |
| | Pigment epithelium-derived factor (PEDF) |
| | Brain-derived neurotrophic factor (BDNF) |
| | Schwannoma-derived growth factor (SDGF)/amphiregulin |
| Anti-neutrophil antibody | Anti-neutrophil cytoplasmic antibody (ANCA) |
| | Perinuclear anti-neutrophil cytoplasmic antibody (pANCA) |
| ASCA | ASCA-IgA |
| | ASCA-IgG |
| Antimicrobial antibody | Anti-outer membrane protein C (OmpC) antibody |
| | Anti-Cbir-1 flagellin antibody |
| Lipocalin | Neutrophil gelatinase-associated lipocalin (NGAL) |
| MMP | MMP-9 |
| TIMP | TIMP-1 |

TABLE 1-continued

Exemplary diagnostic markers suitable for use in IBS classification.

| Family | Biomarker |
|---|---|
| Alpha-globulin | Alpha-2-macroglobulin (α2-MG) |
| | Haptoglobin precursor alpha-2 (Hpα2) |
| | Orosomucoid |
| Actin-severing protein | Gelsolin |
| S100 protein | Calgranulin A/S100A8/MRP-8 |
| Fibrinopeptide | Fibrinopeptide A (FIBA) |
| Serine protease | Tryptase |
| Prostaglandin | Prostaglandin E2 ($PGE_2$) |
| Others | Lactoferrin |
| | Anti-tissue transglutaminase (tTG) antibody |
| | Calcitonin gene-related peptide (CGRP) |
| | Histamine |

Figure 1:
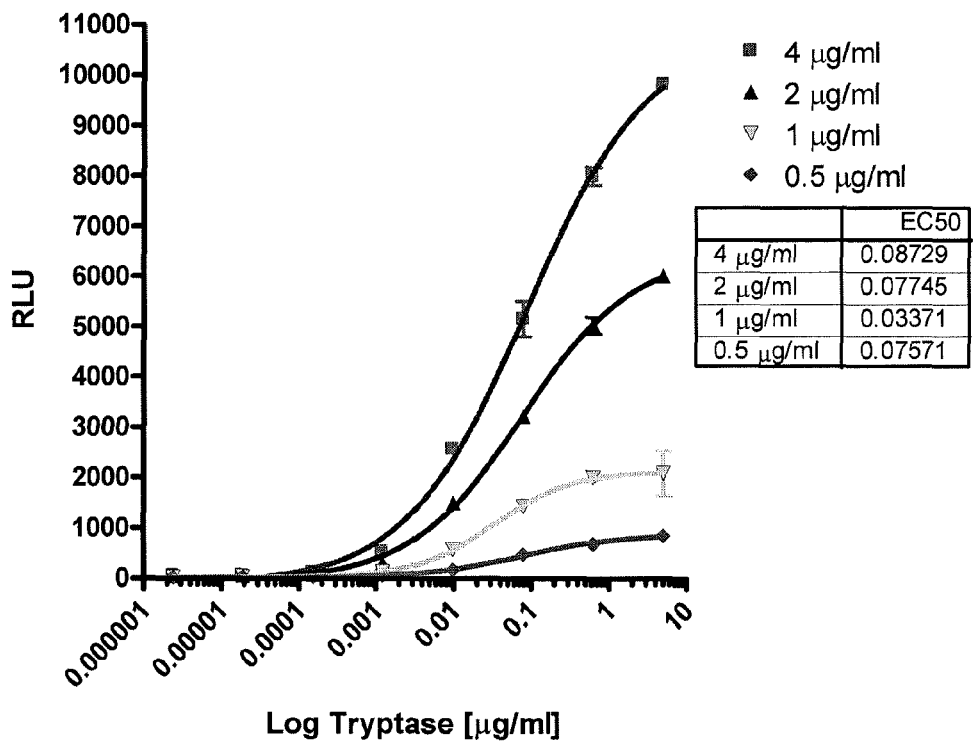
FIG. 1 illustrates a dose response curve in one embodiment of the present invention.

U.S. Patent Publication Nos. 2008/0085524, filed Aug. 14, 2007 and published Apr. 10, 2008; 2008/0166719, filed Aug. 20, 2007, published Jul. 10, 2008, are herein incorporated by reference in there entirety for all purposes.

DETAILED DESCRIPTION OF THE INVENTION

I. Introduction

Diagnosing a patient as having irritable bowel syndrome (IBS) can be challenging due to the similarity in symptoms between IBS and other diseases or disorders. For example, patients who have inflammatory bowel disease (IBD), but who exhibit mild signs and symptoms such as bloating, diarrhea, constipation, and abdominal pain can be difficult to distinguish from patients with IBS. As a result, the similarity in symptoms between IBS and IBD renders rapid and accurate diagnosis difficult and hampers early and effective treatment of the disease.

Although the pathology of irritable bowel syndrome (IBS) is not completely understood, many studies have led to the hypothesis that IBS is a disorder caused by the dysregulation of the brain-gut axis (for review, see, Öhman and Simrén, Nat Rev Gastroenterol Hepatol. 2010 March; 7(3):163-73). One observation that supports this theory is the repeated finding that an increased number of mast cells can be found in the intestinal mucosa of patients diagnosed with IBS (Guilarte, M. et al, *Gut* 56, 203-209 (2007); Walker, M. M. et al, *Pharmacol. Ther.* 29, 765-773 (2009); Akbar, A. et al, *Gut* 57, 923-929 (2008); Barbara, G. et al, *Gastroenterology* 126, 693-702 (2004); Barbara, G. et al, *Gastroenterology* 132, 26-37 (2007); Cremon, C. et al, *Am. J. Gastroenterol.* 104, 392-400 (2009); and O'Sullivan, M. et al, *Neurogastroenterol. Motil.*, 12, 449-457 (2000)). Similarly, some studies have also found that levels of mediators released from these cells, including histamine and serine proteases (e.g., tryptase), are found in the colonic mucosa of IBS patients (Buhner et al., *Gastroenterology* 2009 October; 137(4); Barbara et al., Gastroenterology, Volume: 122, Number: 4 Suppl. 1, Page: A-276, April 2002). However, this finding remains controversial, as other studies have reported that no such correlation exists (Guilarte et al., *Gut* 2007 February; 56(2): 203-9).

Regardless of the existence of increased levels of mast cell mediators in the colonic mucosa of IBS patients, such a correlation has a limited diagnostic value since colonic biopsies are invasive procedures. While researchers have looked for similar patterns in the blood/serum of IBS patients, fluids well suited for non-invasive diagnostics, no correlation has been reported to date (Lessof et al., Ann Allergy. 1983 August; 51(2 Pt 2):249-50; Guilarte, M. et al, *Gut* 56, 203-209 (2007); Öhman and Simrén, Nat Rev Gastroenterol Hepatol. 2010 March; 7(3):163-73).

Advantageously, the present invention provides, among other aspects, non-invasive methods and assays for the diagnosis and classification of irritable bowel syndrome. In certain embodiments, these methods and assays are related to the detection of the presence or concentration level of various IBS biomarkers in the blood and/or serum of subjects suspected of, or previously diagnosed as having IBS. In preferred embodiments, the methods comprise the detection of β-tryptase, and/or histamine, and/or prostaglandin $E_2$ in blood and serum samples from a subject. Additional markers can also be used.

Figure 12:
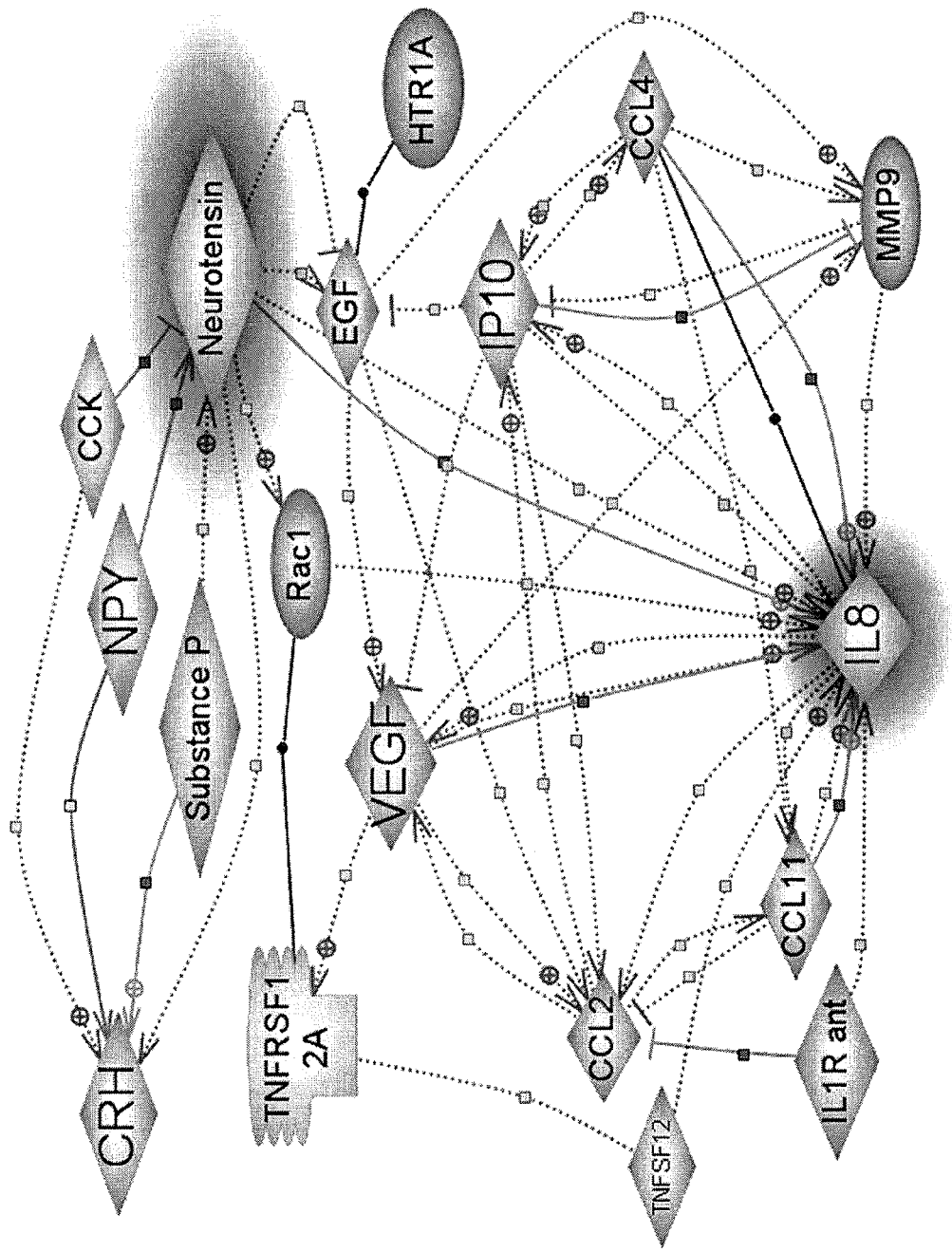
FIG. 12 illustrates one embodiment of a molecular pathway derived from the IBS markers identified and disclosed herein.

The present invention is based, in part, upon the surprising discovery that the accuracy of classifying a biological sample from an individual as an IBS sample can be substantially improved by detecting the presence or level of certain diagnostic markers (e.g., β-tryptase, prostaglandin $E_2$, histamine, cytokines, growth factors, anti-neutrophil antibodies, anti-*Saccharomyces cerevisiae* antibodies, antimicrobial antibodies, lactoferrin, etc.), alone or in combination with identifying the presence or severity of IBS-related symptoms based upon the individual's response to one or more questions (e.g., "Are you currently experiencing any symptoms?"). FIG. 12 shows a non-limiting example of a molecular pathway derived from the IBS markers identified and disclosed herein. In some aspects, the present invention uses statistical algorithms to aid in the classification of a sample as an IBS sample or non-IBS sample. In other aspects, the present invention uses statistical algorithms for ruling out other intestinal disorders (e.g., IBD), and then classifying the non-IBD sample to aid in the classification of IBS.

II. Definitions

As used herein, the following terms have the meanings ascribed to them unless specified otherwise.

The term "classifying" includes "to associate" or "to categorize" a sample with a disease state. In certain instances, "classifying" is based on statistical evidence, empirical evidence, or both. In certain embodiments, the methods and systems of classifying use a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "irritable bowel syndrome" or "IBS" includes a group of functional bowel disorders characterized by one or more symptoms including, but not limited to, abdominal pain, abdominal discomfort, change in bowel pattern, loose or more frequent bowel movements, diarrhea, and constipation, typically in the absence of any apparent structural abnormality. There are at least three forms of IBS, depending on which symptom predominates: (1) diarrhea-predominant (IBS-D); (2) constipation-predominant (IBS-C); and (3) IBS with alternating stool pattern (IBS-A). IBS can also occur in the form of a mixture of symptoms (IBS-M). There are also various clinical subtypes of IBS, such as post-infectious IBS (IBS-PI).

The term "transforming the sample" includes a physical and/or chemical change of the sample to extract a marker or to change or modify a marker as defined herein. An extraction, a manipulation, a chemical precipitation, an ELISA, a complexation, an immuno-extraction, a physical or chemical modification of the sample or marker to measure a level or concentration of a marker all constitute a transformation. As long as the sample or marker is not identical before and after the transformation step, the change or modification is a transformation.

The term "sample" includes any biological specimen obtained from an individual. Suitable samples for use in the present invention include, without limitation, whole blood, plasma, serum, saliva, urine, stool (i.e., feces), tears, and any other bodily fluid, or a tissue sample (i.e., biopsy) such as a small intestine or colon sample, and cellular extracts thereof (e.g., red blood cellular extract). In a preferred embodiment, the sample is a blood, plasma, or serum sample. In a more preferred embodiment, the sample is a serum sample. The use of samples such as serum, saliva, and urine is well known in the art (see, e.g., Hashida et al., *J. Clin. Lab. Anal.*, 11:267-86 (1997)). One skilled in the art will appreciate that samples such as serum samples can be diluted prior to the analysis of marker levels.

The term "biomarker" or "marker" includes any diagnostic marker such as a biochemical marker, serological marker, genetic marker, or other clinical or echographic characteristic that can be used to classify a sample from an individual as an IBS sample or to rule out one or more diseases or disorders associated with IBS-like symptoms in a sample from an individual. The term "biomarker" or "marker" also encompasses any classification marker such as a biochemical marker, serological marker, genetic marker, or other clinical or echographic characteristic that can be used to classify IBS into one of its various forms or clinical subtypes. Non-limiting examples of diagnostic markers suitable for use in the present invention are described below and include cytokines, growth factors, anti-neutrophil antibodies, anti-*Saccharomyces cerevisiae* antibodies, antimicrobial antibodies, anti-tissue transglutaminase (tTG) antibodies, lipocalins, matrix metalloproteinases (MMPs), tissue inhibitor of metalloproteinases (TIMPs), alpha-globulins, actin-severing proteins, S100 proteins, fibrinopeptides, calcitonin gene-related peptide (CGRP), tachykinins, ghrelin, neurotensin, corticotropin-releasing hormone (CRH), serine proteases (e.g., tryptase, elastase), prostaglandin (e.g., $PGE_2$), histamine, C-reactive protein (CRP), lactoferrin, anti-lactoferrin antibodies, calprotectin, hemoglobin, NOD2/CARD15, serotonin reuptake transporter (SERT), tryptophan hydroxylase-1,5-hydroxytryptamine (5-HT), lactulose, and the like. Examples of classification markers include, without limitation, leptin, SERT, tryptophan hydroxylase-1,5-HT, antrum mucosal protein 8, keratin-8, claudin-8, zonulin, corticotropin releasing hormone receptor-1 (CRHR1), corticotropin releasing hormone receptor-2 (CRHR2), tryptase, histamine, prostaglandin $E_2$ ($PGE_2$) and the like. In some embodiments, diagnostic markers can be used to classify IBS into one of its various forms or clinical subtypes. In other embodiments, classification markers can be used to classify a sample as an IBS sample or to rule out one or more diseases or disorders associated with IBS-like symptoms. One skilled in the art will know of additional diagnostic and classification markers suitable for use in the present invention.

In certain instances, the presence or level of at least one diagnostic marker is determined using an assay such as a hybridization assay or an amplification-based assay. Examples of hybridization assays and amplification-based assays suitable for use in the methods of the present invention are described above. In certain other instances, the presence or level of at least one diagnostic marker is determined using an immunoassay or an immunohistochemical assay. Non-limiting examples of immunoassays and immunohistochemical assays suitable for use in the methods of the present invention are described herein.

As used herein, the term "profile" includes any set of data that represents the distinctive features or characteristics associated with a disease or disorder such as IBS or IBD. The term encompasses a "diagnostic marker profile" that analyzes one or more diagnostic markers in a sample, a "symptom profile" that identifies one or more IBS-related clinical factors (i.e., symptoms) an individual is experiencing or has experienced, and combinations thereof. For example, a "diagnostic marker profile" can include a set of data that represents the presence or level of one or more diagnostic markers associated with IBS and/or IBD. Likewise, a "symptom profile" can include a set of data that represents the presence, severity, frequency, and/or duration of one or more symptoms associated with IBS and/or IBD.

In some embodiments, a panel for measuring one or more of the diagnostic markers and/or diagnostic profiles described above can be constructed and used for classifying the sample as an IBS sample or non-IBS sample. One skilled in the art will appreciate that the presence or level of a plurality of diagnostic markers can be determined simultaneously or sequentially, using, for example, an aliquot or dilution of the individual's sample. In certain instances, the level of a particular diagnostic marker in the individual's sample is considered to be elevated when it is at least about 10%, 15%, 20%, 25%, 50%, 75%, 100%, 125%, 150%, 175%, 200%, 250%, 300%, 350%, 400%, 450%, 500%, 600%, 700%, 800%, 900%, or 1000% greater than the level of the same marker in a comparative sample (e.g., a normal, GI control, IBD, and/or Celiac disease sample) or population of samples (e.g., greater than a median level of the same marker in a comparative population of normal, GI control, IBD, and/or Celiac disease samples). In certain other instances, the level of a particular diagnostic marker in the individual's sample is considered to be lowered when it is at least about 5%, 10%, 15%, 20%, 25%, 30%, 35%, 40%, 45%, 50%, 55%, 60%, 65%, 70%, 75%, 80%, 85%, 90%, or 95% less than the level of the same marker in a comparative sample (e.g., a normal, GI control, IBD, and/or Celiac disease sample) or population of samples (e.g., less than a median level of the same marker in a comparative population of normal, GI control, IBD, and/or Celiac disease samples).

The term "individual," "subject," or "patient" typically refers to humans, but also to other animals including, e.g., other primates, rodents, canines, felines, equines, ovines, porcines, and the like.

As used herein, the term "substantially the same amino acid sequence" includes an amino acid sequence that is similar, but not identical to, the naturally-occurring amino acid sequence. For example, an amino acid sequence that has substantially the same amino acid sequence as a naturally-occurring peptide, polypeptide, or protein can have one or more modifications such as amino acid additions, deletions, or substitutions relative to the amino acid sequence of the naturally-occurring peptide, polypeptide, or protein, provided that the modified sequence retains substantially at least one biological activity of the naturally-occurring peptide, polypeptide, or protein such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a peptide, polypeptide, or protein of the present invention, or a fragment thereof, is a modification that confers, for example, increased stability. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

The term "monitoring the progression or regression of IBS" includes the use of the methods, systems, and code of the present invention to determine the disease state (e.g., presence or severity of IBS) of an individual. In certain instances, the results of an algorithm (e.g., a learning statistical classifier system) are compared to those results obtained for the same individual at an earlier time. In some embodiments, the methods, systems, and code of the present invention can be used to predict the progression of IBS, e.g., by determining a likelihood for IBS to progress either rapidly or slowly in an individual based on an analysis of diagnostic markers and/or the identification or IBS-related symptoms. In other embodiments, the methods, systems, and code of the present invention can be used to predict the regression of IBS, e.g., by determining a likelihood for IBS to regress either rapidly or slowly in an individual based on an analysis of diagnostic markers and/or the identification or IBS-related symptoms.

The term "monitoring drug efficacy in an individual receiving a drug useful for treating IBS" includes the use of the methods, systems, and code of the present invention to determine the effectiveness of a therapeutic agent for treating IBS after it has been administered. In certain instances, the results of an algorithm (e.g., a learning statistical classifier system) are compared to those results obtained for the same individual before initiation of use of the therapeutic agent or at an earlier time in therapy. As used herein, a drug useful for treating IBS is any compound or drug used to improve the health of the individual and includes, without limitation, IBS drugs such as serotonergic agents, antidepressants, chloride channel activators, chloride channel blockers, guanylate cyclase agonists, antibiotics, opioids, neurokinin antagonists, antispasmodic or anticholinergic agents, belladonna alkaloids, barbiturates, glucagon-like peptide-1 (GLP-1) analogs, corticotropin releasing factor (CRF) antagonists, probiotics, free bases thereof, pharmaceutically acceptable salts thereof, derivatives thereof, analogs thereof, and combinations thereof.

The term "therapeutically effective amount or dose" includes a dose of a drug that is capable of achieving a therapeutic effect in a subject in need thereof. For example, a therapeutically effective amount of a drug useful for treating IBS can be the amount that is capable of preventing or relieving one or more symptoms associated with IBS. The exact amount can be ascertainable by one skilled in the art using known techniques (see, e.g., Lieberman, *Pharmaceutical Dosage Forms*, Vols. 1-3 (1992); Lloyd, *The Art, Science and Technology of Pharmaceutical Compounding* (1999); Pickar, *Dosage Calculations* (1999); and *Remington: The Science and Practice of Pharmacy*, 20th Edition, Gennaro, Ed., Lippincott, Williams & Wilkins (2003)).

III. Description of the Embodiments

The present invention provides methods, systems, and code for aiding in the diagnosis of irritable bowel syndrome in a subject. Similarly, the present invention provides methods, systems, and code for accurately classifying whether a sample from an individual is associated with irritable bowel syndrome (IBS). In some embodiments, the present invention relies on the use of a statistical algorithm (e.g., a learning statistical classifier system) and/or empirical data (e.g., the presence or level of an IBS marker). The present invention is also useful for ruling out one or more diseases or disorders that present with IBS-like symptoms and ruling in IBS using a combination of statistical algorithms and/or empirical data. Accordingly, the present invention provides an accurate diagnostic prediction of IBS and prognostic information useful for guiding treatment decisions.

A. Methods for Aiding in the Diagnosis of Irritable Bowel Syndrome (IBS)

In one aspect, the present invention provides methods for aiding in the diagnosis of irritable bowel syndrome in a subject by determining the level of 1, 2, 3, 4, 5, 6, 7, 8, 9, 10, 11, 12, 13, 14, 15, 16, 17, 18, 19, 20, 21, 22, 23, 24, 25, or more of the biomarkers shown in Table 1. In preferred embodiments, the methods provided herein rely on the detection of at least one biomarker selected from β-tryptase, histamine, prostaglandin $E_2$ ($PGE_2$), and a combination thereof.

In certain embodiments, methods are provided for aiding in the diagnosis of irritable bowel syndrome in a subject by determining the level of at least one biomarker selected from β-tryptase, histamine, prostaglandin $E_2$ ($PGE_2$), and a combination thereof in conjunction with at least one biomarker selected from the group consisting of Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), Anti-Human Tissue Transglutaminase IgA (tTG), and a combination thereof.

In yet other embodiments, methods are provided for aiding in the diagnosis of irritable bowel syndrome in a subject by determining the level of at least one biomarker selected from β-tryptase, histamine, prostaglandin $E_2$ ($PGE_2$), and a combination thereof in conjunction with at least one biomarker selected from the group consisting of a cytokine (e.g., IL-8, IL-1β, TWEAK, leptin, OPG, MIP-3β, GROα, CXCL4/PF-4, and/or CXCL7/NAP-2), growth factor (e.g., EGF, VEGF, PEDF, BDNF, and/or SDGF), anti-neutrophil antibody (e.g., ANCA, pANCA, cANCA, NSNA, and/or SAPPA), ASCA (e.g., ASCA-IgA, ASCA-IgG, and/or ASCA-IgM), antimicrobial antibody (e.g., anti-OmpC antibody, anti-flagellin antibody, and/or anti-I2 antibody), lactoferrin, anti-tTG antibody, lipocalin (e.g., NGAL, NGAL/MMP-9 complex), MMP (e.g., MMP-9), TIMP (e.g., TIMP-1), alpha-globulin (e.g., alpha-2-macroglobulin, haptoglobin, and/or orosomucoid), actin-severing protein (e.g., gelsolin), S100 protein (e.g., calgranulin), fibrinopeptide (e.g., FIBA), CGRP, tachykinin (e.g., Substance P), ghrelin, neurotensin, corticotropin-releasing hormone, and combinations thereof. In yet other embodiments, the presence or level of other diagnostic markers such as, for example, anti-lactoferrin antibody, L-selectin/CD62L, elastase, C-reactive protein (CRP), calprotectin, anti-U1-70 kDa autoantibody, zona occludens 1 (ZO-1), vasoactive intestinal peptide (VIP), serum amyloid A, gastrin, and a combination thereof may also be detected.

In another aspect, the present invention provides a method for classifying whether a sample from an individual is associated with IBS, the method comprising: (a) determining a diagnostic marker profile by detecting the presence or level of at least one diagnostic marker in the sample; (b) classifying the sample as an IBD sample or non-IBD sample using a first statistical algorithm based upon the diagnostic marker profile; and if the sample is classified as a non-IBD sample, (c) classifying the non-IBD sample as an IBS sample or non-IBS sample using a second statistical algorithm based upon the same diagnostic marker profile as determined in step (a) or a different diagnostic marker profile.

The diagnostic markers used for ruling out IBD can be the same as the diagnostic markers used for ruling in IBS. Alternatively, the diagnostic markers used for ruling out IBD can be different than the diagnostic markers used for ruling in IBS.

In some embodiments, the method of first ruling out IBD (i.e., classifying the sample as an IBD sample or non-IBD sample) and then ruling in IBS (i.e., classifying the non-IBD sample as an IBS sample or non-IBS sample) comprises determining a diagnostic marker profile optionally in combination with a symptom profile, wherein the symptom profile is determined by identifying the presence or severity of at least one symptom in the individual; classifying the sample as an IBD sample or non-IBD sample using a first statistical algorithm based upon the diagnostic marker profile and the symptom profile; and if the sample is classified as a non-IBD sample, classifying the non-IBD sample as an IBS sample or non-IBS sample using a second statistical algorithm based upon the same profiles as determined in step (a) or different profiles. One skilled in the art will appreciate that the diagnostic marker profile and the symptom profile can be determined simultaneously or sequentially in any order.

In additional embodiments, the methods of the present invention further comprise ruling out intestinal inflammation. Non-limiting examples of intestinal inflammation include acute inflammation, diverticulitis, ileal pouch-anal anastomosis, microscopic colitis, infectious diarrhea, and combinations thereof. In some instances, the intestinal inflammation is ruled out based upon the presence or level of C-reactive protein (CRP), lactoferrin, calprotectin, or combinations thereof.

As described herein, the methods of the present invention can further comprise sending the IBS classification results to a clinician, e.g., a gastroenterologist or a general practitioner. The methods can also provide a diagnosis in the form of a probability that the individual has IBS. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having IBS. In some instances, the methods of the present invention further provide a prognosis of IBS in the individual. For example, the prognosis can be surgery, development of a category or clinical subtype of IBS, development of one or more symptoms, or recovery from the disease.

1. β-Tryptase

In one aspect, a method for aiding in the diagnosis of irritable bowel syndrome (IBS) in a subject is provided, the method comprising: (a) contacting a blood or serum sample from the subject with a β-tryptase binding moiety under conditions suitable to transform β-tryptase present in the sample into a complex comprising β-tryptase and the β-tryptase binding moiety; and (b) determining the level of the complex, thereby determining the level of β-tryptase present in the sample. In one embodiment, the method further comprises: (c) comparing the level of β-tryptase present in the sample to a control level, wherein a difference in the level of β-tryptase present in the sample relative to the control level is indicative of an increased likelihood of the subject having IBS.

In a specific embodiment, the present invention provides an assay to aid in the diagnosis of IBS, the assay comprising: (a) contacting a sample having β-tryptase contained therein under conditions suitable to transform the β-tryptase into a complex comprising β-tryptase and a capture anti-tryptase antibody; (b) contacting the complex with an enzyme labeled indicator antibody to transform the complex into a labeled complex; (c) contacting the labeled complex with a substrate for the enzyme; and (d) detecting the presence or level of β-tryptase in the sample.

In certain embodiments, a control level is the level of β-tryptase present in a blood or serum sample from a healthy subject or an average level of β-tryptase present in blood or serum samples from a cohort of healthy subjects. In other embodiments, a control level is the level of β-tryptase present in a blood or serum sample from a non-IBS subject or an average level of β-tryptase present in blood or serum samples from a cohort of non-IBS subjects. In another embodiment, a control level is the level of β-tryptase present in a blood or serum sample from a diseased subject or an average level of β-tryptase present in blood or serum samples from a cohort of diseased subjects. Non-limiting examples of diseased subjects that are useful for determining a control level from include subjects with IBS, subjects with a non-IBS gastrointestinal disease, subjects with inflammatory bowel disease (IBD), subjects with ulcerative colitis (UC), subjects with Crohn's disease (CD), subjects with celiac disease, subjects with gastroesophageal reflux disease (GERD), subjects with cancer, subjects with a cancer of the gastrointestinal tract, subjects with a cancer of the stomach, subjects with a cancer of the small or large bowel, and the like.

In cases where the control level is a level of β-tryptase in a blood or serum sample of a healthy subject or healthy subjects, an increased level of β-tryptase present in a sample from a subject, relative to the control level, is indicative of an increased likelihood of the subject having IBS. Conversely, where the control is a healthy subject or subjects, a similar or reduced level of β-tryptase present in a sample from a subject, relative to the control level, is indicative of an increased likelihood of the subject not having IBS.

In cases where the control level is a level of β-tryptase in a blood or serum sample of a subject or subjects with IBS, a similar or increased level of β-tryptase present in a sample from a subject, relative to the control level, is indicative of an increased likelihood of the subject having IBS. Conversely, where the control is a subject or subjects with IBS, a reduced level of β-tryptase present in a sample from a subject, relative to the control level, is indicative of an increased likelihood of the subject not having IBS.

In certain aspects of the invention, methods are provided for aiding in the diagnosis of irritable bowel syndrome (IBS) in a subject comprising the detection of β-tryptase in a blood or serum sample and at least one additional blood or serum biomarker selected from histamine and prostaglandin $E_2$ ($PGE_2$). In one embodiment, the method comprises detecting or determining the level of β-tryptase and histamine from a blood or serum sample from a subject. In another embodiment, the method comprises detecting or determining the level of β-tryptase and $PGE_2$ from a blood or serum sample from a subject. In a third embodiment, the method comprises detecting or determining the level of β-tryptase, histamine, and $PGE_2$ from a blood or serum sample from a subject. Preferably, β-tryptase, histamine, and/or $PGE_2$ are detected from the same blood or serum sample, although in certain instances the biomarkers may be detected in different blood or serum samples taken from the same individual, for example, at the same time or at different times. In certain embodiments, the biomarkers may be detected in separate assays performed with different aliquots of a blood or serum sample from a subject. In other embodiments, the biomarkers may be detected in a single multiplex detection assay, for example, in a Luminex© xMAP© assay.

In yet other aspects of the invention, methods are provided for aiding in the diagnosis of irritable bowel syndrome (IBS) in a subject comprising the detection of β-tryptase in a blood or serum sample and at least one additional biomarker selected from Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), Anti-Human Tissue Transglutaminase IgA (tTG), and a combination thereof. In certain embodiments, at least 2 of the additional biomarkers may be detected. In other embodiments, at least 3, 4, 5, 6, 7, 8, 9, or 10 of the additional biomarkers may be detected.

The sample used for detecting or determining the presence or level of at least one diagnostic marker is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the methods of the present invention further comprise obtaining the sample from the individual prior to detecting or determining the presence or level of at least one diagnostic marker in the sample. In a preferred embodiment, the additional biomarker may be detected from a blood or serum sample. In other embodiments, the additional biomarker may be detected from a stool sample or a biopsy from the bowel of the subject.

In one embodiment, the method comprises detecting or determining the level of β-tryptase from a blood or serum sample and Brain-Derived Neurotropic Factor (BDNF) from a biological sample. In a preferred embodiment, Brain-Derived Neurotropic Factor (BDNF) is detected in a blood or serum sample from the subject. In another preferred embodiment, Brain-Derived Neurotropic Factor (BDNF) is detected in a stool sample or a biopsy from the bowel of the subject. In other embodiments, at least one additional biomarker is also detected.

In one embodiment, the method comprises detecting or determining the level of β-tryptase from a blood or serum sample and Neutrophil Gelatinase-Associated Lipocalin (NGAL) from a biological sample. In a preferred embodiment, Neutrophil Gelatinase-Associated Lipocalin (NGAL) is detected in a blood or serum sample from the subject. In another preferred embodiment, Neutrophil Gelatinase-Associated Lipocalin (NGAL) is detected in a stool sample or a biopsy from the bowel of the subject. In other embodiments, at least one additional biomarker is also detected.

In one embodiment, the method comprises detecting or determining the level of β-tryptase from a blood or serum sample and TNF-related Weak Inducer of Apoptosis (TWEAK) from a biological sample. In a preferred embodiment, TNF-related Weak Inducer of Apoptosis (TWEAK) is detected in a blood or serum sample from the subject. In another preferred embodiment, TNF-related Weak Inducer of Apoptosis (TWEAK) is detected in a stool sample or a biopsy from the bowel of the subject. In other embodiments, at least one additional biomarker is also detected.

In one embodiment, the method comprises detecting or determining the level of β-tryptase from a blood or serum sample and Growth-Related Oncogene Alpha (GRO-α) from a biological sample. In a preferred embodiment, Growth-Related Oncogene Alpha (GRO-α) is detected in a blood or serum sample from the subject. In another preferred embodiment, Growth-Related Oncogene Alpha (GRO-α) is detected in a stool sample or a biopsy from the bowel of the subject. In other embodiments, at least one additional biomarker is also detected.

In one embodiment, the method comprises detecting or determining the level of β-tryptase from a blood or serum sample and Interleukin-1 Beta (IL-1β) from a biological sample. In a preferred embodiment, Interleukin-1 Beta (IL-1β) is detected in a blood or serum sample from the subject. In another preferred embodiment, Interleukin-1 Beta (IL-1β) is detected in a stool sample or a biopsy from the bowel of the subject. In other embodiments, at least one additional biomarker is also detected.

In one embodiment, the method comprises detecting or determining the level of β-tryptase from a blood or serum sample and Tissue Inhibitor of Metalloproteinase-1 (TIMP-1) from a biological sample. In a preferred embodiment, Tissue Inhibitor of Metalloproteinase-1 (TIMP-1) is detected in a blood or serum sample from the subject. In another preferred embodiment, Tissue Inhibitor of Metalloproteinase-1 (TIMP-1) is detected in a stool sample or a biopsy from the bowel of the subject. In other embodiments, at least one additional biomarker is also detected.

In one embodiment, the method comprises detecting or determining the level of β-tryptase from a blood or serum sample and Anti-*Saccharomyces cerevisiae* Antibody (ASCA-IgA) from a biological sample. In a preferred embodiment, Anti-*Saccharomyces cerevisiae* Antibody (ASCA-IgA) is detected in a blood or serum sample from the subject. In another preferred embodiment, Anti-*Saccharomyces cerevisiae* Antibody (ASCA-IgA) is detected in a stool sample or a biopsy from the bowel of the subject. In other embodiments, at least one additional biomarker is also detected.

In one embodiment, the method comprises detecting or determining the level of β-tryptase from a blood or serum sample and Anti-CBir-1 Antibody (CBir1) from a biological sample. In a preferred embodiment, Anti-CBir-1 Antibody (CBir1) is detected in a blood or serum sample from the subject. In another preferred embodiment, Anti-CBir-1 Antibody (CBir1) is detected in a stool sample or a biopsy from the bowel of the subject. In other embodiments, at least one additional biomarker is also detected.

In one embodiment, the method comprises detecting or determining the level of β-tryptase from a blood or serum sample and Anti-Human Neutrophil Cytoplasmic Antibody (ANCA) from a biological sample. In a preferred embodiment, Anti-Human Neutrophil Cytoplasmic Antibody (ANCA) is detected in a blood or serum sample from the subject. In another preferred embodiment, Anti-Human Neutrophil Cytoplasmic Antibody (ANCA) is detected in a stool sample or a biopsy from the bowel of the subject. In other embodiments, at least one additional biomarker is also detected.

In one embodiment, the method comprises detecting or determining the level of β-tryptase from a blood or serum sample and Anti-Human Tissue Transglutaminase IgA (tTG) from a biological sample. In a preferred embodiment, Anti-Human Tissue Transglutaminase IgA (tTG) is detected in a blood or serum sample from the subject. In another preferred embodiment, Anti-Human Tissue Transglutaminase IgA (tTG) is detected in a stool sample or a biopsy from the bowel of the subject. In other embodiments, at least one additional biomarker is also detected.

In one embodiment, the method comprises detecting or determining the level of β-tryptase from a blood or serum sample and all of Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), and Anti-Human Tissue Transglutaminase IgA (tTG) from a blood or serum sample, a stool sample, or a biopsy from the bowel of the subject.

In certain embodiments, the presence or level of at least one diagnostic marker is determined using an assay such as a hybridization assay or an amplification-based assay. Examples of hybridization assays suitable for use in the methods of the present invention include, but are not limited to, Northern blotting, dot blotting, RNase protection, and a combination thereof. A non-limiting example of an amplification-based assay suitable for use in the methods of the present invention includes a reverse transcriptase-polymerase chain reaction (RT-PCR).

In certain other embodiments, the presence or level of at least one diagnostic marker is determined using an immunoassay or an immunohistochemical assay. A non-limiting example of an immunoassay suitable for use in the methods of the present invention includes an enzyme-linked immunosorbent assay (ELISA). Examples of immunohistochemical assays suitable for use in the methods of the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays.

In a preferred embodiment, the presence or level of β-tryptase is determined using a sandwich enzyme-linked immunosorbent assay (ELISA). Any suitable antibody pair may be used for the capture and detecting antibodies in a sandwich ELISA. One of skill in the art will know and appreciate how to select an appropriate antibody pair for the assay. Generally, two antibodies are selected that bind to the target of interest, e.g., β-tryptase, at different epitopes such that the binding of the first (capture) antibody does not interfere with the second (detecting) antibody. In certain embodiments, the detecting antibody will be conjugated to an enzyme, for example, alkaline phophatase, to aid in the detection of the complex. In other embodiments, a secondary antibody conjugated to an enzyme (e.g., alkaline phophatase), which binds to the detecting antibody, may be used in the assay. Generally, the complex will then be detected by the use of a luminescent substrate, for example, Ultra LITE™ (NAG Research Laboratories); SensoLyte® (AnaSpec); SuperSignal ELISA Femto Maximum Sensitivity Substrate (Thermo Scientific); SuperSignal ELISA Pico Chemiluminescent Substrate (Thermo Scientific); CPSD (disodium 3-(4-methoxyspiro{1,2-dioxetane-3,2'-(5'-chloro)tricyclo[3.3.1.13,7]decan}-4-yl)phenyl phosphate; Tropix, Inc). In a preferred embodiment, the β-tryptase sandwich ELISA comprises the use of an alkaline phosphatase conjugated anti-tryptase antibody as the detecting antibody and a CPSD containing luminescent substrate to enhance the assay sensitivity. The CPSD substrate can be found in chemiluminescent detection systems, such as the ELISA-Light™ System (Applied Biosystems). In a particularly preferred embodiment, the detection antibody used in the sandwich ELISA is the anti-tryptase antibody G3 (sc-33676; Santa Cruz Biotechnology, Inc.; Santa Cruz, Calif.).

In some embodiments, the methods provided herein further include the step of determining a symptom profile for the subject, wherein the symptom profile is determined by identifying the presence or severity of at least one symptom in the subject. In a preferred embodiment, the method comprises: (d) determining a symptom profile for the subject, wherein the symptom profile is determined by identifying the presence or severity of at least one symptom in the subject; and (e) diagnosing the subject as having IBS or not having IBS using an algorithm based upon the level of an IBS biomarker and the system profile. In a preferred embodiment, the method for aiding in the diagnosis of irritable bowel syndrome (IBS) in a subject comprises determining a diagnostic marker profile, for example for β-tryptase or a combination thereof as described herein, optionally in combination with a symptom profile, wherein the symptom profile is determined by identifying the presence or severity of at least one symptom in the individual; and classifying the sample as an IBS sample or non-IBS sample using an algorithm based upon the diagnostic marker profile and the symptom profile.

The symptom profile is typically determined by identifying the presence or severity of at least one symptom selected from the group consisting of chest pain, chest discomfort, heartburn, uncomfortable fullness after having a regular-sized meal, inability to finish a regular-sized meal, abdominal pain, abdominal discomfort, constipation, diarrhea, bloating, abdominal distension, negative thoughts or feelings associated with having pain or discomfort, and combinations thereof.

In preferred embodiments, the presence or severity of 1, 2, 3, 4, 5, 6, 7, 8, 9, 10, or more of the symptoms described herein is identified to generate a symptom profile that is useful for predicting IBS. In certain instances, a questionnaire or other form of written, verbal, or telephone survey is used to produce the symptom profile. The questionnaire or survey typically comprises a standardized set of questions and answers for the purpose of gathering information from respondents regarding their current and/or recent IBS-related symptoms.

In some embodiments, the symptom profile is produced by compiling and/or analyzing all or a subset of the answers to the questions set forth in the questionnaire or survey. In other embodiments, the symptom profile is produced based upon the individual's response to the following question: "Are you currently experiencing any symptoms?" The symptom profile generated in accordance with either of these embodiments can be used in combination with a diagnostic marker profile in the algorithmic-based methods described herein to improve the accuracy of predicting IBS.

In some embodiments, the methods provided herein further include providing a probability that a subject has IBS. In certain embodiments, the method may comprise providing a probability that the is subject highly unlikely, unlikely, likely, or highly likely has IBS. In related embodiments, methods are provided that further include providing a probability that a sample classified as an IBS sample or a non-IBS sample is from a subject with IBS. In certain embodiments, the method may comprise providing a probability that the is sample is from a subject that highly unlikely, unlikely, likely, or highly likely has IBS.

In other embodiments, the methods provided herein further include classifying a diagnosis of IBS as IBS-constipation (IBS-C), IBS-diarrhea (IBS-D), IBS-mixed (IBS-M), IBS-alternating (IBS-A), or post-infectious IBS (IBS-PI). In related embodiments, methods are provided herein to further classify a sample as an IBS-constipation (IBS-C), IBS-diarrhea (IBS-D), IBS-mixed (IBS-M), IBS-alternating (IBS-A), or post-infectious IBS (IBS-PI) sample.

In one embodiment, the present invention provides an assay to aid in the differentiation of IBS-D and IBS-A from IBS-C, the assay comprising: (a) contacting a sample having β-tryptase contained therein under conditions suitable to transform the β-tryptase into a complex comprising β-tryptase and a capture anti-tryptase antibody; (b) contacting the complex with an enzyme labeled indicator antibody to transform the complex into a labeled complex; (c) contacting the labeled complex with a substrate for the enzyme; and (d) detecting the presence or level of β-tryptase in the sample.

In some instances, the assay to aid in the differentiation of IBS-D and IBS-A from IBS-C further comprises detecting the presence or level of a prostaglandin (e.g., $PGE_2$); and/or histamine in the sample.

In yet other embodiments, methods provided herein further include diagnosing a subject not having IBS as having IBD, as not having IBD, as having celiac disease, as not having celiac disease, as being a healthy subject, or as not having a gastrointestinal disease. In a related embodiment, methods are provided herein that further classify a non-IBS sample as an IBD sample, a non-IBD sample, a healthy sample, a non-gastrointestinal disease sample, a celiac sample, and the like.

In one embodiment, the methods provided herein comprise the use of an algorithm based upon the level of an IBS biomarker. In certain embodiments, the algorithm is further based upon the system profile. In a preferred embodiment, the algorithm comprises a statistical algorithm, for example a learning statistical classifier system. In a more preferred embodiment, the algorithm comprises a combination of at least two learning statistical classifier systems. In a most preferred embodiment, the combination of at least two learning statistical classifier systems comprises a random forest classifier and a neural network classifier.

2. Histamine

In one specific aspect, a method for aiding in the diagnosis of irritable bowel syndrome (IBS) in a subject is provided, the method comprising: (a) contacting a blood or serum sample from the subject with a histamine binding moiety under conditions suitable to transform histamine present in the sample into a complex comprising histamine and the histamine binding moiety; and (b) determining the level of the complex, thereby determining the level of histamine present in the sample. In one embodiment, the method further comprises: (c) comparing the level of histamine present in the sample to a control level, wherein a difference in the level of histamine present in the sample relative to the control level is indicative of an increased likelihood of the subject having IBS.

In a specific embodiment, the present invention provides an assay to aid in the diagnosis of IBS, the assay comprising: (a) contacting a sample having histamine contained therein under conditions suitable to transform the histamine into a complex comprising histamine and a capture anti-tryptase antibody; (b) contacting the complex with an enzyme labeled indicator antibody to transform the complex into a labeled complex; (c) contacting the labeled complex with a substrate for the enzyme; and (d) detecting the presence or level of histamine in the sample.

In certain embodiments, a control level is the level of histamine present in a blood or serum sample from a healthy subject or an average level of histamine present in blood or serum samples from a cohort of healthy subjects. In other embodiments, a control level is the level of histamine present in a blood or serum sample from a non-IBS subject or an average level of histamine present in blood or serum samples from a cohort of non-IBS subjects. In another embodiment, a control level is the level of histamine present in a blood or serum sample from a diseased subject or an average level of histamine present in blood or serum samples from a cohort of diseased subjects. Non-limiting examples of diseased subjects that are useful for determining a control level from include subjects with IBS, subjects with a non-IBS gastrointestinal disease, subjects with inflammatory bowel disease (IBD), subjects with ulcerative colitis (UC), subjects with Crohn's disease (CD), subjects with celiac disease, subjects with gastroesophageal reflux disease (GERD), subjects with cancer, subjects with a cancer of the gastrointestinal tract, subjects with a cancer of the stomach, subjects with a cancer of the small or large bowel, and the like.

In cases where the control level is a level of histamine in a blood or serum sample of a healthy subject or healthy subjects, an increased level of histamine present in a sample from a subject, relative to the control level, is indicative of an increased likelihood of the subject having IBS. Conversely, where the control is a healthy subject or subjects, a similar or reduced level of histamine present in a sample from a subject, relative to the control level, is indicative of an increased likelihood of the subject not having IBS.

In cases where the control level is a level of histamine in a blood or serum sample of a subject or subjects with IBS, a similar or increased level of histamine present in a sample from a subject, relative to the control level, is indicative of an increased likelihood of the subject having IBS. Conversely, where the control is a subject or subjects with IBS, a reduced level of histamine present in a sample from a subject, relative to the control level, is indicative of an increased likelihood of the subject not having IBS.

In certain aspects of the invention, methods are provided for aiding in the diagnosis of irritable bowel syndrome (IBS) in a subject comprising the detection of histamine in a blood or serum sample and at least one additional blood or serum biomarker selected from prostaglandin $E_2$ ($PGE_2$) and β-tryptase. In one embodiment, the method comprises detecting or determining the level of histamine and prostaglandin $E_2$ ($PGE_2$) from a blood or serum sample from a subject. In another embodiment, the method comprises detecting or determining the level of histamine and β-tryptase from a blood or serum sample from a subject. In a third embodiment, the method comprises detecting or determining the level of histamine, prostaglandin $E_2$ ($PGE_2$), and β-tryptase from a blood or serum sample from a subject. Preferably, histamine, prostaglandin $E_2$ ($PGE_2$), and/or β-tryptase are detected from the same blood or serum sample, although in certain instances the biomarkers may be detected in different blood or serum samples taken from the same individual, for example, at the same time or at different times. In certain embodiments, the biomarkers may be detected in separate assays performed with different aliquots of a blood or serum sample from a subject. In other embodiments, the biomarkers may be detected in a single multiplex detection assay, for example, in a Luminex© xMAP© assay.

In yet other aspects of the invention, methods are provided for aiding in the diagnosis of irritable bowel syndrome (IBS) in a subject comprising the detection of histamine in a blood or serum sample and at least one additional biomarker selected from Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), Anti-Human Tissue Transglutaminase IgA (tTG), and a combination thereof. In certain embodiments, at least 2 of the additional biomarkers may be detected. In other embodiments, at least 3, 4, 5, 6, 7, 8, 9, or 10 of the additional biomarkers may be detected.

The sample used for detecting or determining the presence or level of at least one diagnostic marker is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the methods of the present invention further comprise obtaining the sample from the individual prior to detecting or determining the presence or level of at least one diagnostic marker in the sample. In a preferred embodiment, the additional biomarker may be detected from a blood or serum sample. In other embodiments, the additional biomarker may be detected from a stool sample or a biopsy from the bowel of the subject.

In one embodiment, the method comprises detecting or determining the level of histamine from a blood or serum sample and Brain-Derived Neurotropic Factor (BDNF) from a biological sample. In a preferred embodiment, Brain-Derived Neurotropic Factor (BDNF) is detected in a blood or serum sample from the subject. In another preferred embodiment, Brain-Derived Neurotropic Factor (BDNF) is detected in a stool sample or a biopsy from the bowel of the subject. In other embodiments, at least one additional biomarker is also detected.

In one embodiment, the method comprises detecting or determining the level of histamine from a blood or serum sample and Neutrophil Gelatinase-Associated Lipocalin (NGAL) from a biological sample. In a preferred embodiment, Neutrophil Gelatinase-Associated Lipocalin (NGAL) is detected in a blood or serum sample from the subject. In another preferred embodiment, Neutrophil Gelatinase-Associated Lipocalin (NGAL) is detected in a stool sample or a biopsy from the bowel of the subject. In other embodiments, at least one additional biomarker is also detected.

In one embodiment, the method comprises detecting or determining the level of histamine from a blood or serum sample and TNF-related Weak Inducer of Apoptosis (TWEAK) from a biological sample. In a preferred embodiment, TNF-related Weak Inducer of Apoptosis (TWEAK) is detected in a blood or serum sample from the subject. In another preferred embodiment, TNF-related Weak Inducer of Apoptosis (TWEAK) is detected in a stool sample or a biopsy from the bowel of the subject. In other embodiments, at least one additional biomarker is also detected.

In one embodiment, the method comprises detecting or determining the level of histamine from a blood or serum sample and Growth-Related Oncogene Alpha (GRO-α) from a biological sample. In a preferred embodiment, Growth-Related Oncogene Alpha (GRO-α) is detected in a blood or serum sample from the subject. In another preferred embodiment, Growth-Related Oncogene Alpha (GRO-α) is detected in a stool sample or a biopsy from the bowel of the subject. In other embodiments, at least one additional biomarker is also detected.

In one embodiment, the method comprises detecting or determining the level of histamine from a blood or serum sample and Interleukin-1 Beta (IL-1β) from a biological sample. In a preferred embodiment, Interleukin-1 Beta (IL-1β) is detected in a blood or serum sample from the subject. In another preferred embodiment, Interleukin-1 Beta (IL-1β) is detected in a stool sample or a biopsy from the bowel of the subject. In other embodiments, at least one additional biomarker is also detected.

In one embodiment, the method comprises detecting or determining the level of histamine from a blood or serum sample and Tissue Inhibitor of Metalloproteinase-1 (TIMP-1) from a biological sample. In a preferred embodiment, Tissue Inhibitor of Metalloproteinase-1 (TIMP-1) is detected in a blood or serum sample from the subject. In another preferred embodiment, Tissue Inhibitor of Metalloproteinase-1 (TIMP-1) is detected in a stool sample or a biopsy from the bowel of the subject. In other embodiments, at least one additional biomarker is also detected.

In one embodiment, the method comprises detecting or determining the level of histamine from a blood or serum sample and Anti-*Saccharomyces cerevisiae* Antibody (ASCA-IgA) from a biological sample. In a preferred embodiment, Anti-*Saccharomyces cerevisiae* Antibody (ASCA-IgA) is detected in a blood or serum sample from the subject. In another preferred embodiment, Anti-*Saccharomyces cerevisiae* Antibody (ASCA-IgA) is detected in a stool sample or a biopsy from the bowel of the subject. In other embodiments, at least one additional biomarker is also detected.

In one embodiment, the method comprises detecting or determining the level of histamine from a blood or serum sample and Anti-CBir-1 Antibody (CBir1) from a biological sample. In a preferred embodiment, Anti-CBir-1 Antibody (CBir1) is detected in a blood or serum sample from the subject. In another preferred embodiment, Anti-CBir-1 Antibody (CBir1) is detected in a stool sample or a biopsy from the bowel of the subject. In other embodiments, at least one additional biomarker is also detected.

In one embodiment, the method comprises detecting or determining the level of histamine from a blood or serum sample and Anti-Human Neutrophil Cytoplasmic Antibody (ANCA) from a biological sample. In a preferred embodiment, Anti-Human Neutrophil Cytoplasmic Antibody (ANCA) is detected in a blood or serum sample from the subject. In another preferred embodiment, Anti-Human Neutrophil Cytoplasmic Antibody (ANCA) is detected in a stool sample or a biopsy from the bowel of the subject. In other embodiments, at least one additional biomarker is also detected.

In one embodiment, the method comprises detecting or determining the level of histamine from a blood or serum sample and Anti-Human Tissue Transglutaminase IgA (tTG) from a biological sample. In a preferred embodiment, Anti-Human Tissue Transglutaminase IgA (tTG) is detected in a blood or serum sample from the subject. In another preferred embodiment, Anti-Human Tissue Transglutaminase IgA (tTG) is detected in a stool sample or a biopsy from the bowel of the subject. In other embodiments, at least one additional biomarker is also detected.

In one embodiment, the method comprises detecting or determining the level of histamine from a blood or serum sample and all of Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), and Anti-Human Tissue Transglutaminase IgA (tTG) from a blood or serum sample, a stool sample, or a biopsy from the bowel of the subject.

In certain embodiments, the presence or level of at least one diagnostic marker is determined using an assay such as a hybridization assay or an amplification-based assay. Examples of hybridization assays suitable for use in the methods of the present invention include, but are not limited to, Northern blotting, dot blotting, RNase protection, and a combination thereof. A non-limiting example of an amplification-based assay suitable for use in the methods of the present invention includes a reverse transcriptase-polymerase chain reaction (RT-PCR).

In certain other embodiments, the presence or level of at least one diagnostic marker is determined using an immunoassay or an immunohistochemical assay. A non-limiting example of an immunoassay suitable for use in the methods of the present invention includes an enzyme-linked immunosorbent assay (ELISA). Examples of immunohistochemical assays suitable for use in the methods of the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays.

In some embodiments, the methods provided herein further include the step of determining a symptom profile for the subject, wherein the symptom profile is determined by identifying the presence or severity of at least one symptom in the subject. In a preferred embodiment, the method comprises: (d) determining a symptom profile for the subject, wherein the symptom profile is determined by identifying the presence or severity of at least one symptom in the subject; and (e) diagnosing the subject as having IBS or not having IBS using an algorithm based upon the level of an IBS biomarker and the system profile. In a preferred embodiment, the method for aiding in the diagnosis of irritable bowel syndrome (IBS) in a subject comprises determining a diagnostic marker profile, for example for histamine or a combination thereof as described herein, optionally in combination with a symptom profile, wherein the symptom profile is determined by identifying the presence or severity of at least one symptom in the individual; and classifying the sample as an IBS sample or non-IBS sample using an algorithm based upon the diagnostic marker profile and the symptom profile.

The symptom profile is typically determined by identifying the presence or severity of at least one symptom selected from the group consisting of chest pain, chest discomfort, heartburn, uncomfortable fullness after having a regular-sized meal, inability to finish a regular-sized meal, abdominal pain, abdominal discomfort, constipation, diarrhea, bloating, abdominal distension, negative thoughts or feelings associated with having pain or discomfort, and combinations thereof.

In preferred embodiments, the presence or severity of 1, 2, 3, 4, 5, 6, 7, 8, 9, 10, or more of the symptoms described herein is identified to generate a symptom profile that is useful for predicting IBS. In certain instances, a questionnaire or other form of written, verbal, or telephone survey is used to produce the symptom profile. The questionnaire or survey typically comprises a standardized set of questions and answers for the purpose of gathering information from respondents regarding their current and/or recent IBS-related symptoms.

In some embodiments, the symptom profile is produced by compiling and/or analyzing all or a subset of the answers to the questions set forth in the questionnaire or survey. In other embodiments, the symptom profile is produced based upon the individual's response to the following question: "Are you currently experiencing any symptoms?" The symptom profile generated in accordance with either of these embodiments can be used in combination with a diagnostic marker profile in the algorithmic-based methods described herein to improve the accuracy of predicting IBS.

In some embodiments, the methods provided herein further include providing a probability that a subject has IBS. In certain embodiments, the method may comprise providing a probability that the is subject highly unlikely, unlikely, likely, or highly likely has IBS. In related embodiments, methods are provided that further include providing a probability that a sample classified as an IBS sample or a non-IBS sample is from a subject with IBS. In certain embodiments, the method may comprise providing a probability that the is sample is from a subject that highly unlikely, unlikely, likely, or highly likely has IBS.

In other embodiments, the methods provided herein further include classifying a diagnosis of IBS as IBS-constipation (IBS-C), IBS-diarrhea (IBS-D), IBS-mixed (IBS-M), IBS-alternating (IBS-A), or post-infectious IBS (IBS-PI). In related embodiments, methods are provided herein to further classify a sample as an IBS-constipation (IBS-C), IBS-diarrhea (IBS-D), IBS-mixed (IBS-M), IBS-alternating (IBS-A), or post-infectious IBS (IBS-PI) sample.

In one embodiment, the present invention provides an assay to aid in the differentiation of IBS-D and IBS-A from IBS-C, the assay comprising: (a) contacting a sample having histamine contained therein under conditions suitable to transform the histamine into a complex comprising histamine and a capture anti-histamine antibody; (b) contacting the complex with an enzyme labeled indicator antibody to transform the complex into a labeled complex; (c) contacting the labeled complex with a substrate for the enzyme; and (d) detecting the presence or level of histamine in the sample.

In some instances, the assay to aid in the differentiation of IBS-D and IBS-A from IBS-C further comprises detecting the presence or level of β-tryptase; and/or prostaglandin $E_2$ ($PGE_2$) in the sample.

In yet other embodiments, methods provided herein further include diagnosing a subject not having IBS as having IBD, as not having IBD, as having celiac disease, as not having celiac disease, as being a healthy subject, or as not having a gastrointestinal disease. In a related embodiment, methods are provided herein that further classify a non-IBS sample as an IBD sample, a non-IBD sample, a healthy sample, a non-gastrointestinal disease sample, a celiac sample, and the like.

In one embodiment, the methods provided herein comprise the use of an algorithm based upon the level of an IBS biomarker. In certain embodiments, the algorithm is further based upon the system profile. In a preferred embodiment, the algorithm comprises a statistical algorithm, for example a learning statistical classifier system. In a more preferred embodiment, the algorithm comprises a combination of at least two learning statistical classifier systems. In a most preferred embodiment, the combination of at least two learning statistical classifier systems comprises a random forest classifier and a neural network classifier.

3. Prostaglandin $E_2$ ($PGE_2$)

In one specific aspect, a method for aiding in the diagnosis of irritable bowel syndrome (IBS) in a subject is provided, the method comprising: (a) contacting a blood or serum sample from the subject with a prostaglandin $E_2$ ($PGE_2$) binding moiety under conditions suitable to transform prostaglandin $E_2$ ($PGE_2$) present in the sample into a complex comprising prostaglandin $E_2$ ($PGE_2$) and the prostaglandin $E_2$ ($PGE_2$) binding moiety; and (b) determining the level of the complex, thereby determining the level of prostaglandin $E_2$ ($PGE_2$) present in the sample. In one embodiment, the method further comprises: (c) comparing the level of prostaglandin $E_2$ ($PGE_2$) present in the sample to a control level, wherein a difference in the level of prostaglandin $E_2$ ($PGE_2$) present in the sample relative to the control level is indicative of an increased likelihood of the subject having IBS.

In a specific embodiment, the present invention provides an assay to aid in the diagnosis of IBS, the assay comprising: (a) contacting a sample having prostaglandin $E_2$ ($PGE_2$) contained therein under conditions suitable to transform the prostaglandin $E_2$ ($PGE_2$) into a complex comprising prostaglandin $E_2$ ($PGE_2$) and a capture anti-tryptase antibody; (b) contacting the complex with an enzyme labeled indicator antibody to transform the complex into a labeled complex; (c) contacting the labeled complex with a substrate for the enzyme; and (d) detecting the presence or level of prostaglandin $E_2$ ($PGE_2$) in the sample.

In certain embodiments, a control level is the level of prostaglandin $E_2$ ($PGE_2$) present in a blood or serum sample from a healthy subject or an average level of prostaglandin $E_2$ ($PGE_2$) present in blood or serum samples from a cohort of healthy subjects. In other embodiments, a control level is the level of prostaglandin $E_2$ ($PGE_2$) present in a blood or serum sample from a non-IBS subject or an average level of prostaglandin $E_2$ ($PGE_2$) present in blood or serum samples from a cohort of non-IBS subjects. In another embodiment, a control level is the level of prostaglandin $E_2$ ($PGE_2$) present in a blood or serum sample from a diseased subject or an average level of prostaglandin $E_2$ ($PGE_2$) present in blood or serum samples from a cohort of diseased subjects. Non-limiting examples of diseased subjects that are useful for determining a control level from include subjects with IBS, subjects with a non-IBS gastrointestinal disease, subjects with inflammatory bowel disease (IBD), subjects with ulcerative colitis (UC), subjects with Crohn's disease (CD), subjects with celiac disease, subjects with gastroesophageal reflux disease (GERD), subjects with cancer, subjects with a cancer of the gastrointestinal tract, subjects with a cancer of the stomach, subjects with a cancer of the small or large bowel, and the like.

In cases where the control level is a level of prostaglandin $E_2$ ($PGE_2$) in a blood or serum sample of a healthy subject or healthy subjects, an increased level of prostaglandin $E_2$ ($PGE_2$) present in a sample from a subject, relative to the control level, is indicative of an increased likelihood of the subject having IBS. Conversely, where the control is a healthy subject or subjects, a similar or reduced level of prostaglandin $E_2$ ($PGE_2$) present in a sample from a subject, relative to the control level, is indicative of an increased likelihood of the subject not having IBS.

In cases where the control level is a level of prostaglandin $E_2$ ($PGE_2$) in a blood or serum sample of a subject or subjects with IBS, a similar or increased level of prostaglandin $E_2$ ($PGE_2$) present in a sample from a subject, relative to the control level, is indicative of an increased likelihood of the subject having IBS. Conversely, where the control is a subject or subjects with IBS, a reduced level of prostaglandin $E_2$ ($PGE_2$) present in a sample from a subject, relative to the control level, is indicative of an increased likelihood of the subject not having IBS.

In certain aspects of the invention, methods are provided for aiding in the diagnosis of irritable bowel syndrome (IBS) in a subject comprising the detection of prostaglandin $E_2$ ($PGE_2$) in a blood or serum sample and at least one additional blood or serum biomarker selected from histamine and β-tryptase. In one embodiment, the method comprises detecting or determining the level of prostaglandin $E_2$ ($PGE_2$) and histamine from a blood or serum sample from a subject. In another embodiment, the method comprises detecting or determining the level of prostaglandin $E_2$ ($PGE_2$) and β-tryptase from a blood or serum sample from a subject. In a third embodiment, the method comprises detecting or determining the level of prostaglandin $E_2$ ($PGE_2$), histamine, and β-tryptase from a blood or serum sample from a subject. Preferably, prostaglandin $E_2$ ($PGE_2$), histamine, and/or β-tryptase are detected from the same blood or serum sample, although in certain instances the biomarkers may be detected in different blood or serum samples taken from the same individual, for example, at the same time or at different times. In certain embodiments, the biomarkers may be detected in separate assays performed with different aliquots of a blood or serum sample from a subject. In other embodiments, the biomarkers may be detected in a single multiplex detection assay, for example, in a Luminex© xMAP© assay.

In yet other aspects of the invention, methods are provided for aiding in the diagnosis of irritable bowel syndrome (IBS) in a subject comprising the detection of prostaglandin $E_2$ ($PGE_2$) in a blood or serum sample and at least one additional biomarker selected from Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), Anti-Human Tissue Transglutaminase IgA (tTG), and a combination thereof. In certain embodiments, at least 2 of the additional biomarkers may be detected. In other embodiments, at least 3, 4, 5, 6, 7, 8, 9, or 10 of the additional biomarkers may be detected.

The sample used for detecting or determining the presence or level of at least one diagnostic marker is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the methods of the present invention further comprise obtaining the sample from the individual prior to detecting or determining the presence or level of at least one diagnostic marker in the sample. In a preferred embodiment, the additional biomarker may be detected from a blood or serum sample. In other embodiments, the additional biomarker may be detected from a stool sample or a biopsy from the bowel of the subject.

In one embodiment, the method comprises detecting or determining the level of prostaglandin $E_2$ ($PGE_2$) from a blood or serum sample and Brain-Derived Neurotropic Factor (BDNF) from a biological sample. In a preferred embodiment, Brain-Derived Neurotropic Factor (BDNF) is detected in a blood or serum sample from the subject. In another preferred embodiment, Brain-Derived Neurotropic Factor (BDNF) is detected in a stool sample or a biopsy from the bowel of the subject. In other embodiments, at least one additional biomarker is also detected.

In one embodiment, the method comprises detecting or determining the level of prostaglandin $E_2$ ($PGE_2$) from a blood or serum sample and Neutrophil Gelatinase-Associated Lipocalin (NGAL) from a biological sample. In a preferred embodiment, Neutrophil Gelatinase-Associated Lipocalin (NGAL) is detected in a blood or serum sample from the subject. In another preferred embodiment, Neutrophil Gelatinase-Associated Lipocalin (NGAL) is detected in a stool sample or a biopsy from the bowel of the subject. In other embodiments, at least one additional biomarker is also detected.

In one embodiment, the method comprises detecting or determining the level of prostaglandin $E_2$ ($PGE_2$) from a blood or serum sample and TNF-related Weak Inducer of Apoptosis (TWEAK) from a biological sample. In a preferred embodiment, TNF-related Weak Inducer of Apoptosis (TWEAK) is detected in a blood or serum sample from the subject. In another preferred embodiment, TNF-related Weak Inducer of Apoptosis (TWEAK) is detected in a stool sample or a biopsy from the bowel of the subject. In other embodiments, at least one additional biomarker is also detected.

In one embodiment, the method comprises detecting or determining the level of prostaglandin $E_2$ ($PGE_2$) from a blood or serum sample and Growth-Related Oncogene Alpha (GRO-α) from a biological sample. In a preferred embodiment, Growth-Related Oncogene Alpha (GRO-α) is detected in a blood or serum sample from the subject. In another preferred embodiment, Growth-Related Oncogene Alpha (GRO-α) is detected in a stool sample or a biopsy from the bowel of the subject. In other embodiments, at least one additional biomarker is also detected.

In one embodiment, the method comprises detecting or determining the level of prostaglandin $E_2$ ($PGE_2$) from a blood or serum sample and Interleukin-1 Beta (IL-1β) from a biological sample. In a preferred embodiment, Interleukin-1 Beta (IL-1β) is detected in a blood or serum sample from the subject. In another preferred embodiment, Interleukin-1 Beta (IL-1β) is detected in a stool sample or a biopsy from the bowel of the subject. In other embodiments, at least one additional biomarker is also detected.

In one embodiment, the method comprises detecting or determining the level of prostaglandin $E_2$ (PGE$_2$) from a blood or serum sample and Tissue Inhibitor of Metalloproteinase-1 (TIMP-1) from a biological sample. In a preferred embodiment, Tissue Inhibitor of Metalloproteinase-1 (TIMP-1) is detected in a blood or serum sample from the subject. In another preferred embodiment, Tissue Inhibitor of Metalloproteinase-1 (TIMP-1) is detected in a stool sample or a biopsy from the bowel of the subject. In other embodiments, at least one additional biomarker is also detected.

In one embodiment, the method comprises detecting or determining the level of prostaglandin $E_2$ (PGE$_2$) from a blood or serum sample and Anti-*Saccharomyces cerevisiae* Antibody (ASCA-IgA) from a biological sample. In a preferred embodiment, Anti-*Saccharomyces cerevisiae* Antibody (ASCA-IgA) is detected in a blood or serum sample from the subject. In another preferred embodiment, Anti-*Saccharomyces cerevisiae* Antibody (ASCA-IgA) is detected in a stool sample or a biopsy from the bowel of the subject. In other embodiments, at least one additional biomarker is also detected.

In one embodiment, the method comprises detecting or determining the level of prostaglandin $E_2$ (PGE$_2$) from a blood or serum sample and Anti-CBir-1 Antibody (CBir1) from a biological sample. In a preferred embodiment, Anti-CBir-1 Antibody (CBir1) is detected in a blood or serum sample from the subject. In another preferred embodiment, Anti-CBir-1 Antibody (CBir1) is detected in a stool sample or a biopsy from the bowel of the subject. In other embodiments, at least one additional biomarker is also detected.

In one embodiment, the method comprises detecting or determining the level of prostaglandin $E_2$ (PGE$_2$) from a blood or serum sample and Anti-Human Neutrophil Cytoplasmic Antibody (ANCA) from a biological sample. In a preferred embodiment, Anti-Human Neutrophil Cytoplasmic Antibody (ANCA) is detected in a blood or serum sample from the subject. In another preferred embodiment, Anti-Human Neutrophil Cytoplasmic Antibody (ANCA) is detected in a stool sample or a biopsy from the bowel of the subject. In other embodiments, at least one additional biomarker is also detected.

In one embodiment, the method comprises detecting or determining the level of prostaglandin $E_2$ (PGE$_2$) from a blood or serum sample and Anti-Human Tissue Transglutaminase IgA (tTG) from a biological sample. In a preferred embodiment, Anti-Human Tissue Transglutaminase IgA (tTG) is detected in a blood or serum sample from the subject. In another preferred embodiment, Anti-Human Tissue Transglutaminase IgA (tTG) is detected in a stool sample or a biopsy from the bowel of the subject. In other embodiments, at least one additional biomarker is also detected.

In one embodiment, the method comprises detecting or determining the level of prostaglandin $E_2$ (PGE$_2$) from a blood or serum sample and all of Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), and Anti-Human Tissue Transglutaminase IgA (tTG) from a blood or serum sample, a stool sample, or a biopsy from the bowel of the subject.

In certain embodiments, the presence or level of at least one diagnostic marker is determined using an assay such as a hybridization assay or an amplification-based assay. Examples of hybridization assays suitable for use in the methods of the present invention include, but are not limited to, Northern blotting, dot blotting, RNase protection, and a combination thereof. A non-limiting example of an amplification-based assay suitable for use in the methods of the present invention includes a reverse transcriptase-polymerase chain reaction (RT-PCR).

In certain other embodiments, the presence or level of at least one diagnostic marker is determined using an immunoassay or an immunohistochemical assay. A non-limiting example of an immunoassay suitable for use in the methods of the present invention includes an enzyme-linked immunosorbent assay (ELISA). Examples of immunohistochemical assays suitable for use in the methods of the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays.

In some embodiments, the methods provided herein further include the step of determining a symptom profile for the subject, wherein the symptom profile is determined by identifying the presence or severity of at least one symptom in the subject. In a preferred embodiment, the method comprises: (d) determining a symptom profile for the subject, wherein the symptom profile is determined by identifying the presence or severity of at least one symptom in the subject; and (e) diagnosing the subject as having IBS or not having IBS using an algorithm based upon the level of an IBS biomarker and the system profile. In a preferred embodiment, the method for aiding in the diagnosis of irritable bowel syndrome (IBS) in a subject comprises determining a diagnostic marker profile, for example for prostaglandin $E_2$ (PGE$_2$) or a combination thereof as described herein, optionally in combination with a symptom profile, wherein the symptom profile is determined by identifying the presence or severity of at least one symptom in the individual; and classifying the sample as an IBS sample or non-IBS sample using an algorithm based upon the diagnostic marker profile and the symptom profile.

The symptom profile is typically determined by identifying the presence or severity of at least one symptom selected from the group consisting of chest pain, chest discomfort, heartburn, uncomfortable fullness after having a regular-sized meal, inability to finish a regular-sized meal, abdominal pain, abdominal discomfort, constipation, diarrhea, bloating, abdominal distension, negative thoughts or feelings associated with having pain or discomfort, and combinations thereof.

In preferred embodiments, the presence or severity of 1, 2, 3, 4, 5, 6, 7, 8, 9, 10, or more of the symptoms described herein is identified to generate a symptom profile that is useful for predicting IBS. In certain instances, a questionnaire or other form of written, verbal, or telephone survey is used to produce the symptom profile. The questionnaire or survey typically comprises a standardized set of questions and answers for the purpose of gathering information from respondents regarding their current and/or recent IBS-related symptoms.

In some embodiments, the symptom profile is produced by compiling and/or analyzing all or a subset of the answers to the questions set forth in the questionnaire or survey. In other embodiments, the symptom profile is produced based upon the individual's response to the following question: "Are you currently experiencing any symptoms?" The symptom profile generated in accordance with either of these embodiments can be used in combination with a diagnostic marker profile in the algorithmic-based methods described herein to improve the accuracy of predicting IBS.

In some embodiments, the methods provided herein further include providing a probability that a subject has IBS. In certain embodiments, the method may comprise providing a probability that the is subject highly unlikely, unlikely, likely, or highly likely has IBS. In related embodiments, methods are provided that further include providing a probability that a sample classified as an IBS sample or a non-IBS sample is from a subject with IBS. In certain embodiments, the method may comprise providing a probability that the is sample is from a subject that highly unlikely, unlikely, likely, or highly likely has IBS.

In other embodiments, the methods provided herein further include classifying a diagnosis of IBS as IBS-constipation (IBS-C), IBS-diarrhea (IBS-D), IBS-mixed (IBS-M), IBS-alternating (IBS-A), or post-infectious IBS (IBS-PI). In related embodiments, methods are provided herein to further classify a sample as an IBS-constipation (IBS-C), IBS-diarrhea (IBS-D), IBS-mixed (IBS-M), IBS-alternating (IBS-A), or post-infectious IBS (IBS-PI) sample.

In one embodiment, the present invention provides an assay to aid in the differentiation of IBS-D and IBS-A from IBS-C, the assay comprising: (a) contacting a sample having prostaglandin $E_2$ ($PGE_2$) contained therein under conditions suitable to transform the prostaglandin $E_2$ ($PGE_2$) into a complex comprising prostaglandin $E_2$ ($PGE_2$) and a capture anti-prostaglandin $E_2$ ($PGE_2$) antibody; (b) contacting the complex with an enzyme labeled indicator antibody to transform the complex into a labeled complex; (c) contacting the labeled complex with a substrate for the enzyme; and (d) detecting the presence or level of prostaglandin $E_2$ ($PGE_2$) in the sample.

In some instances, the assay to aid in the differentiation of IBS-D and IBS-A from IBS-C further comprises detecting the presence or level of β-tryptase; and/or histamine in the sample.

In yet other embodiments, methods provided herein further include diagnosing a subject not having IBS as having IBD, as not having IBD, as having celiac disease, as not having celiac disease, as being a healthy subject, or as not having a gastrointestinal disease. In a related embodiment, methods are provided herein that further classify a non-IBS sample as an IBD sample, a non-IBD sample, a healthy sample, a non-gastrointestinal disease sample, a celiac sample, and the like.

In one embodiment, the methods provided herein comprise the use of an algorithm based upon the level of an IBS biomarker. In certain embodiments, the algorithm is further based upon the system profile. In a preferred embodiment, the algorithm comprises a statistical algorithm, for example a learning statistical classifier system. In a more preferred embodiment, the algorithm comprises a combination of at least two learning statistical classifier systems. In a most preferred embodiment, the combination of at least two learning statistical classifier systems comprises a random forest classifier and a neural network classifier.

4. Symptom Profiles

In some embodiments, the method for aiding in the diagnosis of IBS comprises determining a diagnostic marker profile optionally in combination with a symptom profile, wherein the symptom profile is determined by identifying the presence or severity of at least one symptom in the individual; and classifying the sample as an IBS sample or non-IBS sample using an algorithm based upon the diagnostic marker profile and the symptom profile. One skilled in the art will appreciate that the diagnostic marker profile and the symptom profile can be determined simultaneously or sequentially in any order.

The symptom profile is typically determined by identifying the presence or severity of at least one symptom selected from the group consisting of chest pain, chest discomfort, heartburn, uncomfortable fullness after having a regular-sized meal, inability to finish a regular-sized meal, abdominal pain, abdominal discomfort, constipation, diarrhea, bloating, abdominal distension, negative thoughts or feelings associated with having pain or discomfort, and combinations thereof.

In preferred embodiments, the presence or severity of 1, 2, 3, 4, 5, 6, 7, 8, 9, 10, or more of the symptoms described herein is identified to generate a symptom profile that is useful for predicting IBS. In certain instances, a questionnaire or other form of written, verbal, or telephone survey is used to produce the symptom profile. The questionnaire or survey typically comprises a standardized set of questions and answers for the purpose of gathering information from respondents regarding their current and/or recent IBS-related symptoms. For instance, Example 13 provides exemplary questions that can be included in a questionnaire for identifying the presence or severity of one or more IBS-related symptoms in the individual.

In certain embodiments, the symptom profile is produced by compiling and/or analyzing all or a subset of the answers to the questions set forth in the questionnaire or survey. In certain other embodiments, the symptom profile is produced based upon the individual's response to the following question: "Are you currently experiencing any symptoms?" The symptom profile generated in accordance with either of these embodiments can be used in combination with a diagnostic marker profile in the algorithmic-based methods described herein to improve the accuracy of predicting IBS.

5. Use of Statistical Algorithms

In some embodiments, methods for aiding in the diagnosis of irritable bowel syndrome (IBS) in a subject is based upon the diagnostic marker profile, alone or in combination with a symptom profile, in conjunction with a statistical algorithm. In certain instances, the statistical algorithm is a learning statistical classifier system. The learning statistical classifier system can be selected from the group consisting of a random forest (RF), classification and regression tree (C&RT), boosted tree, neural network (NN), support vector machine (SVM), general chi-squared automatic interaction detector model, interactive tree, multiadaptive regression spline, machine learning classifier, and combinations thereof. Preferably, the learning statistical classifier system is a tree-based statistical algorithm (e.g., RF, C&RT, etc.) and/or a NN (e.g., artificial NN, etc.). Additional examples of learning statistical classifier systems suitable for use in the present invention are described in U.S. patent application Ser. No. 11/368,285. In certain embodiments, the methods comprise classifying a sample from the subject as an IBS sample or non-IBS sample.

In certain instances, the statistical algorithm is a single learning statistical classifier system. Preferably, the single learning statistical classifier system comprises a tree-based statistical algorithm such as a RF or C&RT. As a non-limiting example, a single learning statistical classifier system can be used to classify the sample as an IBS sample or non-IBS sample based upon a prediction or probability value and the presence or level of at least one diagnostic marker (i.e., diagnostic marker profile), alone or in combination with the presence or severity of at least one symptom (i.e., symptom profile). The use of a single learning statistical classifier system typically classifies the sample as an IBS sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. As such, the classification of a sample as an IBS sample or non-IBS sample is useful for aiding in the diagnosis of IBS in a subject.

In certain other instances, the statistical algorithm is a combination of at least two learning statistical classifier systems. Preferably, the combination of learning statistical classifier systems comprises a RF and a NN, e.g., used in tandem or parallel. As a non-limiting example, a RF can first be used to generate a prediction or probability value based upon the diagnostic marker profile, alone or in combination with a symptom profile, and a NN can then be used to classify the sample as an IBS sample or non-IBS sample based upon the prediction or probability value and the same or different diagnostic marker profile or combination of profiles. Advantageously, the hybrid RF/NN learning statistical classifier system of the present invention classifies the sample as an IBS sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In a particularly preferred embodiment, the statistical algorithm is a random forest classifier or a combination of a random forest classifier and a neural network classifier.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

In certain other embodiments, the methods of the present invention further comprise sending the IBS classification results to a clinician, e.g., a gastroenterologist or a general practitioner. In another embodiment, the methods of the present invention provide a diagnosis in the form of a probability that the individual has IBS. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having IBS. In yet another embodiment, the methods of the present invention further provide a prognosis of IBS in the individual. For example, the prognosis can be surgery, development of a category or clinical subtype of IBS, development of one or more symptoms, or recovery from the disease.

B. Assays and Kits

In one aspect, the present invention provides an assay for the detection of $\beta$-tryptase in a blood or serum sample, the method comprising the steps of: (a) coating a solid phase surface with a first anti-$\beta$-tryptase capture antibody; (b) contacting the solid phase surface with a blood or serum sample under conditions suitable to transform $\beta$-tryptase present in the sample into a complex comprising $\beta$-tryptase and the anti-$\beta$-tryptase capture antibody; (c) contacting the $\beta$-tryptase and the anti-$\beta$-tryptase complex with a second detecting antibody under conditions suitable to form a ternary complex; and (d) contacting the ternary complex with a luminescent or chemiluminescent substrate.

In one embodiment, the detecting antibody is conjugated to alkaline phosphatase. In other embodiments, the detecting antibody is not conjugated to an enzyme and the method further comprises the steps of (i) contacting the ternary complex with a third antibody conjugated to alkaline phosphatase under conditions suitable to form a quaternary complex and (ii) contacting the quaternary complex with a luminescent or chemiluminescent substrate.

Any suitable antibody pair may be used for the capture and detecting antibodies in a sandwich ELISA. One of skill in the art will know and appreciate how to select an appropriate antibody pair for the assay. Generally, two antibodies are selected that bind to the target of interest, e.g., $\beta$-tryptase, at different epitopes such that the binding of the first (capture) antibody does not interfere with the second (detecting) antibody. In certain embodiments, the detecting antibody will be conjugated to an enzyme, for example, alkaline phophatase, to aid in the detection of the complex. In other embodiments, a secondary antibody conjugated to an enzyme (e.g., alkaline phophatase), which binds to the detecting antibody, may be used in the assay.

Generally, the complex will be detected by the use of a luminescent substrate, for example, a luminescent substrate found in a kit such as Ultra LITE™ (NAG Research Laboratories); SensoLyte® (AnaSpec); SuperSignal ELISA Femto Maximum Sensitivity Substrate (Thermo Scientific); SuperSignal ELISA Pico Chemiluminescent Substrate (Thermo Scientific); or CPSD (disodium 3-(4-methoxyspiro{1,2-dioxetane-3,2'-(5'-chloro)tricyclo[3.3.1.13,7]decan}-4-yl)phenyl phosphate; Tropix, Inc).

In a preferred embodiment, an assay for detecting the presence or level of $\beta$-tryptase comprises a sandwich ELISA that relies on the use of an alkaline phosphatase conjugated anti-tryptase antibody as the detecting antibody and a CPSD containing luminescent substrate to enhance the assay sensitivity. The CPSD substrate can be found in chemiluminescent detection systems, such as the ELISA-Light™ System (Applied Biosystems). In a particularly preferred embodiment, the detection antibody used in the sandwich ELISA is the anti-tryptase antibody G3 (sc-33676; Santa Cruz Biotechnology, Inc.; Santa Cruz, Calif.).

In a preferred embodiment of the assay, the detection limit of $\beta$-tryptase present in a blood or serum sample is less than about 500 pg/ml. In certain embodiments, the detection limit of $\beta$-tryptase present in a blood or serum sample is less than about 500 pg/ml, or less than about 400 pg/ml, 300 pg/ml, 250 pg/ml, 200 pg/ml, 150 pg/ml, 100 pg/ml, 75 pg/ml, 50 pg/ml, 40 pg/ml, 30 pg/ml, 25 pg/ml, 20 pg/ml, 15 pg/ml, or less than about 10 pg/ml. In a preferred embodiment, the detection limit of $\beta$-tryptase present in a blood or serum sample is less than about 200 pg/ml. In a more preferred embodiment, the detection limit of $\beta$-tryptase present in a blood or serum sample is less than about 100 pg/ml. In a more preferred embodiment, the detection limit of $\beta$-tryptase present in a blood or serum sample is less than about 50 pg/ml. In a most preferred embodiment, the detection limit of $\beta$-tryptase present in a blood or serum sample is less than about 25 pg/ml.

In another aspect, the present invention provides an assay to aid in the diagnosis of IBS, the assay comprising: (a) contacting a sample having $\beta$-tryptase under conditions suitable to transform the $\beta$-tryptase into a complex comprising $\beta$-tryptase and a capture anti-tryptase antibody; (b) contacting the complex with an enzyme-labeled indicator antibody to transform the complex into a labeled complex; (c) contacting the labeled complex with a substrate for the enzyme; and (d) detecting the presence or level of $\beta$-tryptase in the sample.

In one embodiment of an assay to aid in the diagnosis of IBS, the sample is human serum.

In another embodiment of an assay to aid in the diagnosis of IBS, the sample is obtained from a subject suspected of having IBS.

In another embodiment of an assay to aid in the diagnosis of IBS, a higher level of β-tryptase in the sample relative to healthy controls is indicative of an increased likelihood of the subject having IBS.

In another embodiment of an assay to aid in the diagnosis of IBS, the assay is an enzyme-linked immunosorbent assay (ELISA).

In another embodiment of an assay to aid in the diagnosis of IBS, detecting the presence or level of β-tryptase in the sample comprises the use of a detection device.

In another embodiment of an assay to aid in the diagnosis of IBS, the detection device comprises a luminescence plate reader.

In another embodiment of an assay to aid in the diagnosis of IBS, the detection device comprises a spectrophotometer.

In another embodiment of an assay to aid in the diagnosis of IBS, the assay further comprises detecting the presence or level of prostaglandin E2 ($PGE_2$) and/or histamine in the sample.

In another aspect, the present invention provides an assay to aid in the differentiation of clinical subtypes of IBS, the assay comprising: (a) contacting a sample having β-tryptase under conditions suitable to transform the β-tryptase into a complex comprising β-tryptase and a capture anti-tryptase antibody; (b) contacting the complex with an enzyme-labeled indicator antibody to transform the complex into a labeled complex; (c) contacting the labeled complex with a substrate for the enzyme; and (d) detecting the presence or level of β-tryptase in the sample.

In one embodiment of an assay to aid in the differentiation of clinical subtypes of IBS, the assay aids in the differentiation of IBS-D and IBS-A from IBS-C.

In another embodiment of an assay to aid in the differentiation of clinical subtypes of IBS, the sample is human serum.

In another embodiment of an assay to aid in the differentiation of clinical subtypes of IBS, the assay is an enzyme-linked immunosorbent assay (ELISA).

In another embodiment of an assay to aid in the differentiation of clinical subtypes of IBS, detecting the presence or level of β-tryptase in the sample comprises the use of a detection device.

In another embodiment of an assay to aid in the differentiation of clinical subtypes of IBS, the assay further comprises detecting the presence or level of prostaglandin E2 ($PGE_2$) and/or histamine in the sample.

In yet another aspect, the present invention provides an assay to aid in the diagnosis of IBS, the assay comprising: (a) contacting a sample having β-tryptase, prostaglandin $E_2$, and/or histamine under conditions suitable to transform the β-tryptase, prostaglandin $E_2$, and/or histamine into a complex comprising β-tryptase, prostaglandin $E_2$, and/or histamine and a capture anti-β-tryptase, anti-prostaglandin $E_2$, and/or anti-histamine antibody; (b) contacting the complex with an enzyme-labeled indicator antibody to transform the complex into a labeled complex; (c) contacting the labeled complex with a substrate for the enzyme; and (d) detecting the presence or level of β-tryptase, prostaglandin $E_2$, and/or histamine in the sample.

In certain embodiments, the assays provided herein may further comprise detection of the presence or level of at least one additional biomarker selected from the group consisting of Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), Anti-Human Tissue Transglutaminase IgA (tTG), and a combination thereof.

In yet other embodiments, the assays provided herein may further comprise detection of the presence or level of at least one additional biomarker selected from the group consisting of a cytokine (e.g., IL-8, IL-1β, TWEAK, leptin, OPG, MIP-3β, GROα, CXCL4/PF-4, and/or CXCL7/NAP-2), growth factor (e.g., EGF, VEGF, PEDF, BDNF, and/or SDGF), anti-neutrophil antibody (e.g., ANCA, pANCA, cANCA, NSNA, and/or SAPPA), ASCA (e.g., ASCA-IgA, ASCA-IgG, and/or ASCA-IgM), antimicrobial antibody (e.g., anti-OmpC antibody, anti-flagellin antibody, and/or anti-I2 antibody), lactoferrin, anti-tTG antibody, lipocalin (e.g., NGAL, NGAL/MMP-9 complex), MMP (e.g., MMP-9), TIMP (e.g., TIMP-1), alpha-globulin (e.g., alpha-2-macroglobulin, haptoglobin, and/or orosomucoid), actin-severing protein (e.g., gelsolin), S100 protein (e.g., calgranulin), fibrinopeptide (e.g., FIBA), CGRP, tachykinin (e.g., Substance P), ghrelin, neurotensin, corticotropin-releasing hormone, and combinations thereof. In yet other embodiments, the presence or level of other diagnostic markers such as, for example, anti-lactoferrin antibody, L-selectin/CD62L, elastase, C-reactive protein (CRP), calprotectin, anti-U1-70 kDa autoantibody, zona occludens 1 (ZO-1), vasoactive intestinal peptide (VIP), serum amyloid A, gastrin, and a combination thereof may also be detected.

In certain embodiments, the assays provided may comprise the detection of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more of the biomarkers described herein.

In another aspect, kits are provided for aiding in the diagnosis of IBS in a subject, or for classifying a sample as an IBS sample or a non-IBS sample. In certain embodiments, The kits provided herein contain a binding moiety for detecting the presence or level of an IBS biomarker selected from β-tryptase, prostaglandin $E_2$, and/or histamine.

In other embodiments, the kit will also contain at least one binding moiety for an additional biomarker selected from the group consisting of Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), Anti-Human Tissue Transglutaminase IgA (tTG), and a combination thereof.

In yet other embodiments, a kit will contain at least one binding moiety for an additional biomarker selected from the group consisting of a cytokine (e.g., IL-8, IL-1β, TWEAK, leptin, OPG, MIP-3β, GROα, CXCL4/PF-4, and/or CXCL7/NAP-2), growth factor (e.g., EGF, VEGF, PEDF, BDNF, and/or SDGF), anti-neutrophil antibody (e.g., ANCA, pANCA, cANCA, NSNA, and/or SAPPA), ASCA (e.g., ASCA-IgA, ASCA-IgG, and/or ASCA-IgM), antimicrobial antibody (e.g., anti-OmpC antibody, anti-flagellin antibody, and/or anti-I2 antibody), lactoferrin, anti-tTG antibody, lipocalin (e.g., NGAL, NGAL/MMP-9 complex), MMP (e.g., MMP-9), TIMP (e.g., TIMP-1), alpha-globulin (e.g., alpha-2-macroglobulin, haptoglobin, and/or orosomucoid), actin-severing protein (e.g., gelsolin), S100 protein (e.g., calgranulin), fibrinopeptide (e.g., FIBA), CGRP, tachykinin (e.g., Substance P), ghrelin, neurotensin, corticotropin-releasing hormone, anti-lactoferrin antibody, L-selectin/CD62L, elastase, C-reactive protein (CRP), calprotectin, anti-U1-70 kDa autoantibody, zona occludens 1 (ZO-1), vasoactive intestinal peptide (VIP), serum amyloid A, gastrin, and combinations thereof.

In certain embodiments, the kits provided may contain a binding moiety for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more of the biomarkers described herein.

In a preferred embodiment, a kit is provided for detecting the presence or level of β-tryptase in a blood or serum sample. In one embodiment, the kit contains a first capture antibody, which is optionally attached to a solid surface, and a second detection antibody that binds to a different epitope on β-tryptase than the capture antibody. In certain embodiments, the detection antibody will be conjugated to alkaline phosphatase. In other embodiments, the detection antibody will not be conjugated to an enzyme, i.e., alkaline phophatase. In a preferred embodiment, the detection antibody is the anti-tryptase antibody G3 (sc-33676; Santa Cruz Biotechnology, Inc.; Santa Cruz, Calif.). In a more preferred embodiment, the anti-tryptase antibody G3 is further alkaline phosphatase conjugated. In certain embodiments, wherein the detection antibody is not enzyme-conjugated, the kit may further comprise a third antibody specific for the detection antibody, the third antibody being conjugated to an enzyme, e.g., alkaline phophatase.

In certain embodiments, the kit will also contain a luminescent or chemiluminescent substrate, for example, a luminescent substrate as found in Ultra LITE™ (NAG Research Laboratories); SensoLyte® (AnaSpec); SuperSignal ELISA Femto Maximum Sensitivity Substrate (Thermo Scientific); SuperSignal ELISA Pico Chemiluminescent Substrate (Thermo Scientific); or CPSD (disodium 3-(4-methoxyspiro{1,2-dioxetane-3,2'-(5'-chloro)tricyclo[3.3.1.13,7]decan}-4-yl)phenyl phosphate; Tropix, Inc). In a preferred embodiment, the luminescent substrate is CPSD (disodium 3-(4-methoxyspiro{1,2-dioxetane-3,2'-(5'-chloro)tricyclo [3.3.1.13,7]decan}-4-yl)phenyl phosphate.

In certain embodiments, the kit for detecting the presence or level of β-tryptase is suitable for detecting β-tryptase present in a blood or serum sample at a concentration of less than about 500 pg/ml. In certain embodiments, the kit is suitable for detecting β-tryptase present in a blood or serum sample at a concentration of less than about 500 pg/ml, or less than about 400 pg/ml, 300 pg/ml, 250 pg/ml, 200 pg/ml, 150 pg/ml, 100 pg/ml, 75 pg/ml, 50 pg/ml, 40 pg/ml, 30 pg/ml, 25 pg/ml, 20 pg/ml, 15 pg/ml, or less than about 10 pg/ml. In a preferred embodiment, the kit is suitable for detecting β-tryptase present in a blood or serum sample at a concentration of less than about 200 pg/ml. In a more preferred embodiment, the kit is suitable for detecting β-tryptase present in a blood or serum sample at a concentration of less than about 100 pg/ml. In a more preferred embodiment, the kit is suitable for detecting β-tryptase present in a blood or serum sample at a concentration of less than about 50 pg/ml. In a most preferred embodiment, the kit is suitable for detecting β-tryptase present in a blood or serum sample at a concentration of less than about 25 pg/ml.

C. Methods for Monitoring and Assigning Therapy

In some embodiments, the diagnosis of an individual as having IBS is followed by administering to the individual a therapeutically effective amount of a drug useful for treating one or more symptoms associated with IBS. Suitable IBS drugs include, but are not limited to, serotonergic agents, antidepressants, chloride channel activators, chloride channel blockers, guanylate cyclase agonists, antibiotics, opioid agonists, neurokinin antagonists, antispasmodic or anticholinergic agents, belladonna alkaloids, barbiturates, GLP-1 analogs, CRF antagonists, probiotics, free bases thereof, pharmaceutically acceptable salts thereof, derivatives thereof, analogs thereof, and combinations thereof. Other IBS drugs include bulking agents, dopamine antagonists, carminatives, tranquilizers, dextofisopam, phenyloin, timolol, and diltiazem. Additionally, amino acids like glutamine and glutamic acid which regulate intestinal permeability by affecting neuronal or glial cell signaling can be administered to treat patients with IBS.

In other embodiments, the methods of the present invention further comprise classifying an IBS sample or a diagnosis of IBS as an IBS-constipation (IBS-C), IBS-diarrhea (IBS-D), IBS-mixed (IBS-M), IBS-alternating (IBS-A), or post-infectious IBS (IBS-PI) sample or diagnosis. In certain instances, the classification of the IBS sample or diagnosis into a category, form, or clinical subtype of IBS is based upon the presence or level of at least one, two, three, four, five, six, seven, eight, nine, ten, or more classification markers provided herein. Preferably, at least one form of IBS is distinguished from at least one other form of IBS based upon the presence or level of leptin, β-tryptase, prostaglandin $E_2$, and/or histamine. In certain instances, the methods of the present invention can be used to differentiate an IBS-C sample from an IBS-A and/or IBS-D sample in an individual previously identified as having IBS. In certain other instances, the methods of the present invention can be used to classify a sample from an individual not previously diagnosed with IBS as an IBS-A sample, IBS-C sample, IBS-D sample, or non-IBS sample.

In certain embodiments, the methods further comprise sending the results from the classification to a clinician. In certain other embodiments, the methods further provide a diagnosis in the form of a probability that the individual has IBS-A, IBS-C, IBS-D, IBS-M, or IBS-PI. The methods of the present invention can further comprise administering to the individual a therapeutically effective amount of a drug useful for treating IBS-A, IBS-C, IBS-D, IBS-M, or IBS-PI. Suitable drugs include, but are not limited to, tegaserod (Zelnorm™), alosetron (Lotronex®), lubiprostone (Amitiza™), rifamixin (Xifaxan™), MD-1100, probiotics, and a combination thereof.

In instances where the sample is classified as an IBS-A or IBS-C sample and/or the individual is diagnosed with IBS-A or IBS-C, a therapeutically effective dose of tegaserod or other 5-HT$_4$ agonist (e.g., mosapride, renzapride, AG1-001, etc.) can be administered to the individual. In some instances, when the sample is classified as IBS-C and/or the individual is diagnosed with IBS-C, a therapeutically effective amount of lubiprostone or other chloride channel activator, rifamixin or other antibiotic capable of controlling intestinal bacterial overgrowth, MD-1100 or other guanylate cyclase agonist, asimadoline or other opioid agonist, or talnetant or other neurokinin antagonist can be administered to the individual. In other instances, when the sample is classified as IBS-D and/or the individual is diagnosed with IBS-D, a therapeutically effective amount of alosetron or other 5-HT$_3$ antagonist (e.g., ramosetron, DDP-225, etc.), crofelemer or other chloride channel blocker, talnetant or other neurokinin antagonist (e.g., saredutant, etc.), or an antidepressant such as a tricyclic antidepressant can be administered to the individual.

In yet another aspect, the present invention provides a method for monitoring the progression or regression of IBS in an individual, the method comprising: (a) determining a diagnostic marker profile by detecting the presence or level of at least one diagnostic marker in the sample; and (b) determining the presence or severity of IBS in the individual using an algorithm based upon the diagnostic marker profile.

In one embodiment, the method of monitoring the progression or regression of IBS comprises determining a diagnostic marker profile optionally in combination with a symptom profile, wherein the symptom profile is determined by identifying the presence or severity of at least one symptom in the individual; and determining the presence or severity of IBS in the individual using an algorithm based upon the diagnostic marker profile and the symptom profile.

In a related aspect, the present invention provides a method for monitoring drug efficacy in an individual receiving a drug useful for treating IBS, the method comprising: (a) determining a diagnostic marker profile by detecting the presence or level of at least one diagnostic marker in the sample; and (b) determining the effectiveness of the drug using an algorithm based upon the diagnostic marker profile.

In one embodiment, the method of monitoring IBS drug efficacy comprises determining a diagnostic marker profile optionally in combination with a symptom profile, wherein the symptom profile is determined by identifying the presence or severity of at least one symptom in the individual; and determining the effectiveness of the drug using an algorithm based upon the diagnostic marker profile and the symptom profile.

In one embodiment, the present invention provides a method for monitoring the progression or regression of irritable bowel syndrome (IBS) in a subject, the method comprising: (a) contacting a first blood or serum sample taken from the subject at a first time with a β-tryptase, prostaglandin $E_2$, and/or histamine binding moiety under conditions suitable to transform β-tryptase, prostaglandin $E_2$, and/or histamine present in the sample into a complex comprising β-tryptase, prostaglandin $E_2$, and/or histamine and the β-tryptase, prostaglandin $E_2$, and/or histamine binding moiety; (b) determining the level of the complex, thereby determining the level of β-tryptase, prostaglandin $E_2$, and/or histamine present in the first sample; (c) contacting a second blood or serum sample taken from the subject at a second time with a β-tryptase, prostaglandin $E_2$, and/or histamine binding moiety under conditions suitable to transform β-tryptase, prostaglandin $E_2$, and/or histamine present in the sample into a complex comprising β-tryptase, prostaglandin $E_2$, and/or histamine and the β-tryptase, prostaglandin $E_2$, and/or histamine binding moiety; (d) determining the level of the complex, thereby determining the level of β-tryptase, prostaglandin $E_2$, and/or histamine present in the second sample; and (e) comparing the level of β-tryptase, prostaglandin $E_2$, and/or histamine present in the first sample to the level of β-tryptase, prostaglandin $E_2$, and/or histamine present in the second sample, wherein a higher level of β-tryptase, prostaglandin $E_2$, and/or histamine in the second sample relative to the first sample is indicative of the progression of IBS in the subject and a lower level of β-tryptase, prostaglandin $E_2$, and/or histamine in the second sample relative to the first sample is indicative of the regression of IBS in the subject.

In certain embodiments of the methods of monitoring and assigning therapy, the method further comprises detecting the presence of level of at least one additional biomarker selected from the group consisting of Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), Anti-Human Tissue Transglutaminase IgA (tTG), and a combination thereof. In certain embodiments, the method comprises detecting the presence or level of at least two, three, four, five, six, seven, eight, nine, or all ten of the additional biomarkers provided above.

In yet other embodiments, the method my further comprises detecting the presence of level of at least one biomarker selected from the group consisting of a cytokine (e.g., IL-8, IL-1β, TWEAK, leptin, OPG, MIP-3β, GROα, CXCL4/PF-4, and/or CXCL7/NAP-2), growth factor (e.g., EGF, VEGF, PEDF, BDNF, and/or SDGF), anti-neutrophil antibody (e.g., ANCA, pANCA, cANCA, NSNA, and/or SAPPA), ASCA (e.g., ASCA-IgA, ASCA-IgG, and/or ASCA-IgM), antimicrobial antibody (e.g., anti-OmpC antibody, anti-flagellin antibody, and/or anti-I2 antibody), lactoferrin, anti-tTG antibody, lipocalin (e.g., NGAL, NGAL/MMP-9 complex), MMP (e.g., MMP-9), TIMP (e.g., TIMP-1), alpha-globulin (e.g., alpha-2-macroglobulin, haptoglobin, and/or orosomucoid), actin-severing protein (e.g., gelsolin), S100 protein (e.g., calgranulin), fibrinopeptide (e.g., FIBA), CGRP, tachykinin (e.g., Substance P), ghrelin, neurotensin, corticotropin-releasing hormone, and combinations thereof. In yet other embodiments, the presence or level of other diagnostic markers such as, for example, anti-lactoferrin antibody, L-selectin/CD62L, elastase, C-reactive protein (CRP), calprotectin, anti-U1-70 kDa autoantibody, zona occludens 1 (ZO-1), vasoactive intestinal peptide (VIP), serum amyloid A, gastrin, and a combination thereof may also be detected.

In some embodiments, a panel for measuring one or more of the diagnostic markers described above may be constructed and used for determining the presence or severity of IBS or for determining the effectiveness of an IBS drug. One skilled in the art will appreciate that the presence or level of a plurality of diagnostic markers can be determined simultaneously or sequentially, using, for example, an aliquot or dilution of the individual's sample. As described above, the level of a particular diagnostic marker in the individual's sample is generally considered to be elevated when it is at least about 10%, 15%, 20%, 25%, 50%, 75%, 100%, 125%, 150%, 175%, 200%, 250%, 300%, 350%, 400%, 450%, 500%, 600%, 700%, 800%, 900%, or 1000% greater than the level of the same marker in a comparative sample or population of samples (e.g., greater than a median level). Similarly, the level of a particular diagnostic marker in the individual's sample is typically considered to be lowered when it is at least about 5%, 10%, 15%, 20%, 25%, 30%, 35%, 40%, 45%, 50%, 55%, 60%, 65%, 70%, 75%, 80%, 85%, 90%, or 95% less than the level of the same marker in a comparative sample or population of samples (e.g., less than a median level).

In certain embodiments, the method of monitoring the progression or regression of IBS comprises determining a diagnostic marker profile optionally in combination with a symptom profile, wherein the symptom profile is determined by identifying the presence or severity of at least one symptom in the individual; and determining the presence or severity of IBS in the individual using an algorithm based upon the diagnostic marker profile and the symptom profile. In certain other embodiments, the method of monitoring IBS drug efficacy comprises determining a diagnostic marker profile optionally in combination with a symptom profile, wherein the symptom profile is determined by identifying the presence or severity of at least one symptom in the individual; and determining the effectiveness of the drug using an algorithm based upon the diagnostic marker profile and the symptom profile. One skilled in the art will appreciate that the diagnostic marker profile and the symptom profile can be determined simultaneously or sequentially in any order.

In some embodiments, determining the presence or severity of IBS or the effectiveness of an IBS drug is based upon the diagnostic marker profile, alone or in combination with a symptom profile, in conjunction with a statistical algorithm. In certain instances, the statistical algorithm is a learning statistical classifier system. The learning statistical classifier system comprises any of the learning statistical classifier systems described herein.

In certain embodiments, the methods of the present invention can further comprise comparing the presence or severity of IBS in the individual determined in step (b) to the presence or severity of IBS in the individual at an earlier time. As a non-limiting example, the presence or severity of IBS determined for an individual receiving an IBS drug can be compared to the presence or severity of IBS determined for the same individual before initiation of use of the IBS drug or at an earlier time in therapy. In certain other embodiments, the methods of the present invention can comprise determining the effectiveness of the IBS drug by comparing the effectiveness of the IBS drug determined in step (b) to the effectiveness of the IBS drug in the individual at an earlier time in therapy. In additional embodiments, the methods can further comprise sending the IBS monitoring results to a clinician, e.g., a gastroenterologist or a general practitioner.

D. Computer Readable Medium and Systems for Classifying Samples

In one aspect, the present invention provides a computer-readable medium comprising code for controlling one or more processors to classify whether a serum or blood sample from an subject is associated with irritable bowel syndrome (IBS), the code comprising instructions to apply a statistical process to a data set comprising a diagnostic marker profile to produce a statistically derived decision classifying the sample as an IBS sample or non-IBS sample based upon the diagnostic marker profile, wherein the diagnostic marker profile indicates the level of at least one diagnostic marker selected from the group consisting of β-tryptase, histamine, prostaglandin $E_2$ ($PGE_2$), and a combination thereof.

In other embodiments, the computer-readable medium for ruling in IBS comprises instructions to apply a statistical process to a data set comprising a diagnostic marker profile optionally in combination with a symptom profile which indicates the presence or severity of at least one symptom in the individual to produce a statistically derived decision classifying the sample as an IBS sample or non-IBS sample based upon the diagnostic marker profile and the symptom profile. One skilled in the art will appreciate that the statistical process can be applied to the diagnostic marker profile and the symptom profile simultaneously or sequentially in any order.

In a specific embodiment, the present invention provides a computer-readable medium including code for controlling one or more processors to classify whether a sample from an individual is associated with IBS, the code comprising instructions to apply a statistical process to a data set comprising a diagnostic marker profile to produce a statistically derived decision classifying the sample as an IBS sample or non-IBS sample based upon the diagnostic marker profile, wherein the diagnostic marker profile indicates the presence or level of at least one diagnostic marker in the sample.

In a related aspect, the present invention provides a computer-readable medium including code for controlling one or more processors to classify whether a sample from an individual is associated with IBS, the code comprising: (a) instructions to apply a first statistical process to a data set comprising a diagnostic marker profile to produce a statistically derived decision classifying the sample as an IBD sample or non-IBD sample based upon the diagnostic marker profile, wherein the diagnostic marker profile indicates the presence or level of at least one diagnostic marker in the sample; and if the sample is classified as a non-IBD sample, (b) instructions to apply a second statistical process to the same or different data set to produce a second statistically derived decision classifying the non-IBD sample as an IBS sample or non-IBS sample.

In one embodiment, the computer-readable medium for ruling in IBS comprises instructions to apply a statistical process to a data set comprising a diagnostic marker profile optionally in combination with a symptom profile which indicates the presence or severity of at least one symptom in the individual to produce a statistically derived decision classifying the sample as an IBS sample or non-IBS sample based upon the diagnostic marker profile and the symptom profile.

In other embodiments, the computer-readable medium for first ruling out IBD and then ruling in IBS comprises instructions to apply a first statistical process to a data set comprising a diagnostic marker profile optionally in combination with a symptom profile which indicates the presence or severity of at least one symptom in the individual to produce a statistically derived decision classifying the sample as an IBD sample or non-IBD sample based upon the diagnostic marker profile and the symptom profile; and if the sample is classified as a non-IBD sample, instructions to apply a second statistical process to the same or different data set to produce a second statistically derived decision classifying the non-IBD sample as an IBS sample or non-IBS sample. One skilled in the art will appreciate that the first and/or second statistical process can be applied to the diagnostic marker profile and the symptom profile simultaneously or sequentially in any order.

In one embodiment, the first and second statistical processes are implemented in different processors. Alternatively, the first and second statistical processes are implemented in a single processor. In another embodiment, the first statistical process is a learning statistical classifier system. Examples of learning statistical classifier systems suitable for use in the present invention are described above. In certain instances, the first and/or second statistical process is a single learning statistical classifier system such as, for example, a RF or C&RT. In certain other instances, the first and/or second statistical process is a combination of at least two learning statistical classifier systems. As a non-limiting example, the combination of learning statistical classifier systems comprises a RF and a NN or SVM, e.g., used in tandem. In some instances, the data obtained from using the learning statistical classifier system or systems can be processed using a processing algorithm.

In another aspect, the present invention provides a system for classifying whether a serum or blood sample from a subject is associated with irritable bowel syndrome (IBS), the system comprising: (a) a data acquisition module configured to produce a data set comprising a diagnostic marker profile, wherein the diagnostic marker profile indicates the presence or level of at least one diagnostic marker selected from the group consisting of β-tryptase, histamine, prostaglandin $E_2$ ($PGE_2$), and a combination thereof; (b) a data processing module configured to process the data set by applying a statistical process to the data set to produce a statistically derived decision classifying the sample as an IBS sample or non-IBS sample based upon the diagnostic marker profile; and (c) a display module configured to display the statistically derived decision.

In certain embodiments, the system for classifying whether a serum or blood sample is associated with IBS, aiding in the diagnosis of IBS, or ruling in IBS comprises a data acquisition module configured to produce a data set comprising a diagnostic marker profile optionally in combination with a symptom profile which indicates the presence or severity of at least one symptom in the individual; a data processing module configured to process the data set by applying a statistical process to the data set to produce a statistically derived decision classifying the sample as an IBS sample or non-IBS sample based upon the diagnostic marker profile and the symptom profile; and a display module configured to display the statistically derived decision.

In a related aspect, the present invention provides a system for classifying whether a sample from an individual is associated with IBS, the system comprising: (a) a data acquisition module configured to produce a data set comprising a diagnostic marker profile, wherein the diagnostic marker profile indicates the presence or level of at least one diagnostic marker in the sample; (b) a data processing module configured to process the data set by applying a first statistical process to the data set to produce a first statistically derived decision classifying the sample as an IBD sample or non-IBD sample based upon the diagnostic marker profile; if the sample is classified as a non-IBD sample, a data processing module configured to apply a second statistical process to the same or different data set to produce a second statistically derived decision classifying the non-IBD sample as an IBS sample or non-IBS sample; and (c) a display module configured to display the first and/or the second statistically derived decision.

In one embodiment, the system for first ruling out IBD and then ruling in IBS comprises a data acquisition module configured to produce a data set comprising a diagnostic marker profile optionally in combination with a symptom profile which indicates the presence or severity of at least one symptom in the individual; a data processing module configured to process the data set by applying a first statistical process to the data set to produce a first statistically derived decision classifying the sample as an IBD sample or non-IBD sample based upon the diagnostic marker profile and the symptom profile; if the sample is classified as a non-IBD sample, a data processing module configured to apply a second statistical process to the same or different data set to produce a second statistically derived decision classifying the non-IBD sample as an IBS sample or non-IBS sample; and a display module configured to display the first and/or the second statistically derived decision.

In certain embodiments the diagnostic marker profile indicates the level of at least one additional diagnostic marker selected from the group consisting of Brain-Derived Neurotropic Factor (BDNF), Neutrophil Gelatinase-Associated Lipocalin (NGAL), TNF-related Weak Inducer of Apoptosis (TWEAK), Growth-Related Oncogene Alpha (GRO-α), Interleukin-1 Beta (IL-1β), Tissue Inhibitor of Metalloproteinase-1 (TIMP-1), Anti-*Saccharomyces cerevisiae* Antibody (ASCA-IgA), Anti-CBir-1 Antibody (CBir1), Anti-Human Neutrophil Cytoplasmic Antibody (ANCA), Anti-Human Tissue Transglutaminase IgA (tTG), and a combination thereof. In certain embodiments, the method comprises detecting the presence or level of at least two, three, four, five, six, seven, eight, nine, or all ten of the additional biomarkers provided above.

In yet other embodiments, the diagnostic marker profile indicates the level of at least one additional diagnostic marker selected from the group consisting of a cytokine (e.g., IL-8, IL-1β, TWEAK, leptin, OPG, MIP-3β, GROα, CXCL4/PF-4, and/or CXCL7/NAP-2), growth factor (e.g., EGF, VEGF, PEDF, BDNF, and/or SDGF), anti-neutrophil antibody (e.g., ANCA, pANCA, cANCA, NSNA, and/or SAPPA), ASCA (e.g., ASCA-IgA, ASCA-IgG, and/or ASCA-IgM), antimicrobial antibody (e.g., anti-OmpC antibody, anti-flagellin antibody, and/or anti-I2 antibody), lactoferrin, anti-tTG antibody, lipocalin (e.g., NGAL, NGAL/MMP-9 complex), MMP (e.g., MMP-9), TIMP (e.g., TIMP-1), alpha-globulin (e.g., alpha-2-macroglobulin, haptoglobin, and/or orosomucoid), actin-severing protein (e.g., gelsolin), S100 protein (e.g., calgranulin), fibrinopeptide (e.g., FIBA), CGRP, tachykinin (e.g., Substance P), ghrelin, neurotensin, corticotropin-releasing hormone, and combinations thereof. In yet other embodiments, the presence or level of other diagnostic markers such as, for example, anti-lactoferrin antibody, L-selectin/CD62L, elastase, C-reactive protein (CRP), calprotectin, anti-U1-70 kDa autoantibody, zona occludens 1 (ZO-1), vasoactive intestinal peptide (VIP), serum amyloid A, gastrin, and a combination thereof may also be detected.

IV. Diseases and Disorders with IBS-Like Symptoms

A variety of structural or metabolic diseases and disorders can cause signs or symptoms that are similar to IBS. As non-limiting examples, patients with diseases and disorders such as inflammatory bowel disease (IBD), Celiac disease (CD), acute inflammation, diverticulitis, ileal pouch-anal anastomosis, microscopic colitis, chronic infectious diarrhea, lactase deficiency, cancer (e.g., colorectal cancer), a mechanical obstruction of the small intestine or colon, an enteric infection, ischemia, maldigestion, malabsorption, endometriosis, and unidentified inflammatory disorders of the intestinal tract can present with abdominal discomfort associated with mild to moderate pain and a change in the consistency and/or frequency of stools that are similar to IBS. Additional IBS-like symptoms can include chronic diarrhea or constipation or an alternating form of each, weight loss, abdominal distention or bloating, and mucus in the stool.

Most IBD patients can be classified into one of two distinct clinical subtypes, Crohn's disease and ulcerative colitis. Crohn's disease is an inflammatory disease affecting the lower part of the ileum and often involving the colon and other regions of the intestinal tract. Ulcerative colitis is characterized by an inflammation localized mostly in the mucosa and submucosa of the large intestine. Patients suffering from these clinical subtypes of IBD typically have IBS-like symptoms such as, for example, abdominal pain, chronic diarrhea, weight loss, and cramping.

The clinical presentation of Celiac disease is also characterized by IBS-like symptoms such as abdominal discomfort associated with chronic diarrhea, weight loss, and abdominal distension. Celiac disease is an immune-mediated disorder of the intestinal mucosa that is typically associated with villous atrophy, crypt hyperplasia, and/or inflammation of the mucosal lining of the small intestine. In addition to the malabsorption of nutrients, individuals with Celiac disease are at risk for mineral deficiency, vitamin deficiency, osteoporosis, autoimmune diseases, and intestinal malignancies (e.g., lymphoma and carcinoma). It is thought that exposure to proteins such as gluten (e.g., glutenin and prolamine proteins which are present in wheat, rye, barley, oats, millet, triticale, spelt, and kamut), in the appropriate genetic and environmental context, is responsible for causing Celiac disease.

Other diseases and disorders characterized by intestinal inflammation that present with IBS-like symptoms include, for example, acute inflammation, diverticulitis, ileal pouch-anal anastomosis, microscopic colitis, and chronic infectious diarrhea, as well as unidentified inflammatory disorders of the intestinal tract. Patients experiencing episodes of acute inflammation typically have elevated C-reactive protein (CRP) levels in addition to IBS-like symptoms. CRP is produced by the liver during the acute phase of the inflammatory process and is usually released about 24 hours post-commencement of the inflammatory process. Patients suffering from diverticulitis, ileal pouch-anal anastomosis, microscopic colitis, and chronic infectious diarrhea typically have elevated fecal lactoferrin and/or calprotectin levels in addition to IBS-like symptoms. Lactoferrin is a glycoprotein secreted by mucosal membranes and is the major protein in the secondary granules of leukocytes. Leukocytes are commonly recruited to inflammatory sites where they are activated, releasing granule content to the surrounding area. This process increases the concentration of lactoferrin in the stool.

Increased lactoferrin levels are observed in patients with ileal pouch-anal anastomosis (i.e., a pouch is created following complete resection of colon in severe cases of Crohn's disease) when compared to other non-inflammatory conditions of the pouch, like irritable pouch syndrome. Elevated levels of lactoferrin are also observed in patients with diverticulitis, a condition in which bulging pouches (i.e., diverticula) in the digestive tract become inflamed and/or infected, causing severe abdominal pain, fever, nausea, and a marked change in bowel habits. Microscopic colitis is a chronic inflammatory disorder that is also associated with increased fecal lactoferrin levels. Microscopic colitis is characterized by persistent watery diarrhea (non-bloody), abdominal pain usually associated with weight loss, a normal mucosa during colonoscopy and radiological examination, and very specific histopathological changes. Microscopic colitis consists of two diseases, collagenous colitis and lymphocytic colitis. Collagenous colitis is of unknown etiology and is found in patients with long-term watery diarrhea and a normal colonoscopy examination. Both collagenous colitis and lymphocytic colitis are characterized by increased lymphocytes in the lining of the colon. Collagenous colitis is further characterized by a thickening of the sub-epithelial collagen layer of the colon. Chronic infectious diarrhea is an illness that is also associated with increased fecal lactoferrin levels. Chronic infectious diarrhea is usually caused by a bacterial, viral, or protozoan infection, with patients presenting with IBS-like symptoms such as diarrhea and abdominal pain. Increased lactoferrin levels are also observed in patients with IBD.

In addition to determining CRP and/or lactoferrin and/or calprotectin levels, diseases and disorders associated with intestinal inflammation can also be ruled out by detecting the presence of blood in the stool, such as fecal hemoglobin. Intestinal bleeding that occurs without the patient's knowledge is called occult or hidden bleeding. The presence of occult bleeding (e.g., fecal hemoglobin) is typically observed in a stool sample from the patient. Other conditions such as ulcers (e.g., gastric, duodenal), cancer (e.g., stomach cancer, colorectal cancer), and hemorrhoids can also present with IBS-like symptoms including abdominal pain and a change in the consistency and/or frequency of stools.

In addition, fecal calprotectin levels can also be assessed. Calprotectin is a calcium binding protein with antimicrobial activity derived predominantly from neutrophils and monocytes. Calprotectin has been found to have clinical relevance in cystic fibrosis, rheumatoid arthritis, IBD, colorectal cancer, HIV, and other inflammatory diseases. Its level has been measured in serum, plasma, oral, cerebrospinal and synovial fluids, urine, and feces. Advantages of fecal calprotectin in GI disorders have been recognized: stable for 3-7 days at room temperature enabling sample shipping through regular mail; correlated to fecal alpha 1-antitrypsin in patients with Crohn's disease; and elevated in a great majority of patients with gastrointestinal carcinomas and IBD. It was found that fecal calprotectin correlates well with endoscopic and histological gradings of disease activity in ulcerative colitis, and with fecal excretion of indium-111-labelled neutrophilic granulocytes, which is a standard of disease activity in IBD.

In view of the foregoing, it is clear that a wide array of diseases and disorders can cause IBS-like symptoms, thereby creating a substantial obstacle for definitively classifying a sample as an IBS sample. However, the present invention overcomes this limitation by classifying a sample from an individual as an IBS sample using, for example, a statistical algorithm, or by excluding (i.e., ruling out) those diseases and disorders that share a similar clinical presentation as IBS and identifying (i.e., ruling in) IBS in a sample using, for example, a combination of statistical algorithms.

V. Diagnostic Markers

A variety of diagnostic markers are suitable for use in the methods, systems, and code of the present invention for classifying a sample from an individual as an IBS sample or for ruling out one or more diseases or disorders associated with IBS-like symptoms in a sample from an individual. Examples of diagnostic markers include, without limitation, cytokines, growth factors, anti-neutrophil antibodies, anti-*Saccharomyces cerevisiae* antibodies, antimicrobial antibodies, anti-tissue transglutaminase (tTG) antibodies, lipocalins, matrix metalloproteinases (MMPs), complexes of lipocalin and MMP, tissue inhibitor of metalloproteinases (TIMPs), globulins (e.g., alpha-globulins), actin-severing proteins, S100 proteins, fibrinopeptides, calcitonin gene-related peptide (CGRP), tachykinins, ghrelin, neurotensin, corticotropin-releasing hormone (CRH), serine proteases (e.g., tryptases such as β-tryptase, elastase, etc.), prostaglandin (e.g., $PGE_2$), histamine, C-reactive protein (CRP), lactoferrin, anti-lactoferrin antibodies, calprotectin, hemoglobin, NOD2/CARD15, serotonin reuptake transporter (SERT), tryptophan hydroxylase-1,5-hydroxytryptamine (5-HT), lactulose, and combinations thereof. Additional diagnostic markers for predicting IBS in accordance with the present invention can be selected using the techniques described in Example 14 from US Patent Publication No. 2008/0085524, filed Aug. 14, 2007, which is herein incorporated by reference in its entirety for all purposes. One skilled in the art will also know of other diagnostic markers suitable for use in the present invention.

In particular embodiments, a diagnostic marker profile is determined by detecting the presence or level of at least one, two, or all three of the following biomarkers: a serine protease (e.g., a tryptase such as β-tryptase); a prostaglandin (e.g., $PGE_2$); and/or histamine.

In other embodiments, the presence or level of at least two, three, four, five, six, seven, eight, nine, ten, or more diagnostic markers are determined in the individual's sample. In certain instances, the cytokine comprises one or more of the cytokines described below. Preferably, the presence or level of IL-8, IL-1β, TNF-related weak inducer of apoptosis (TWEAK), leptin, osteoprotegerin (OPG), MIP-3β, GROα, CXCL4/PF-4, and/or CXCL7/NAP-2 is determined in the individual's sample. In certain other instances, the growth factor comprises one or more of the growth factors described below. Preferably, the presence or level of epidermal growth factor (EGF), vascular endothelial growth factor (VEGF), pigment epithelium-derived factor (PEDF), brain-derived neurotrophic factor (BDNF), and/or amphiregulin (SDGF) is determined in the individual's sample.

In some instances, the anti-neutrophil antibody comprises ANCA, pANCA, cANCA, NSNA, SAPPA, and combinations thereof. In other instances, the ASCA comprises ASCA-IgA, ASCA-IgG, ASCA-IgM, and combinations thereof. In further instances, the antimicrobial antibody comprises an anti-OmpC antibody, anti-flagellin antibody, anti-I2 antibody, and combinations thereof.

In certain instances, the lipocalin comprises one or more of the lipocalins described below. Preferably, the presence or level of neutrophil gelatinase-associated lipocalin (NGAL) and/or a complex of NGAL and a matrix metalloproteinase (e.g., NGAL/MMP-9 complex) is determined in the individual's sample. In other instances, the matrix metalloproteinase (MMP) comprises one or more of the MMPs described below. Preferably, the presence or level of MMP-9 is determined in the individual's sample. In further instances, the tissue inhibitor of metalloproteinase (TIMP) comprises one or more of the TIMPs described below. Preferably, the presence or level of TIMP-1 is determined in the individual's sample. In yet further instances, the alpha-globulin comprises one or more of the alpha-globulins described below. Preferably, the presence or level of alpha-2-macroglobulin, haptoglobin, and/or orosomucoid is determined in the individual's sample.

In certain other instances, the actin-severing protein comprises one or more of the actin-severing proteins described below. Preferably, the presence or level of gelsolin is determined in the individual's sample. In additional instances, the S100 protein comprises one or more of the S100 proteins described below including, for example, calgranulin. In yet other instances, the fibrinopeptide comprises one or more of the fibrinopeptides described below. Preferably, the presence or level of fibrinopeptide A (FIBA) is determined in the individual's sample. In further instances, the presence or level of a tachykinin such as Substance P, neurokinin A, and/or neurokinin B is determined in the individual's sample.

In some instances, the serine protease comprises one or more of the serine proteases described below. Preferably, the presence or level of a serine protease such as tryptase (e.g., β-tryptase) is determined in the individual's sample. In other instances, the prostaglandin comprises one or more of the prostaglandins described below. Preferably, the presence or level of a prostaglandin such as $PGE_2$ is determined in the individual's sample.

The presence or level of other diagnostic markers such as, for example, anti-lactoferrin antibody, L-selectin/CD62L, elastase, C-reactive protein (CRP), calprotectin, anti-U1-70 kDa autoantibody, zona occludens 1 (ZO-1), vasoactive intestinal peptide (VIP), serum amyloid A, and/or gastrin can also be determined.

A. Serine Proteases

The determination of the presence or level of at least one serine protease in a sample is useful in the present invention. As used herein, the term "serine protease" includes any member of a family of proteases in which one of the amino acids at the active site is serine. Non-limiting examples of serine proteases include tryptase (e.g., α-tryptase, β-tryptase, γ-tryptase, and/or Δ-tryptase), elastase, chymotrypsin, trypsin, subtilisin, and combinations thereof. Tryptase is an abundant specific neutral protease of human mast cells that can be measured in various biological fluids and can serve as a useful marker for mast cell activation. In fact, tryptase can be used as a marker for mast cell activation in IBS. It is believed that tryptase, possibly by activation of protease-activated receptor-2, is a good candidate to explain the pro-secretory and pro-inflammatory effects of mast cells, however other mast cell mediators could also involved. In a preferred embodiment, β-tryptase (TPBAB1) is detected in a blood or serum sample from a subject. β-tryptase, also commonly referred to as Tryptase beta-1 or Tryptase I, is encoded by the tryptase alpha/beta 1 gene (TPSAB1; NM_003294) which is translated to form a 275 amino acid tryptase beta-1 precursor protein (NP_003285). The precursor protein is then processed by the removal of a signal peptide (amino acids 1-18) and activation peptide propeptide (amino acids 19-30) resulting in the mature Tryptase beta-1 polypeptide (amino acids 31-275; UniProt: Q15661).

In certain instances, the presence or level of a particular serine protease such as tryptase is detected at the level of mRNA expression with an assay such as, for example, a hybridization assay or an amplification-based assay. In certain other instances, the presence or level of a particular serine protease such as tryptase is detected at the level of protein expression using, for example, an immunoassay (e.g., ELISA) or an immunohistochemical assay. Suitable ELISA techniques for determining the presence or level of tryptase in a serum sample are described herein. In a particularly preferred embodiment, the level of β-tryptase is detected in a blood or serum sample using a sandwich ELISA assay in which the detecting antibody is an alkaline phosphatase conjugated anti-β-tryptase antibody, for example, commercial antibody G3. A luminescent substrate, for example, CPSD (disodium 3-(4-methoxyspiro{1,2-dioxetane-3,2'-(5'-chloro)tricyclo[3.3.1.13,7]decan}-4-yl)phenyl phosphate), can then be used to enhance the sensitivity of the assay.

B. Prostaglandins

The determination of the presence or level of at least one prostaglandin in a sample is also useful in the present invention. As used herein, the term "prostaglandin" includes any member of a group of lipid compounds that are derived enzymatically from fatty acids and have important functions in the animal body. Every prostaglandin contains 20 carbon atoms, including a 5-carbon ring. Prostaglandins, together with the thromboxanes and prostacyclins, form the prostanoid class of fatty acid derivatives. The prostanoid class is a subclass of the eicosanoids. Non-limiting examples of prostaglandins include prostaglandin $I_2$ ($PGI_2$), prostaglandin $E_2$ ($PGE_2$), prostaglandin $F_{2\alpha}$ ($PGF_{2\alpha}$), and combinations thereof. In a preferred embodiment, prostaglandin $E_2$ ($PGE_2$) is detected in a blood or serum sample from a subject, for example, a subject suspected of having IBS. In certain embodiments, $PGE_2$ may be detected by an ELISA or chemiluminescent assay. Suitable ELISA kits for determining the presence or level of $PGE_2$ in a serum sample are available from, e.g., Cayman Chemical Co. (Ann Arbor, Mich.).

C. Histamine

The determination of the presence or level of histamine in a sample is also useful in the present invention. As used herein, the term "histamine" includes a biogenic amine involved in local immune responses as well as regulating physiological function in the gut and acting as a neurotransmitter. Histamine triggers the inflammatory response. As part of an immune response to foreign pathogens, histamine is produced by basophils and by mast cells found in nearby connective tissues. Histamine increases the permeability of the capillaries to white blood cells and other proteins, in order to allow them to engage foreign invaders in the affected tissues. It is found in virtually all animal body cells. In a preferred embodiment, histamine is detected in a blood or serum sample from a subject, for example, a subject suspected of having IBS. In certain embodiments, histamine may be detected by an ELISA or chemiluminescent assay. Suitable ELISA kits for determining the presence or level of histamine in a serum sample are available from, e.g., Immunotech (Czech Republic) and Cayman Chemical Co. (Ann Arbor, Mich.).

D. Cytokines

The determination of the presence or level of at least one cytokine in a sample is particularly useful in the present invention. As used herein, the term "cytokine" includes any of a variety of polypeptides or proteins secreted by immune cells that regulate a range of immune system functions and encompasses small cytokines such as chemokines. The term "cytokine" also includes adipocytokines, which comprise a group of cytokines secreted by adipocytes that function, for example, in the regulation of body weight, hematopoiesis, angiogenesis, wound healing, insulin resistance, the immune response, and the inflammatory response.

In certain aspects, the presence or level of at least one cytokine including, but not limited to, TNF-α, TNF-related weak inducer of apoptosis (TWEAK), osteoprotegerin (OPG), IFN-α, IFN-β, IFN-γ, IL-1α, IL-1β, IL-1 receptor antagonist (IL-1ra), IL-2, IL-4, IL-5, IL-6, soluble IL-6 receptor (sIL-6R), IL-7, IL-8, IL-9, IL-10, IL-12, IL-13, IL-15, IL-17, IL-23, and IL-27 is determined in a sample. In certain other aspects, the presence or level of at least one chemokine such as, for example, CXCL1/GRO1/GROα, CXCL2/GRO2, CXCL3/GRO3, CXCL4/PF-4, CXCL5/ENA-78, CXCL6/GCP-2, CXCL7/NAP-2, CXCL9/MIG, CXCL10/IP-10, CXCL11/1-TAC, CXCL12/SDF-1, CXCL13/BCA-1, CXCL14/BRAK, CXCL15, CXCL16, CXCL17/DMC, CCL1, CCL2/MCP-1, CCL3/MIP-1α, CCL4/MIP-1β, CCL5/RANTES, CCL6/C10, CCL7/MCP-3, CCL8/MCP-2, CCL9/CCL10, CCL11/Eotaxin, CCL12/MCP-5, CCL13/MCP-4, CCL14/HCC-1, CCL15/MIP-5, CCL16/LEC, CCL17/TARC, CCL18/MIP-4, CCL19/MIP-3β, CCL20/MIP-3α, CCL21/SLC, CCL22/MDC, CCL23/MPIF1, CCL24/Eotaxin-2, CCL25/TECK, CCL26/Eotaxin-3, CCL27/CTACK, CCL28/MEC, CL1, CL2, and $CX_3CL1$ is determined in a sample. In certain further aspects, the presence or level of at least one adipocytokine including, but not limited to, leptin, adiponectin, resistin, active or total plasminogen activator inhibitor-1 (PAI-1), visfatin, and retinol binding protein 4 (RBP4) is determined in a sample. Preferably, the presence or level of IL-8, IL-1β, TWEAK, leptin, OPG, MIP-3β, GROα, CXCL4/PF-4, and/or CXCL7/NAP-2 is determined.

In certain instances, the presence or level of a particular cytokine is detected at the level of mRNA expression with an assay such as, for example, a hybridization assay or an amplification-based assay. In certain other instances, the presence or level of a particular cytokine is detected at the level of protein expression using, for example, an immunoassay (e.g., ELISA) or an immunohistochemical assay. Suitable ELISA kits for determining the presence or level of a cytokine such as IL-8, IL-1β, MIP-3β, GROα, CXCL4/PF-4, or CXCL7/NAP-2 in a serum, plasma, saliva, or urine sample are available from, e.g., R&D Systems, Inc. (Minneapolis, Minn.), Neogen Corp. (Lexington, Ky.), Alpco Diagnostics (Salem, N.H.), Assay Designs, Inc. (Ann Arbor, Mich.), BD Biosciences Pharmingen (San Diego, Calif.), Invitrogen (Camarillo, Calif.), Calbiochem (San Diego, Calif.), CHEMICON International, Inc. (Temecula, Calif.), Antigenix America Inc. (Huntington Station, N.Y.), QIAGEN Inc. (Valencia, Calif.), Bio-Rad Laboratories, Inc. (Hercules, Calif.), and/or Bender MedSystems Inc. (Burlingame, Calif.).

1. TWEAK

TWEAK is a member of the TNF superfamily of structurally related cytokines. Full-length, membrane-anchored TWEAK can be found on the surface of many cell types and a smaller, biologically active form, generated via proteolytic processing, has also been detected in the extracellular milieu (see, e.g., Chicheportiche et al., J. Biol. Chem., 272:32401-32410 (1997)). TWEAK acts via binding to a TNF receptor superfamily member named fibroblast growth factor-inducible 14 (Fn14; also known as tumor necrosis factor receptor superfamily member 12A or TNFRSF12A). TWEAK has multiple biological activities, including stimulation of cell growth and angiogenesis, induction of inflammatory cytokines, and stimulation of apoptosis (see, e.g., Wiley et al., Cytokine Growth Factor Rev., 14:241-249 (2003)). In particular, TWEAK has been shown to induce the expression of PGE2, MMP-1, IL-6, IL-8, RANTES, and IP-10 in fibroblasts and synoviocytes, and to upregulate ICAM-1, E-selectin, IL-8, and MCP-1 expression in endothelial cells (see, e.g., Campbell et al., Front. Biosci., 9:2273-2284 (2004)). It has also been demonstrated that TWEAK binding to the Fn14 receptor, or constitutive Fn14 overexpression, activates the NF-κB signaling pathway, which plays an important role in immune and inflammatory processes, oncogenesis, cancer therapy resistance, and tumorigenesis (see, e.g., Winkles et al., Cancer Lett., 235:11-17 (2006); and Winkles et al., Front. Biosci., 12:2761-2771 (2007)). One skilled in the art will appreciate that TWEAK is also known as tumor necrosis factor ligand superfamily member 12 (TNFSF12), APO3 ligand (APO3L), CD255, DR3 ligand, FN14, and UNQ181/PRO207.

Suitable ELISA kits for determining the presence or level of TWEAK in a biological sample such as a serum, plasma, saliva, or urine sample are available from, e.g., Antigenix America Inc. (Huntington Station, N.Y.), Bender MedSystems Inc. (Burlingame, Calif.), Agdia Inc. (Elkhart, Ind.), American Research Products Inc. (Belmont, Mass.), Biomeda Corp. (Foster City, Calif.), BioVision, Inc. (Mountain View, Calif.), and Kamiya Biomedical Co. (Seattle, Wash.).

2. Osteoprotegerin (OPG)

OPG is a 401-amino acid member of the TNF superfamily of structurally related cytokines OPG, which is homologous to the receptor activator of NFκB (RANK), inhibits the differentiation of macrophages into osteoclasts and regulates the resorption of osteoclasts by acting as a soluble decoy receptor for RANK ligand (RANKL; also known as OPG ligand (OPGL)). As a result, the OPG-RANK-RANKL system plays a direct and essential role in the formation, function, and survival of osteoclasts. The OPG-RANK-RANKL system has also been shown to modulate cancer cell migration, thus controlling the development of bone metastases. One skilled in the art will appreciate that OPG is also known as osteoprotegrin and osteoclastogenesis inhibitory factor (OCIF).

Suitable ELISA kits for determining the presence or level of OPG in a serum, plasma, saliva, or urine sample are available from, e.g., Antigenix America Inc. (Huntington Station, N.Y.), Immunodiagnostic Systems Ltd. (Boldon, United Kingdom), and BioVendor, LLC (Candler, N.C.).

3. Leptin

Leptin, a member of the adipocytokine family of cytokines, is a 16-kD peptide hormone that plays a critical role in the regulation of body weight by inhibiting food intake and stimulating energy expenditure. It is predominantly synthesized by adipocytes and circulates in the plasma in amounts proportional to body fat content (see, e.g., Maffei et al., Nat. Med., 1:1155-1161 (1995); Considine et al., Diabetes, 45:992-994 (1996)). Leptin displays a high degree of homology among different species and it is also analogous in structure to other cytokines (see, e.g., Madej et al., FEBS Lett., 373:13-18 (1995)). Leptin acts through the leptin receptor, a single-transmembrane-domain receptor of the class I cytokine superfamily of receptors, which are characterized by extracellular motifs of four cysteine residues and a number of fibronectin type III domains (see, e.g., Heim, Eur. J. Clin. Invest., 26:1-12 (1996)). The leptin receptor is known to exist as a homodimer and is activated by conformational changes that occur following ligand binding to the receptor (see, e.g., Devos et al., *J. Biol. Chem.*, 272:18304-18310 (1997)). Six leptin receptor isoforms, generated by alternate splicing, have been identified to date (see, e.g., Wang et al., *Nature*, 393: 684-688 (1998); Lee et al., *Nature*, 379:632-635 (1996)).

Suitable ELISA kits for determining the presence or level of leptin in a biological sample such as a serum, plasma, saliva, or urine sample are available from, e.g., R&D Systems, Inc. (Minneapolis, Minn.), B-Bridge International (Mountain View, Calif.), Neogen Corp. (Lexington, Ky.), Assay Designs, Inc. (Ann Arbor, Mich.), Invitrogen (Camarillo, Calif.), CHEMICON International, Inc. (Temecula, Calif.), Antigenix America Inc. (Huntington Station, N.Y.), LINCO Research, Inc. (St. Charles, Mo.), Diagnostic Systems Laboratories, Inc. (Webster, Tex.), Immuno-Biological Laboratories, Inc. (Minneapolis, Minn.), and Cayman Chemical Co. (Ann Arbor, Mich.).

E. Growth Factors

The determination of the presence or level of one or more growth factors in a sample is also useful in the present invention. As used herein, the term "growth factor" includes any of a variety of peptides, polypeptides, or proteins that are capable of stimulating cellular proliferation and/or cellular differentiation.

In certain aspects, the presence or level of at least one growth factor including, but not limited to, epidermal growth factor (EGF), heparin-binding epidermal growth factor (HB-EGF), vascular endothelial growth factor (VEGF), pigment epithelium-derived factor (PEDF; also known as SERPINF1), amphiregulin (AREG; also known as schwannoma-derived growth factor (SDGF)), basic fibroblast growth factor (bFGF), hepatocyte growth factor (HGF), transforming growth factor-α (TGF-α), transforming growth factor-β (TGF-β), bone morphogenetic proteins (e.g., BMP1-BMP15), platelet-derived growth factor (PDGF), nerve growth factor (NGF), β-nerve growth factor (β-NGF), neurotrophic factors (e.g., brain-derived neurotrophic factor (BDNF), neurotrophin 3 (NT3), neurotrophin 4 (NT4), etc.), growth differentiation factor-9 (GDF-9), granulocyte-colony stimulating factor (G-CSF), granulocyte-macrophage colony stimulating factor (GM-CSF), myostatin (GDF-8), erythropoietin (EPO), and thrombopoietin (TPO) is determined in a sample. Preferably, the presence or level of EGF, VEGF, PEDF, amphiregulin (SDGF), and/or BDNF is determined.

In certain instances, the presence or level of a particular growth factor is detected at the level of mRNA expression with an assay such as, for example, a hybridization assay or an amplification-based assay. In certain other instances, the presence or level of a particular growth factor is detected at the level of protein expression using, for example, an immunoassay (e.g., ELISA) or an immunohistochemical assay. Suitable ELISA kits for determining the presence or level of a growth factor such as EGF, VEGF, PEDF, SDGF, or BDNF in a serum, plasma, saliva, or urine sample are available from, e.g., Antigenix America Inc. (Huntington Station, N.Y.), Promega (Madison, Wis.), R&D Systems, Inc. (Minneapolis, Minn.), Invitrogen (Camarillo, Calif.), CHEMICON International, Inc. (Temecula, Calif.), Neogen Corp. (Lexington, Ky.), PeproTech (Rocky Hill, N.J.), Alpco Diagnostics (Salem, N.H.), Pierce Biotechnology, Inc. (Rockford, Ill.), and/or Abazyme (Needham, Mass.).

F. Lipocalins

The determination of the presence or level of one or more lipocalins in a sample is also useful in the present invention. As used herein, the term "lipocalin" includes any of a variety of small extracellular proteins that are characterized by several common molecular recognition properties: the ability to bind a range of small hydrophobic molecules; binding to specific cell-surface receptors; and the formation of complexes with soluble macromolecules (see, e.g., Flowers, *Biochem. J.*, 318:1-14 (1996)). The varied biological functions of lipocalins are mediated by one or more of these properties. The lipocalin protein family exhibits great functional diversity, with roles in retinol transport, invertebrate cryptic coloration, olfaction and pheromone transport, and prostaglandin synthesis. Lipocalins have also been implicated in the regulation of cell homoeostasis and the modulation of the immune response, and, as carrier proteins, to act in the general clearance of endogenous and exogenous compounds. Although lipocalins have great diversity at the sequence level, their three-dimensional structure is a unifying characteristic. Lipocalin crystal structures are highly conserved and comprise a single eight-stranded continuously hydrogen-bonded antiparallel beta-barrel, which encloses an internal ligand-binding site.

In certain aspects, the presence or level of at least one lipocalin including, but not limited to, neutrophil gelatinase-associated lipocalin (NGAL; also known as human neutrophil lipocalin (HNL) or lipocalin-2), von Ebner's gland protein (VEGP; also known as lipocalin-1), retinol-binding protein (RBP), purpurin (PURP), retinoic acid-binding protein (RABP), $\alpha_{2u}$-globulin (A2U), major urinary protein (MUP), bilin-binding protein (BBP), α-crustacyanin, pregnancy protein 14 (PP14), β-lactoglobulin (B1g), $\alpha_1$-microglobulin (A1M), the gamma chain of C8 (C8γ), Apolipoprotein D (ApoD), lazarillo (LAZ), prostaglandin D2 synthase (PGDS), quiescence-specific protein (QSP), choroid plexus protein, odorant-binding protein (OBP), $\alpha_1$-acid glycoprotein (AGP), probasin (PBAS), aphrodisin, orosomucoid, and progestagen-associated endometrial protein (PAEP) is determined in a sample. In certain other aspects, the presence or level of at least one lipocalin complex including, for example, a complex of NGAL and a matrix metalloproteinase (e.g., NGAL/MMP-9 complex) is determined. Preferably, the presence or level of NGAL or a complex thereof with MMP-9 is determined.

In certain instances, the presence or level of a particular lipocalin is detected at the level of mRNA expression with an assay such as, for example, a hybridization assay or an amplification-based assay. In certain other instances, the presence or level of a particular lipocalin is detected at the level of protein expression using, for example, an immunoassay (e.g., ELISA) or an immunohistochemical assay. Suitable ELISA kits for determining the presence or level of a lipocalin such as NGAL in a serum, plasma, or urine sample are available from, e.g., AntibodyShop A/S (Gentofte, Denmark), Lab-Clinics SA (Barcelona, Spain), Lucerna-Chem AG (Luzern, Switzerland), R&D Systems, Inc. (Minneapolis, Minn.), and Assay Designs, Inc. (Ann Arbor, Mich.). Suitable ELISA kits for determining the presence or level of the NGAL/MMP-9 complex are available from, e.g., R&D Systems, Inc. (Minneapolis, Minn.). Additional NGAL and NGAL/MMP-9 complex ELISA techniques are described in, e.g., Kjeldsen et al., *Blood*, 83:799-807 (1994); and Kjeldsen et al., *J. Immunol. Methods*, 198:155-164 (1996).

G. Matrix Metalloproteinases

The determination of the presence or level of at least one matrix metalloproteinase (MMP) in a sample is also useful in the present invention. As used herein, the term "matrix metalloproteinase" or "MMP" includes zinc-dependent endopeptidases capable of degrading a variety of extracellular matrix proteins, cleaving cell surface receptors, releasing apoptotic ligands, and/or regulating chemokines MMPs are also thought to play a major role in cell behaviors such as cell proliferation, migration (adhesion/dispersion), differentiation, angiogenesis, and host defense.

In certain aspects, the presence or level of at least one at least one MMP including, but not limited to, MMP-1 (interstitial collagenase), MMP-2 (gelatinase-A), MMP-3 (stromelysin-1), MMP-7 (matrilysin), MMP-8 (neutrophil collagenase), MMP-9 (gelatinase-B), MMP-10 (stromelysin-2), MMP-11 (stromelysin-3), MMP-12 (macrophage metalloelastase), MMP-13 (collagenase-3), MMP-14, MMP-15, MMP-16, MMP-17, MMP-18 (collagenase-4), MMP-19, MMP-20 (enamelysin), MMP-21, MMP-23, MMP-24, MMP-25, MMP-26 (matrilysin-2), MMP-27, and MMP-28 (epilysin) is determined in a sample. Preferably, the presence or level of MMP-9 is determined.

In certain instances, the presence or level of a particular MMP is detected at the level of mRNA expression with an assay such as, for example, a hybridization assay or an amplification-based assay. In certain other instances, the presence or level of a particular MMP is detected at the level of protein expression using, for example, an immunoassay (e.g., ELISA) or an immunohistochemical assay. Suitable ELISA kits for determining the presence or level of an MMP such as MMP-9 in a serum or plasma sample are available from, e.g., Calbiochem (San Diego, Calif.), CHEMICON International, Inc. (Temecula, Calif.), and R&D Systems, Inc. (Minneapolis, Minn.).

H. Tissue Inhibitor of Metalloproteinases

The determination of the presence or level of at least one tissue inhibitor of metalloproteinase (TIMP) in a sample is also useful in the present invention. As used herein, the term "tissue inhibitor of metalloproteinase" or "TIMP" includes proteins capable of inhibiting MMPs.

In certain aspects, the presence or level of at least one at least one TIMP including, but not limited to, TIMP-1, TIMP-2, TIMP-3, and TIMP-4 is determined in a sample. Preferably, the presence or level of TIMP-1 is determined.

In certain instances, the presence or level of a particular TIMP is detected at the level of mRNA expression with an assay such as, for example, a hybridization assay or an amplification-based assay. In certain other instances, the presence or level of a particular TIMP is detected at the level of protein expression using, for example, an immunoassay (e.g., ELISA) or an immunohistochemical assay. Suitable ELISA kits for determining the presence or level of a TIMP such as TIMP-1 in a serum or plasma sample are available from, e.g., Alpco Diagnostics (Salem, N.H.), Calbiochem (San Diego, Calif.), Invitrogen (Camarillo, Calif.), CHEMICON International, Inc. (Temecula, Calif.), and R&D Systems, Inc. (Minneapolis, Minn.).

I. Globulins

The determination of the presence or level of at least one globulin in a sample is also useful in the present invention. As used herein, the term "globulin" includes any member of a heterogeneous series of families of serum proteins which migrate less than albumin during serum electrophoresis. Protein electrophoresis is typically used to categorize globulins into the following three categories: alpha-globulins (i.e., alpha-1-globulins or alpha-2-globulins); beta-globulins; and gamma-globulins.

Alpha-globulins comprise a group of globular proteins in plasma which are highly mobile in alkaline or electrically-charged solutions. They generally function to inhibit certain blood protease and inhibitor activity. Examples of alpha-globulins include, but are not limited to, alpha-2-macroglobulin (α2-MG), haptoglobin (Hp), orosomucoid, alpha-1-antitrypsin, alpha-1-antichymotrypsin, alpha-2-antiplasmin, antithrombin, ceruloplasmin, heparin cofactor II, retinol binding protein, and transcortin. Preferably, the presence or level of α2-MG, haptoglobin, and/or orosomucoid is determined. In certain instances, one or more haptoglobin allotypes such as, for example, Hp precursor, Hpβ, Hpα1, and Hpα2, are determined.

In certain instances, the presence or level of a particular globulin is detected at the level of mRNA expression with an assay such as, for example, a hybridization assay or an amplification-based assay. In certain other instances, the presence or level of a particular globulin is detected at the level of protein expression using, for example, an immunoassay (e.g., ELISA) or an immunohistochemical assay. Suitable ELISA kits for determining the presence or level of a globulin such as α2-MG, haptoglobin, or orosomucoid in a serum, plasma, or urine sample are available from, e.g., GenWay Biotech, Inc. (San Diego, Calif.) and/or Immundiagnostik AG (Bensheim, Germany)

J. Actin-Severing Proteins

The determination of the presence or level of at least one actin-severing protein in a sample is also useful in the present invention. As used herein, the term "actin-severing protein" includes any member of a family of proteins involved in actin remodeling and regulation of cell motility. Non-limiting examples of actin-severing proteins include gelsolin (also known as brevin or actin-depolymerizing factor), villin, fragmin, and adseverin. For example, gelsolin is a protein of leukocytes, platelets, and other cells which severs actin filaments in the presence of submicromolar calcium, thereby solating cytoplasmic actin gels.

In certain instances, the presence or level of a particular actin-severing protein is detected at the level of mRNA expression with an assay such as, for example, a hybridization assay or an amplification-based assay. In certain other instances, the presence or level of a particular actin-severing protein is detected at the level of protein expression using, for example, an immunoassay (e.g., ELISA) or an immunohistochemical assay. Suitable ELISA techniques for determining the presence or level of an actin-severing protein such as gelsolin in a plasma sample are described in, e.g., Smith et al., *J. Lab. Clin. Med.*, 110:189-195 (1987); and Hiyoshi et al., *Biochem. Mol. Biol. Int.*, 32:755-762 (1994).

K. S100 Proteins

The determination of the presence or level of at least one S100 protein in a sample is also useful in the present invention. As used herein, the term "S100 protein" includes any member of a family of low molecular mass acidic proteins characterized by cell-type-specific expression and the presence of 2 EF-hand calcium-binding domains. There are at least 21 different types of S100 proteins in humans. The name is derived from the fact that S100 proteins are 100% soluble in ammonium sulfate at neutral pH. Most S100 proteins are homodimeric, consisting of two identical polypeptides held together by non-covalent bonds. Although S100 proteins are structurally similar to calmodulin, they differ in that they are cell-specific, expressed in particular cells at different levels depending on environmental factors. S-100 proteins are normally present in cells derived from the neural crest (e.g., Schwann cells, melanocytes, glial cells), chondrocytes, adipocytes, myoepithelial cells, macrophages, Langerhans cells, dendritic cells, and keratinocytes. S100 proteins have been implicated in a variety of intracellular and extracellular functions such as the regulation of protein phosphorylation, transcription factors, $Ca^{2+}$ homeostasis, the dynamics of cytoskeleton constituents, enzyme activities, cell growth and differentiation, and the inflammatory response.

Calgranulin is an S100 protein that is expressed in multiple cell types, including renal epithelial cells and neutrophils, and are abundant in infiltrating monocytes and granulocytes under conditions of chronic inflammation. Examples of calgranulins include, without limitation, calgranulin A (also known as S100A8 or MRP-8), calgranulin B (also known as S100A9 or MRP-14), and calgranulin C (also known as S100A12).

In certain instances, the presence or level of a particular S100 protein is detected at the level of mRNA expression with an assay such as, for example, a hybridization assay or an amplification-based assay. In certain other instances, the presence or level of a particular S100 protein is detected at the level of protein expression using, for example, an immunoassay (e.g., ELISA) or an immunohistochemical assay. Suitable ELISA kits for determining the presence or level of an S100 protein such as calgranulin A (S100A8) or calgranulin B (S100A9) in a serum, plasma, or urine sample are available from, e.g., Peninsula Laboratories Inc. (San Carlos, Calif.) and Hycult biotechnology b.v. (Uden, The Netherlands).

Calprotectin, the complex of S100A8 and S100A9, is a calcium- and zinc-binding protein in the cytosol of neutrophils, monocytes, and keratinocytes. Calprotectin is a major protein in neutrophilic granulocytes and macrophages and accounts for as much as 60% of the total protein in the cytosol fraction in these cells. It is therefore a surrogate marker of neutrophil turnover. Its concentration in stool correlates with the intensity of neutrophil infiltration of the intestinal mucosa and with the severity of inflammation. In some instances, calprotectin can be measured with an ELISA using small (50-100 mg) fecal samples (see, e.g., Johne et al., *Scand J. Gastroenterol.*, 36:291-296 (2001)).

L. Tachykinins

The determination of the presence or level of at least one tachykinin in a sample is also useful in the present invention. As used herein, the term "tachykinin" includes amidated neuropeptides that share the carboxy-terminal sequence Phe-X-Gly-Leu-Met-$NH_2$. Tachykinins typically bind to one or more tachykinin receptors (e.g., TACR1, TACR2, and/or TACR3).

In certain aspects, the presence or level of at least one tachykinin including, but not limited to, substance P, neurokinin A, and neurokinin B is determined in a sample. Preferably, the presence or level of substance P is determined. Substance P is a peptide of 11 amino acids in length that is released by nerve endings in both the central and peripheral nervous systems. Among the numerous biological sites innervated by substance P-releasing neurons are the skin, intestines, stomach, bladder, and cardiovascular system.

In certain instances, the presence or level of a particular tachykinin is detected at the level of mRNA expression with an assay such as, for example, a hybridization assay or an amplification-based assay. In certain other instances, the presence or level of a particular tachykinin is detected at the level of protein expression using, for example, an immunoassay (e.g., ELISA) or an immunohistochemical assay. Suitable ELISA kits for determining the presence or level of a tachykinin such as substance P in a serum, plasma, saliva, or urine sample are available from, e.g., MD Biosciences Inc. (St. Paul, Minn.), Assay Designs, Inc. (Ann Arbor, Mich.), R&D Systems, Inc. (Minneapolis, Minn.), Sigma-Aldrich Corp. (St. Louis, Mo.), and Cayman Chemical Co. (Ann Arbor, Mich.).

M. Ghrelin

The determination of the presence or level of ghrelin in a sample is also useful in the present invention. As used herein, the term "ghrelin" includes a peptide of 28 amino acids that is an endogenous ligand for the growth hormone secretagogue receptor (GHSR) and is involved in regulating growth hormone release. Ghrelin can be acylated, typically with an n-octanoyl group at serine residue three, to form active ghrelin. Alternatively, ghrelin can exist as an unacylated form (i.e., desacyl-ghrelin). Ghrelin is primarily expressed in specialized enterochromaffin cells located mainly in the mucosa of the fundus of the stomach and has metabolic effects opposite to those of leptin. Ghrelin stimulates food intake, enhances the use of carbohydrates and reduces fat utilization, increases gastric motility and acid secretion, and reduces locomotor activity.

In certain instances, the presence or level of ghrelin is detected at the level of mRNA expression with an assay such as, for example, a hybridization assay or an amplification-based assay. In certain other instances, the presence or level of ghrelin is detected at the level of protein expression using, for example, an immunoassay (e.g., ELISA) or an immunohistochemical assay. Suitable ELISA kits for determining the presence or level of active ghrelin or desacyl-ghrelin in a serum, plasma, saliva, or urine sample are available from, e.g., Alpco Diagnostics (Salem, N.H.), Cayman Chemical Co. (Ann Arbor, Mich.), LINCO Research, Inc. (St. Charles, Mo.), and Diagnostic Systems Laboratories, Inc. (Webster, Tex.).

N. Neurotensin

The determination of the presence or level of neurotensin in a sample is also useful in the present invention. As used herein, the term "neurotensin" includes a tridecapeptide that is widely distributed throughout the central nervous system and the gastrointestinal tract. Neurotensin has been identified as an important mediator in the development and progression of several gastrointestinal functions and disease conditions, exerting its effects by interacting with specific receptors that act directly or indirectly on nerves, epithelial cells, and/or cells of the immune and inflammatory systems (see, e.g., Zhao et al., *Peptides*, 27:2434-2444 (2006)).

In certain instances, the presence or level of neurotensin is detected at the level of mRNA expression with an assay such as, for example, a hybridization assay or an amplification-based assay. In certain other instances, the presence or level of neurotensin is detected at the level of protein expression using, for example, an immunoassay (e.g., ELISA) or an immunohistochemical assay. Suitable ELISA techniques for determining the presence or level of neurotensin in a sample are described in, e.g., Davis et al., *J. Neurosci. Methods*, 14:15-23 (1985); and Williams et al., *J. Histochem. Cytochem.*, 37:831-841 (1989).

O. Corticotropin-Releasing Hormone

The determination of the presence or level of corticotropin-releasing hormone (CRH; also known as corticotropin-releasing factor or CRF) in a sample is also useful in the present invention. As used herein, the term "corticotropin-releasing hormone," "CRH," "corticotropin-releasing factor," or "CRF" includes a 41-amino acid peptide secreted by the paraventricular nucleus of the hypothalamus that mediates the proximal part of the response to stress in mammals such as humans. CRH typically binds to one or more corticotropin-releasing hormone receptors (e.g., CRHR1 and/or CRHR2). CRH is expressed by the hypothalamus, spinal cord, stomach, spleen, duodenum, adrenal gland, and placenta.

In certain instances, the presence or level of CRH is detected at the level of mRNA expression with an assay such as, for example, a hybridization assay or an amplification-based assay. In certain other instances, the presence or level of CRH is detected at the level of protein expression using, for example, an immunoassay (e.g., ELISA) or an immunohistochemical assay. Suitable ELISA kits for determining the presence or level of CRH in a serum, plasma, saliva, or urine sample are available from, e.g., Alpco Diagnostics (Salem, N.H.) and Cosmo Bio Co., Ltd. (Tokyo, Japan).

P. Anti-Neutrophil Antibodies

The determination of ANCA levels and/or the presence or absence of pANCA in a sample is also useful in the present invention. As used herein, the term "anti-neutrophil cytoplasmic antibody" or "ANCA" includes antibodies directed to cytoplasmic and/or nuclear components of neutrophils. ANCA activity can be divided into several broad categories based upon the ANCA staining pattern in neutrophils: (1) cytoplasmic neutrophil staining without perinuclear highlighting (cANCA); (2) perinuclear staining around the outside edge of the nucleus (pANCA); (3) perinuclear staining around the inside edge of the nucleus (NSNA); and (4) diffuse staining with speckling across the entire neutrophil (SAPPA). In certain instances, pANCA staining is sensitive to DNase treatment. The term ANCA encompasses all varieties of anti-neutrophil reactivity, including, but not limited to, cANCA, pANCA, NSNA, and SAPPA. Similarly, the term ANCA encompasses all immunoglobulin isotypes including, without limitation, immunoglobulin A and G.

ANCA levels in a sample from an individual can be determined, for example, using an immunoassay such as an enzyme-linked immunosorbent assay (ELISA) with alcohol-fixed neutrophils. The presence or absence of a particular category of ANCA such as pANCA can be determined, for example, using an immunohistochemical assay such as an indirect fluorescent antibody (IFA) assay. Preferably, the presence or absence of pANCA in a sample is determined using an immunofluorescence assay with DNase-treated, fixed neutrophils. In addition to fixed neutrophils, antigens specific for ANCA that are suitable for determining ANCA levels include, without limitation, unpurified or partially purified neutrophil extracts; purified proteins, protein fragments, or synthetic peptides such as histone H1 or ANCA-reactive fragments thereof (see, e.g., U.S. Pat. No. 6,074,835); histone H1-like antigens, porin antigens, *Bacteroides* antigens, or ANCA-reactive fragments thereof (see, e.g., U.S. Pat. No. 6,033,864); secretory vesicle antigens or ANCA-reactive fragments thereof (see, e.g., U.S. patent application Ser. No. 08/804,106); and anti-ANCA idiotypic antibodies. One skilled in the art will appreciate that the use of additional antigens specific for ANCA is within the scope of the present invention.

Q. Anti-*Saccharomyces cerevisiae* Antibodies

The determination of ASCA (e.g., ASCA-IgA and/or ASCA-IgG) levels in a sample is also useful in the present invention. As used herein, the term "anti-*Saccharomyces cerevisiae* immunoglobulin A" or "ASCA-IgA" includes antibodies of the immunoglobulin A isotype that react specifically with *S. cerevisiae*. Similarly, the term "anti-*Saccharomyces cerevisiae* immunoglobulin G" or "ASCA-IgG" includes antibodies of the immunoglobulin G isotype that react specifically with *S. cerevisiae*.

The determination of whether a sample is positive for ASCA-IgA or ASCA-IgG is made using an antigen specific for ASCA. Such an antigen can be any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from *S. cerevisiae* or from a variety of other sources so long as the antigen is capable of binding specifically to ASCA antibodies. Accordingly, exemplary sources of an antigen specific for ASCA, which can be used to determine the levels of ASCA-IgA and/or ASCA-IgG in a sample, include, without limitation, whole killed yeast cells such as *Saccharomyces* or *Candida* cells; yeast cell wall mannan such as phosphopeptidomannan (PPM); oligosaccharides such as oligomannosides; neoglycolipids; anti-ASCA idiotypic antibodies; and the like. Different species and strains of yeast, such as *S. cerevisiae* strain Su1, Su2, CBS 1315, or BM 156, or *Candida albicans* strain VW32, are suitable for use as an antigen specific for ASCA-IgA and/or ASCA-IgG. Purified and synthetic antigens specific for ASCA are also suitable for use in determining the levels of ASCA-IgA and/or ASCA-IgG in a sample. Examples of purified antigens include, without limitation, purified oligosaccharide antigens such as oligomannosides. Examples of synthetic antigens include, without limitation, synthetic oligomannosides such as those described in U.S. Patent Publication No. 20030105060, e.g., D-Man $\beta(1-2)$ D-Man $\beta(1-2)$ D-Man $\beta(1-2)$ D-Man-OR, D-Man $\alpha(1-2)$ D-Man $\alpha(1-2)$ D-Man $\alpha(1-2)$ D-Man-OR, and D-Man $\alpha(1-3)$ D-Man $\alpha(1-2)$ D-Man $\alpha(1-2)$ D-Man-OR, wherein R is a hydrogen atom, a $C_1$ to $C_{20}$ alkyl, or an optionally labeled connector group.

Preparations of yeast cell wall mannans, e.g., PPM, can be used in determining the levels of ASCA-IgA and/or ASCA-IgG in a sample. Such water-soluble surface antigens can be prepared by any appropriate extraction technique known in the art, including, for example, by autoclaving, or can be obtained commercially (see, e.g., Lindberg et al., *Gut*, 33:909-913 (1992)). The acid-stable fraction of PPM is also useful in the statistical algorithms of the present invention (Sendid et al., *Clin. Diag. Lab. Immunol.*, 3:219-226 (1996)). An exemplary PPM that is useful in determining ASCA levels in a sample is derived from *S. uvarum* strain ATCC #38926.

Purified oligosaccharide antigens such as oligomannosides can also be useful in determining the levels of ASCA-IgA and/or ASCA-IgG in a sample. The purified oligomannoside antigens are preferably converted into neoglycolipids as described in, for example, Faille et al., *Eur. J. Microbiol. Infect. Dis.*, 11:438-446 (1992). One skilled in the art understands that the reactivity of such an oligomannoside antigen with ASCA can be optimized by varying the mannosyl chain length (Frosh et al., *Proc Natl. Acad. Sci. USA*, 82:1194-1198 (1985)); the anomeric configuration (Fukazawa et al., In "Immunology of Fungal Disease," E. Kurstak (ed.), Marcel Dekker Inc., New York, pp. 37-62 (1989); Nishikawa et al., *Microbiol. Immunol.*, 34:825-840 (1990); Poulain et al., *Eur. J. Clin. Microbiol.*, 23:46-52 (1993); Shibata et al., *Arch. Biochem. Biophys.*, 243:338-348 (1985); Trinel et al., *Infect. Immun.*, 60:3845-3851 (1992)); or the position of the linkage (Kikuchi et al., *Planta*, 190:525-535 (1993)).

Suitable oligomannosides for use in the methods of the present invention include, without limitation, an oligomannoside having the mannotetraose Man(1-3) Man(1-2) Man(1-2) Man. Such an oligomannoside can be purified from PPM as described in, e.g., Faille et al., supra. An exemplary neoglycolipid specific for ASCA can be constructed by releasing the oligomannoside from its respective PPM and subsequently coupling the released oligomannoside to 4-hexadecylaniline or the like.

R. Anti-Microbial Antibodies

The determination of anti-OmpC antibody levels in a sample is also useful in the present invention. As used herein, the term "anti-outer membrane protein C antibody" or "anti-OmpC antibody" includes antibodies directed to a bacterial outer membrane porin as described in, e.g., PCT Patent Publication No. WO 01/89361. The term "outer membrane protein C" or "OmpC" refers to a bacterial porin that is immunoreactive with an anti-OmpC antibody.

The level of anti-OmpC antibody present in a sample from an individual can be determined using an OmpC protein or a fragment thereof such as an immunoreactive fragment thereof. Suitable OmpC antigens useful in determining anti-OmpC antibody levels in a sample include, without limitation, an OmpC protein, an OmpC polypeptide having substantially the same amino acid sequence as the OmpC protein, or a fragment thereof such as an immunoreactive fragment thereof. As used herein, an OmpC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpC protein, with the amino acid identity determined using a sequence alignment program such as CLUSTALW. Such antigens can be prepared, for example, by purification from enteric bacteria such as E. coli, by recombinant expression of a nucleic acid such as Genbank Accession No. K00541, by synthetic means such as solution or solid phase peptide synthesis, or by using phage display.

The determination of anti-I2 antibody levels in a sample is also useful in the present invention. As used herein, the term "anti-I2 antibody" includes antibodies directed to a microbial antigen sharing homology to bacterial transcriptional regulators as described in, e.g., U.S. Pat. No. 6,309,643. The term "I2" refers to a microbial antigen that is immunoreactive with an anti-I2 antibody. The microbial I2 protein is a polypeptide of 100 amino acids sharing some similarity weak homology with the predicted protein 4 from C. pasteurianum, Rv3557c from Mycobacterium tuberculosis, and a transcriptional regulator from Aquifex aeolicus. The nucleic acid and protein sequences for the I2 protein are described in, e.g., U.S. Pat. No. 6,309,643.

The level of anti-I2 antibody present in a sample from an individual can be determined using an I2 protein or a fragment thereof such as an immunoreactive fragment thereof. Suitable I2 antigens useful in determining anti-I2 antibody levels in a sample include, without limitation, an I2 protein, an I2 polypeptide having substantially the same amino acid sequence as the I2 protein, or a fragment thereof such as an immunoreactive fragment thereof. Such I2 polypeptides exhibit greater sequence similarity to the I2 protein than to the C. pasteurianum protein 4 and include isotype variants and homologs thereof. As used herein, an I2 polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring I12 protein, with the amino acid identity determined using a sequence alignment program such as CLUSTALW. Such I2 antigens can be prepared, for example, by purification from microbes, by recombinant expression of a nucleic acid encoding an I2 antigen, by synthetic means such as solution or solid phase peptide synthesis, or by using phage display.

The determination of anti-flagellin antibody levels in a sample is also useful in the present invention. As used herein, the term "anti-flagellin antibody" includes antibodies directed to a protein component of bacterial flagella as described in, e.g., PCT Patent Publication No. WO 03/053220 and U.S. Patent Publication No. 20040043931. The term "flagellin" refers to a bacterial flagellum protein that is immunoreactive with an anti-flagellin antibody. Microbial flagellins are proteins found in bacterial flagellum that arrange themselves in a hollow cylinder to form the filament.

The level of anti-flagellin antibody present in a sample from an individual can be determined using a flagellin protein or a fragment thereof such as an immunoreactive fragment thereof. Suitable flagellin antigens useful in determining anti-flagellin antibody levels in a sample include, without limitation, a flagellin protein such as Cbir-1 flagellin, flagellin X, flagellin A, flagellin B, fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared, e.g., by purification from bacterium such as Helicobacter Bilis, Helicobacter mustelae, Helicobacter pylori, Butyrivibrio fibrisolvens, and bacterium found in the cecum, by recombinant expression of a nucleic acid encoding a flagellin antigen, by synthetic means such as solution or solid phase peptide synthesis, or by using phage display.

S. Other Diagnostic Markers

The determination of the presence or level of lactoferrin in a sample is also useful in the present invention. In certain instances, the presence or level of lactoferrin is detected at the level of mRNA expression with an assay such as, for example, a hybridization assay or an amplification-based assay. In certain other instances, the presence or level of lactoferrin is detected at the level of protein expression using, for example, an immunoassay (e.g., ELISA) or an immunohistochemical assay. A lactoferrin ELISA kit available from Calbiochem (San Diego, Calif.) can be used to detect human lactoferrin in a plasma, urine, bronchoalveolar lavage, or cerebrospinal fluid sample. Similarly, an ELISA kit available from U.S. Biological (Swampscott, Mass.) can be used to determine the level of lactoferrin in a plasma sample. U.S. Patent Publication No. 20040137536 describes an ELISA assay for determining the presence of elevated lactoferrin levels in a stool sample. Likewise, U.S. Patent Publication No. 20040033537 describes an ELISA assay for determining the concentration of endogenous lactoferrin in a stool, mucus, or bile sample. In some embodiments, then presence or level of anti-lactoferrin antibodies can be detected in a sample using, e.g., lactoferrin protein or a fragment thereof.

Immunoassays such as ELISA are also particularly useful for determining the presence or level of C-reactive protein (CRP) in a sample. For example, a sandwich colorimetric ELISA assay available from Alpco Diagnostics (Salem, N.H.) can be used to determine the level of CRP in a serum, plasma, urine, or stool sample. Similarly, an ELISA kit available from Biomeda Corporation (Foster City, Calif.) can be used to detect CRP levels in a sample. Other methods for determining CRP levels in a sample are described in, e.g., U.S. Pat. Nos. 6,838,250 and 6,406,862; and U.S. Patent Publication Nos. 20060024682 and 20060019410.

In addition, hemoccult, fecal occult blood, is often indicative of gastrointestinal illness and various kits have been developed to monitor gastrointestinal bleeding. For example, Hemoccult SENSA, a Beckman Coulter product, is a diagnostic aid for gastrointestinal bleeding, iron deficiency, peptic ulcers, ulcerative colitis, and, in some instances, in screening for colorectal cancer. This particular assay is based on the oxidation of guaiac by hydrogen peroxide to produce a blue color. A similar colorimetric assay is commercially available from Helena Laboratories (Beaumont, Tex.) for the detection of blood in stool samples. Other methods for detecting occult blood in a stool sample by determining the presence or level of hemoglobin or heme activity are described in, e.g., U.S. Pat. Nos. 4,277,250, 4,920,045, 5,081,040, and 5,310,684.

The determination of the presence or level of fibrinogen or a proteolytic product thereof such as a fibrinopeptide in a sample is also useful in the present invention. Fibrinogen is a plasma glycoprotein synthesized in the liver composed of 3 structurally different subunits: alpha (FGA); beta (FGB); and gamma (FGG). Thrombin causes a limited proteolysis of the fibrinogen molecule, during which fibrinopeptides A and B are released from the N-terminal regions of the alpha and beta chains, respectively. Fibrinopeptides A and B, which have been sequenced in many species, may have a physiological role as vasoconstrictors and may aid in local hemostasis during blood clotting. In one embodiment, human fibrinopeptide A comprises the sequence: Ala-Asp-Ser-Gly-Glu-Gly-Asp-Phe-Leu-Ala-Glu-Gly-Gly-Gly-Val-Arg (SEQ ID NO:1). In another embodiment, human fibrinopeptide B comprises the sequence: Glp-Gly-Val-Asn-Asp-Asn-Glu-Glu-Gly-Phe-Phe-Ser-Ala-Arg (SEQ ID NO:2). An ELISA kit available from American Diagnostica Inc. (Stamford, Conn.) can be used to detect the presence or level of human fibrinopeptide A in plasma or other biological fluids.

In certain embodiments, the determination of the presence or level of calcitonin gene-related peptide (CGRP) in a sample is useful in the present invention. Calcitonin is a 32-amino acid peptide hormone synthesized by the parafollicular cells of the thyroid. It causes reduction in serum calcium, an effect opposite to that of parathyroid hormone. CGRP is derived, with calcitonin, from the CT/CGRP gene located on chromosome 11. CGRP is a 37-amino acid peptide and is a potent endogenous vasodilator. CGRP is primarily produced in nervous tissue; however, its receptors are expressed throughout the body. An ELISA kit available from Cayman Chemical Co. (Ann Arbor, Mich.) can be used to detect the presence or level of human CGRP in a variety of samples including plasma, serum, nervous tissue, CSF, and culture media.

In other embodiments, the determination of the presence or level of an anti-tissue transglutaminase (tTG) antibody in a sample is useful in the present invention. As used herein, the term "anti-tTG antibody" includes any antibody that recognizes tissue transglutaminase (tTG) or a fragment thereof. Transglutaminases are a diverse family of $Ca^{2+}$-dependent enzymes that are ubiquitous and highly conserved across species. Of all the transglutaminases, tTG is the most widely distributed. In certain instances, the anti-tTG antibody is an anti-tTG IgA antibody, anti-tTG IgG antibody, or mixtures thereof. An ELISA kit available from ScheBo Biotech USA Inc. (Marietta, Ga.) can be used to detect the presence or level of human anti-tTG IgA antibodies in a blood sample.

The determination of the presence of polymorphisms in the NOD2/CARD15 gene in a sample is also useful in the present invention. For example, polymorphisms in the NOD2 gene such as a C2107T nucleotide variant that results in a R703W protein variant can be identified in a sample from an individual (see, e.g., U.S. Patent Publication No. 20030190639). In an alternative embodiment, NOD2 mRNA levels can be used as a diagnostic marker of the present invention to aid in classifying IBS.

The determination of the presence of polymorphisms in the serotonin reuptake transporter (SERT) gene in a sample is also useful in the present invention. For example, polymorphisms in the promoter region of the SERT gene have effects on transcriptional activity, resulting in altered 5-HT reuptake efficiency. It has been shown that a strong genotypic association was observed between the SERT-P deletion/deletion genotype and the IBS phenotype (see, e.g., Yeo Gut, 53:1396-1399 (2004)). In an alternative embodiment, SERT mRNA levels can be used as a diagnostic marker of the present invention to aid in classifying IBS (see, e.g., Gershon, J. Clin. Gastroenterol., 39(5 Suppl.):5184-193 (2005)).

In certain aspects, the level of tryptophan hydroxylase-1 mRNA is a diagnostic marker. For example, tryptophan hydroxylase-1 mRNA has been shown to be significantly reduced in IBS (see, e.g., Coats, Gastroenterology, 126:1897-1899 (2004)). In certain other aspects, a lactulose breath test to measure methane, which is indicative of bacterial overgrowth, can be used as a diagnostic marker for IBS.

Additional diagnostic markers include, but are not limited to, L-selectin/CD62L, anti-U1-70 kDa autoantibodies, zona occludens 1 (ZO-1), vasoactive intestinal peptide (VIP), serum amyloid A, gastrin, NB3 gene polymorphisms, NCl1 gene polymorphisms, fecal leukocytes, α2A and α2C adrenoreceptor gene polymorphisms, IL-10 gene polymorphisms, TNF-α gene polymorphisms, TGF-β1 gene polymorphisms, α-adrenergic receptors, G-proteins, $5-HT_{2A}$ gene polymorphisms, 5-HTT LPR gene polymorphisms, $5-HT_4$ receptor gene polymorphisms, zonulin, and the 33-mer peptide (Shan et al., Science, 297:2275-2279 (2002); PCT Patent Publication No. WO 03/068170).

VI. Classification Markers

A variety of classification markers are suitable for use in the methods, systems, and code of the present invention for classifying IBS into a category, form, or clinical subtype such as, for example, IBS-constipation (IBS-C), IBS-diarrhea (IBS-D), IBS-mixed (IBS-M), IBS-alternating (IBS-A), or post-infectious IBS (IBS-PI). Examples of classification markers include, without limitation, any of the diagnostic markers described above (e.g., leptin, serotonin reuptake transporter (SERT), tryptophan hydroxylase-1,5-hydroxytryptamine (5-HT), tryptase, $PGE_2$, histamine, and the like), as well as antrum mucosal protein 8, keratin-8, claudin-8, zonulin, corticotropin-releasing hormone receptor-1 (CRHR1), corticotropin-releasing hormone receptor-2 (CRHR2), and the like.

Figure 11:
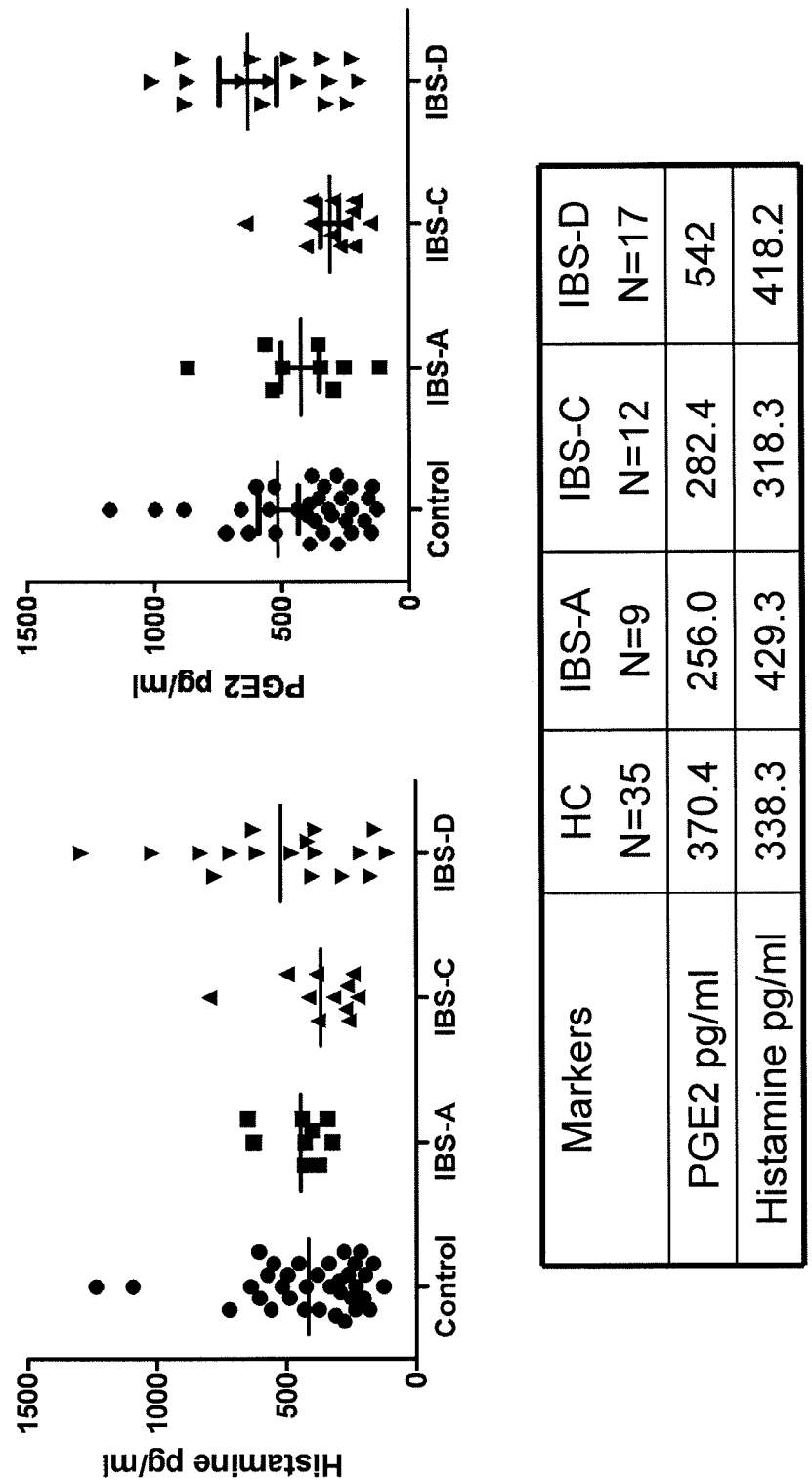
FIG. 11 illustrates the increased serum level of histamine and $PGE_2$ in IBS patients versus healthy controls.

For instance, Examples 1 and 2 below illustrate that measuring β-tryptase levels is particularly useful for distinguishing IBS-C patient samples from IBS-A and IBS-D patient samples. Similarly, Example 1 from US Patent Publication No. 2008/0085524, filed Aug. 14, 2007, which is herein incorporated by reference in its entirety for all purposes, illustrates that measuring leptin levels is particularly useful for distinguishing IBS-C patient samples from IBS-A and IBS-D patient samples. In addition, mucosal SERT and tryptophan hydroxylase-1 expression have been shown to be decreased in IBS-C and IBS-D (see, e.g., Gershon, J. Clin. Gastroenterol., 39(5 Suppl):5184-193 (2005)). Furthermore, IBS-C patients show impaired postprandial 5-HT release, whereas IBS-PI patients have higher peak levels of 5-HT (see, e.g., Dunlop, Clin Gastroenterol Hepatol., 3:349-357 (2005)). Furthermore, as can be seen in FIG. 11, serum levels of histamine and $PGE_2$ is also particularly useful for distinguishing IBS-D patient samples from IBS-A, IBS-C, and healthy control patient samples.

VII. Assays and Kits

Any of a variety of assays, techniques, and kits known in the art can be used to determine the presence or level of one or more markers in a sample to classify whether the sample is associated with IBS.

The present invention relies, in part, on determining the presence or level of at least one marker in a sample obtained from an individual. As used herein, the term "determining the presence of at least one marker" includes determining the presence of each marker of interest by using any quantitative or qualitative assay known to one of skill in the art. In certain instances, qualitative assays that determine the presence or absence of a particular trait, variable, or biochemical or serological substance (e.g., protein or antibody) are suitable for detecting each marker of interest. In certain other instances, quantitative assays that determine the presence or absence of RNA, protein, antibody, or activity are suitable for detecting each marker of interest. As used herein, the term "determining the level of at least one marker" includes determining the level of each marker of interest by using any direct or indirect quantitative assay known to one of skill in the art. In certain instances, quantitative assays that determine, for example, the relative or absolute amount of RNA, protein, antibody, or activity are suitable for determining the level of each marker of interest. One skilled in the art will appreciate that any assay useful for determining the level of a marker is also useful for determining the presence or absence of the marker.

As used herein, the term "antibody" includes a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or $F(ab')_2$ is included within the meaning of the term antibody.

Flow cytometry can be used to determine the presence or level of one or more markers in a sample. Such flow cytometric assays, including bead based immunoassays, can be used to determine, e.g., antibody marker levels in the same manner as described for detecting serum antibodies to *Candida albicans* and HIV proteins (see, e.g., Bishop and Davis, *J. Immunol. Methods,* 210:79-87 (1997); McHugh et al., *J. Immunol. Methods,* 116:213 (1989); Scillian et al., *Blood,* 73:2041 (1989)).

Phage display technology for expressing a recombinant antigen specific for a marker can also be used to determine the presence or level of one or more markers in a sample. Phage particles expressing an antigen specific for, e.g., an antibody marker can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.,* 267, San Diego: Academic Press, Inc. (1996)).

A variety of immunoassay techniques, including competitive and non-competitive immunoassays, can be used to determine the presence or level of one or more markers in a sample (see, e.g., Self and Cook, *Curr. Opin. Biotechnol.,* 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing and Nashabeh, *Electrophoresis,* 18:2184-2193 (1997); Bao, *J. Chromatogr. B. Biomed. Sci.,* 699:463-480 (1997)). Liposome immunoassays, such as flow-injection liposome immunoassays and liposome immunosensors, are also suitable for use in the present invention (see, e.g., Rongen et al., *J. Immunol. Methods,* 204:105-133 (1997)). In addition, nephelometry assays, in which the formation of protein/ antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.,* 27:261-276 (1989)).

Antigen capture ELISA can be useful for determining the presence or level of one or more markers in a sample. For example, in an antigen capture ELISA, an antibody directed to a marker of interest is bound to a solid phase and sample is added such that the marker is bound by the antibody. After unbound proteins are removed by washing, the amount of bound marker can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the marker is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for determining the presence or level of one or more markers in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

The immunoassays described above are particularly useful for determining the presence or level of one or more markers in a sample. As a non-limiting example, an ELISA using an IL-8-binding molecule such as an anti-IL-8 antibody or an extracellular IL-8-binding protein (e.g., IL-8 receptor) is useful for determining whether a sample is positive for IL-8 protein or for determining IL-8 protein levels in a sample. A fixed neutrophil ELISA is useful for determining whether a sample is positive for ANCA or for determining ANCA levels in a sample. Similarly, an ELISA using yeast cell wall phosphopeptidomannan is useful for determining whether a sample is positive for ASCA-IgA and/or ASCA-IgG, or for determining ASCA-IgA and/or ASCA-IgG levels in a sample. An ELISA using OmpC protein or a fragment thereof is useful for determining whether a sample is positive for anti-OmpC antibodies, or for determining anti-OmpC antibody levels in a sample. An ELISA using I2 protein or a fragment thereof is useful for determining whether a sample is positive for anti-I2 antibodies, or for determining anti-I2 antibody levels in a sample. An ELISA using flagellin protein (e.g., Cbir-1 flagellin) or a fragment thereof is useful for determining whether a sample is positive for anti-flagellin antibodies, or for determining anti-flagellin antibody levels in a sample. In addition, the immunoassays described above are particularly useful for determining the presence or level of other diagnostic markers in a sample.

Specific immunological binding of the antibody to the marker of interest can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Quantitative western blotting can also be used to detect or determine the presence or level of one or more markers in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.*, 28:669-675 (1998).

Alternatively, a variety of immunohistochemical assay techniques can be used to determine the presence or level of one or more markers in a sample. The term immunohistochemical assay encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, is useful for determining whether a sample is positive for ANCA, the level of ANCA in a sample, whether a sample is positive for pANCA, the level of pANCA in a sample, and/or an ANCA staining pattern (e.g., cANCA, pANCA, NSNA, and/or SAPPA staining pattern). The concentration of ANCA in a sample can be quantitated, e.g., through endpoint titration or through measuring the visual intensity of fluorescence compared to a known reference standard.

Alternatively, the presence or level of a marker of interest can be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, SELDI-TOF/MS, tandem MS, etc.). Qualitative or quantitative detection of a marker of interest can also be determined by well-known methods including, without limitation, Bradford assays, Coomassie blue staining, silver staining, assays for radiolabeled protein, and mass spectrometry.

The analysis of a plurality of markers may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of markers on a single surface. Particularly useful physical formats comprise surfaces having a plurality of discrete, addressable locations for the detection of a plurality of different markers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

In addition to the above-described assays for determining the presence or level of various markers of interest, analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., *Current Protocols in Molecular Biology*, John Wiley & Sons, Inc. New York (1999), Chapter 7 and Supplement 47; Theophilus et al., "PCR Mutation Detection Protocols," Humana Press, (2002); and Innis et al., *PCR Protocols*, San Diego, Academic Press, Inc. (1990). General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of the genotype of a marker such as a genetic marker can be performed using techniques known in the art including, without limitation, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell. Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), and sequencing by hybridization (Chee et al., *Science*, 274:610-614 (1996); Drmanac et al., *Science*, 260:1649-1652 (1993); Drmanac et al., *Nature Biotech.*, 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for genotyping an individual at a polymorphic site in a marker include, e.g., the INVADER® assay from Third Wave Technologies, Inc., restriction fragment length polymorphism (RFLP) analysis, allele-specific oligonucleotide hybridization, a heteroduplex mobility assay, and single strand conformational polymorphism (SSCP) analysis.

Several markers of interest may be combined into one test for efficient processing of a multiple of samples. In addition, one skilled in the art would recognize the value of testing multiple samples (e.g., at successive time points, etc.) from the same subject. Such testing of serial samples can allow the identification of changes in marker levels over time. Increases or decreases in marker levels, as well as the absence of change in marker levels, can also provide useful information to classify IBS or to rule out diseases and disorders associated with IBS-like symptoms.

A panel for measuring one or more of the markers described above may be constructed to provide relevant information related to the approach of the present invention for classifying a sample as being associated with IBS. Such a panel may be constructed to determine the presence or level of 1, 2, 3, 4, 5, 6, 7, 8, 9, 10, 11, 12, 13, 14, 15, 16, 17, 18, 19, 20, 25, 30, 35, 40, or more individual markers. The analysis of a single marker or subsets of markers can also be carried out by one skilled in the art in various clinical settings. These include, but are not limited to, ambulatory, urgent care, critical care, intensive care, monitoring unit, inpatient, outpatient, physician office, medical clinic, and health screening settings.

The analysis of markers could be carried out in a variety of physical formats as well. For example, the use of microtiter plates or automation could be used to facilitate the processing of large numbers of test samples. Alternatively, single sample formats could be developed to facilitate treatment and diagnosis in a timely fashion.

VIII. Statistical Algorithms

In some aspects, the present invention provides methods, assays, systems, and code for classifying whether a sample is associated with IBS using a statistical algorithm or process to classify the sample as an IBS sample or non-IBS sample. In other aspects, the present invention provides methods, systems, and code for classifying whether a sample is associated with IBS using a first statistical algorithm or process to classify the sample as a non-IBD sample or IBD sample (i.e., IBD rule-out step), followed by a second statistical algorithm or process to classify the non-IBD sample as an IBS sample or non-IBS sample (i.e., IBS rule-in step). Preferably, the statistical algorithms or processes independently comprise one or more learning statistical classifier systems. As described herein, a combination of learning statistical classifier systems advantageously provides improved sensitivity, specificity, negative predictive value, positive predictive value, and/or overall accuracy for classifying whether a sample is associated with IBS. In a preferred embodiment, the methods, assays, systems, and code provided herein use a combination of at least two statistical algorithms.

In some embodiments, the first statistical algorithm is a learning statistical classifier system selected from the group consisting of a random forest (RF), classification and regression tree (C&RT), boosted tree, neural network (NN), support vector machine (SVM), general chi-squared automatic interaction detector model, interactive tree, multiadaptive regression spline, machine learning classifier, and combinations thereof. In certain instances, the first statistical algorithm is a single learning statistical classifier system. Preferably, the single learning statistical classifier system comprises a tree-based statistical algorithm such as a RF or C&RT. In certain other instances, the first statistical algorithm is a combination of at least two learning statistical classifier systems, e.g., used in tandem or parallel. As a non-limiting example, a RF can first be used to generate a prediction or probability value based upon the diagnostic marker profile, alone or in combination with a symptom profile, and a NN (e.g., artificial NN) can then be used to classify the sample as a non-IBD sample or IBD sample based upon the prediction or probability value and the same or different diagnostic marker profile or combination of profiles. The hybrid RF/NN learning statistical classifier system of the present invention typically classifies the sample as a non-IBD sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In certain embodiments, the second statistical algorithm comprises any of the learning statistical classifier systems described above. In certain instances, the second statistical algorithm is a single learning statistical classifier system such as, for example, a tree-based statistical algorithm (e.g., RF or C&RT). In certain other instances, the second statistical algorithm is a combination of at least two learning statistical classifier systems, e.g., used in tandem or parallel. As a non-limiting example, a RF can first be used to generate a prediction or probability value based upon the diagnostic marker profile, alone or in combination with a symptom profile, and a NN (e.g., artificial NN) or SVM can then be used to classify the non-IBD sample as a non-IBS sample or IBS sample based upon the prediction or probability value and the same or different diagnostic marker profile or combination of profiles. The hybrid RF/NN or RF/SVM learning statistical classifier system described herein typically classifies the sample as an IBS sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

The term "statistical algorithm" or "statistical process" includes any of a variety of statistical analyses used to determine relationships between variables. In the present invention, the variables are the presence or level of at least one marker of interest and/or the presence or severity of at least one IBS-related symptom. Any number of markers and/or symptoms can be analyzed using a statistical algorithm described herein. For example, 1, 2, 3, 4, 5, 6, 7, 8, 9, 10, 11, 12, 13, 14, 15, 16, 17, 18, 19, 20, 25, 30, 35, 40, 45, 50, 55, 60, or more biomarkers and/or symptoms can be included in a statistical algorithm. In one embodiment, logistic regression is used. In another embodiment, linear regression is used. In certain instances, the statistical algorithms of the present invention can use a quantile measurement of a particular marker within a given population as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels, etc.) as variables in the algorithms (just as with continuous variables).

Preferably, the statistical algorithms of the present invention comprise one or more learning statistical classifier systems. As used herein, the term "learning statistical classifier system" includes a machine learning algorithmic technique capable of adapting to complex data sets (e.g., panel of markers of interest and/or list of IBS-related symptoms) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning*, 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the CART software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM-$^{light}$ software developed by Thorsten Joachims (Cornell University) or using the LIBSVM software developed by Chih-Chung Chang and Chih-Jen Lin (National Taiwan University).

The learning statistical classifier systems described herein can be trained and tested using a cohort of samples (e.g., serological samples) from healthy individuals, IBS patients, IBD patients, and/or Celiac disease patients. For example, samples from patients diagnosed by a physician, and preferably by a gastroenterologist as having IBD using a biopsy, colonoscopy, or an immunoassay as described in, e.g., U.S. Pat. No. 6,218,129, are suitable for use in training and testing the learning statistical classifier systems of the present invention. Samples from patients diagnosed with IBD can also be stratified into Crohn's disease or ulcerative colitis using an immunoassay as described in, e.g., U.S. Pat. Nos. 5,750,355 and 5,830,675. Samples from patients diagnosed with IBS using a published criteria such as the Manning, Rome I, Rome II, or Rome III diagnostic criteria are suitable for use in training and testing the learning statistical classifier systems of the present invention. Samples from healthy individuals can include those that were not identified as IBD and/or IBS samples. One skilled in the art will know of additional techniques and diagnostic criteria for obtaining a cohort of patient samples that can be used in training and testing the learning statistical classifier systems of the present invention.

As used herein, the term "sensitivity" refers to the probability that a diagnostic method, system, or code of the present invention gives a positive result when the sample is positive, e.g., having IBS. Sensitivity is calculated as the number of true positive results divided by the sum of the true positives and false negatives. Sensitivity essentially is a measure of how well a method, system, or code of the present invention correctly identifies those with IBS from those without the disease. The statistical algorithms can be selected such that the sensitivity of classifying IBS is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In preferred embodiments, the sensitivity of classifying IBS is at least about 90% when a combination of learning statistical classifier systems is used (see, Example 10 from US Patent Publication No. 2008/0085524, which is incorporated herein by reference in its entirety for all purposes) or at least about 85% when a single learning statistical classifier system is used (see, Example 11 from US Patent Publication No. 2008/0085524, which is incorporated herein by reference in its entirety for all purposes).

The term "specificity" refers to the probability that a diagnostic method, system, or code of the present invention gives a negative result when the sample is not positive, e.g., not having IBS. Specificity is calculated as the number of true negative results divided by the sum of the true negatives and false positives. Specificity essentially is a measure of how well a method, system, or code of the present invention excludes those who do not have IBS from those who have the disease. The statistical algorithms can be selected such that the specificity of classifying IBS is at least about 70%, for example, at least about 75%, 80%, 85%, 86%, 87%, 88%, 89%, 90%, 91%, 92%, 93%, 94%, 95%, 96%, 97%, 98%, or 99%. In preferred embodiments, the specificity of classifying IBS is at least about 86% when a combination of learning statistical classifier systems is used (see, Example 10 from US Patent Publication No. 2008/0085524, which is incorporated herein by reference in its entirety for all purposes) or at least about 84% when a single learning statistical classifier system is used (see, Example 11 from US Patent Publication No. 2008/0085524, which is incorporated herein by reference in its entirety for all purposes).

As used herein, the term "negative predictive value" or "NPV" refers to the probability that an individual identified as not having IBS actually does not have the disease. Negative predictive value can be calculated as the number of true negatives divided by the sum of the true negatives and false negatives. Negative predictive value is determined by the characteristics of the diagnostic method, system, or code as well as the prevalence of the disease in the population analyzed. The statistical algorithms can be selected such that the negative predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In preferred embodiments, the negative predictive value of classifying IBS is at least about 87% when a combination of learning statistical classifier systems is used (see, Example 10 from US Patent Publication No. 2008/0085524, which is incorporated herein by reference in its entirety for all purposes).

The term "positive predictive value" or "PPV" refers to the probability that an individual identified as having IBS actually has the disease. Positive predictive value can be calculated as the number of true positives divided by the sum of the true positives and false positives. Positive predictive value is determined by the characteristics of the diagnostic method, system, or code as well as the prevalence of the disease in the population analyzed. The statistical algorithms can be selected such that the positive predictive value in a population having a disease prevalence is in the range of about 80% to about 99% and can be, for example, at least about 80%, 85%, 86%, 87%, 88%, 89%, 90%, 91%, 92%, 93%, 94%, 95%, 96%, 97%, 98%, or 99%. In preferred embodiments, the positive predictive value of classifying IBS is at least about 90% when a combination of learning statistical classifier systems is used (see, Example 10 from US Patent Publication No. 2008/0085524, which is incorporated herein by reference in its entirety for all purposes).

Predictive values, including negative and positive predictive values, are influenced by the prevalence of the disease in the population analyzed. In the methods, systems, and code of the present invention, the statistical algorithms can be selected to produce a desired clinical parameter for a clinical population with a particular IBS prevalence. For example, learning statistical classifier systems can be selected for an IBS prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

As used herein, the term "overall agreement" or "overall accuracy" refers to the accuracy with which a method, system, or code of the present invention classifies a disease state.

Overall accuracy is calculated as the sum of the true positives and true negatives divided by the total number of sample results and is affected by the prevalence of the disease in the population analyzed. For example, the statistical algorithms can be selected such that the overall accuracy in a patient population having a disease prevalence is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In preferred embodiments, the overall accuracy of classifying IBS is at least about 80% when a combination of learning statistical classifier systems is used (see, Example 10 from US Patent Publication No. 2008/0085524, which is incorporated herein by reference in its entirety for all purposes).

IX. Disease Classification System

Figure 13:
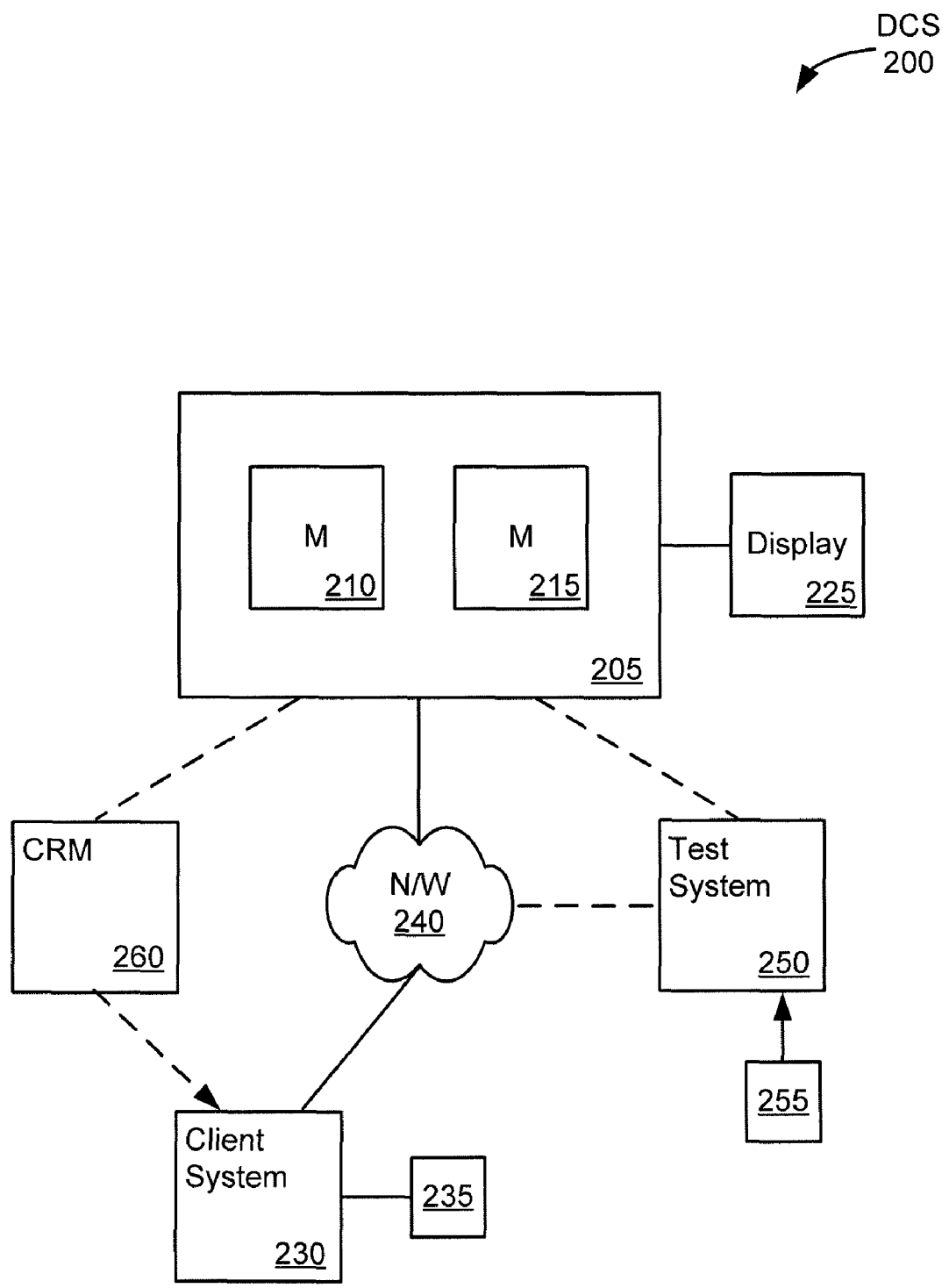
FIG. 13 illustrates a disease classification system (DCS) according to one embodiment of the present invention.

FIG. 13 illustrates a disease classification system (DCS) (200) according to one embodiment of the present invention. As shown therein, a DCS includes a DCS intelligence module (205), such as a computer, having a processor (215) and memory module (210). The intelligence module also includes communication modules (not shown) for transmitting and receiving information over one or more direct connections (e.g., USB, Firewire, or other interface) and one or more network connections (e.g., including a modem or other network interface device). The memory module may include internal memory devices and one or more external memory devices. The intelligence module also includes a display module (225), such as a monitor or printer. In one aspect, the intelligence module receives data such as patient test results from a data acquisition module such as a test system (250), either through a direct connection or over a network (240). For example, the test system may be configured to run multianalyte tests on one or more patient samples (255) and automatically provide the test results to the intelligence module. The data may also be provided to the intelligence module via direct input by a user or it may be downloaded from a portable medium such as a compact disk (CD) or a digital versatile disk (DVD). The test system may be integrated with the intelligence module, directly coupled to the intelligence module, or it may be remotely coupled with the intelligence module over the network. The intelligence module may also communicate data to and from one or more client systems (230) over the network as is well known. For example, a requesting physician or healthcare provider may obtain and view a report from the intelligence module, which may be resident in a laboratory or hospital, using a client system (230).

The network can be a LAN (local area network), WAN (wide area network), wireless network, point-to-point network, star network, token ring network, hub network, or other configuration. As the most common type of network in current use is a TCP/IP (Transfer Control Protocol and Internet Protocol) network such as the global internetwork of networks often referred to as the "Internet" with a capital "I," that will be used in many of the examples herein, but it should be understood that the networks that the present invention might use are not so limited, although TCP/IP is the currently preferred protocol.

Figure 2:
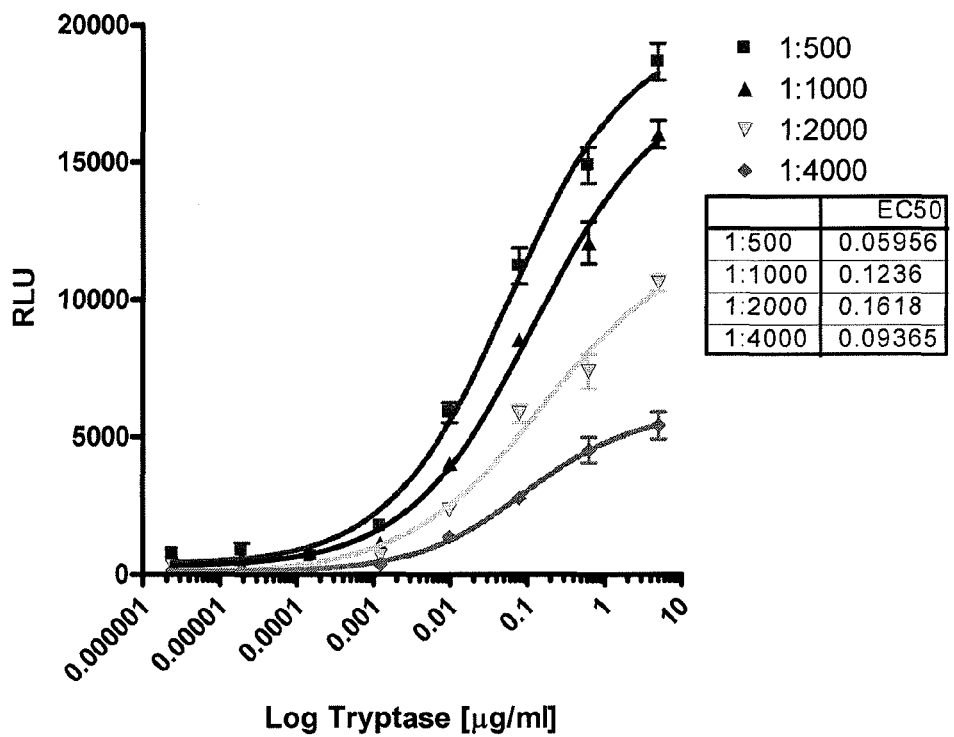
FIG. 2 illustrates a dose response curve in one embodiment of the present invention.
Figure 3:
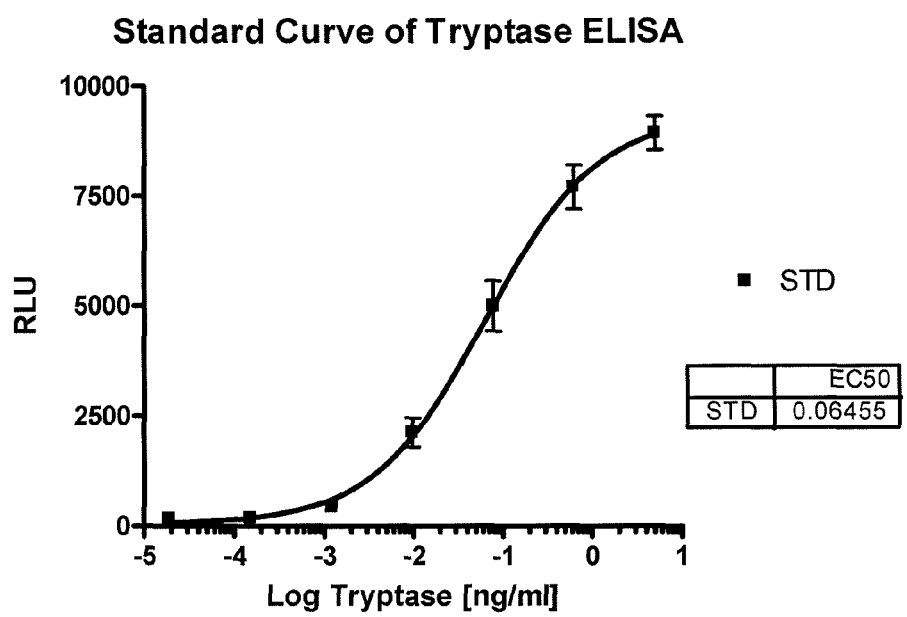
FIG. 3 illustrates a standard curve in one embodiment of the present invention. Rabbit anti-human tryptase was coated onto an immunoassay plate and blocked with assay buffer (5% BSA in PBS). Different concentrations of human tryptase (Standard curve) or human serum samples (diluted in assay buffer 1:5 and 1:10) were added to the wells and incubated for 2 hours at RT. The plate was washed and alkaline phosphatase (AP) labeled McAb against tryptase (G3) were added and incubated for 2 hours at RT. The plate was washed and AP substrate (CSPD) was added to each well. A luminescence plate reader was used to detect the luminescent light. Serum tryptase concentration was calculated using the standard curve. (Tryptase detection range 0.019-5000 ng/ml. EC50=65 ng/ml; Recovery 81.5% with 20 ng/ml of tryptase spiked in normal pooled serum). See Example 16.
Figure 4:
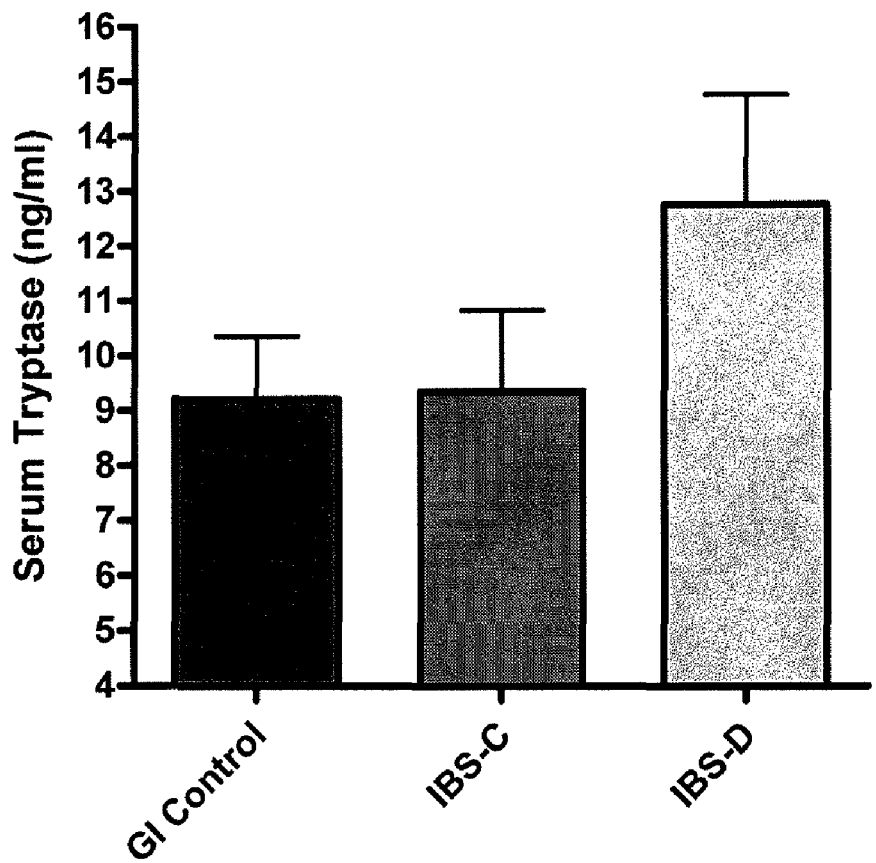
FIG. 4 illustrates a bar graph with tryptase concentrations in serum of GI control, IBS-C and IBS-D.
Figure 5:
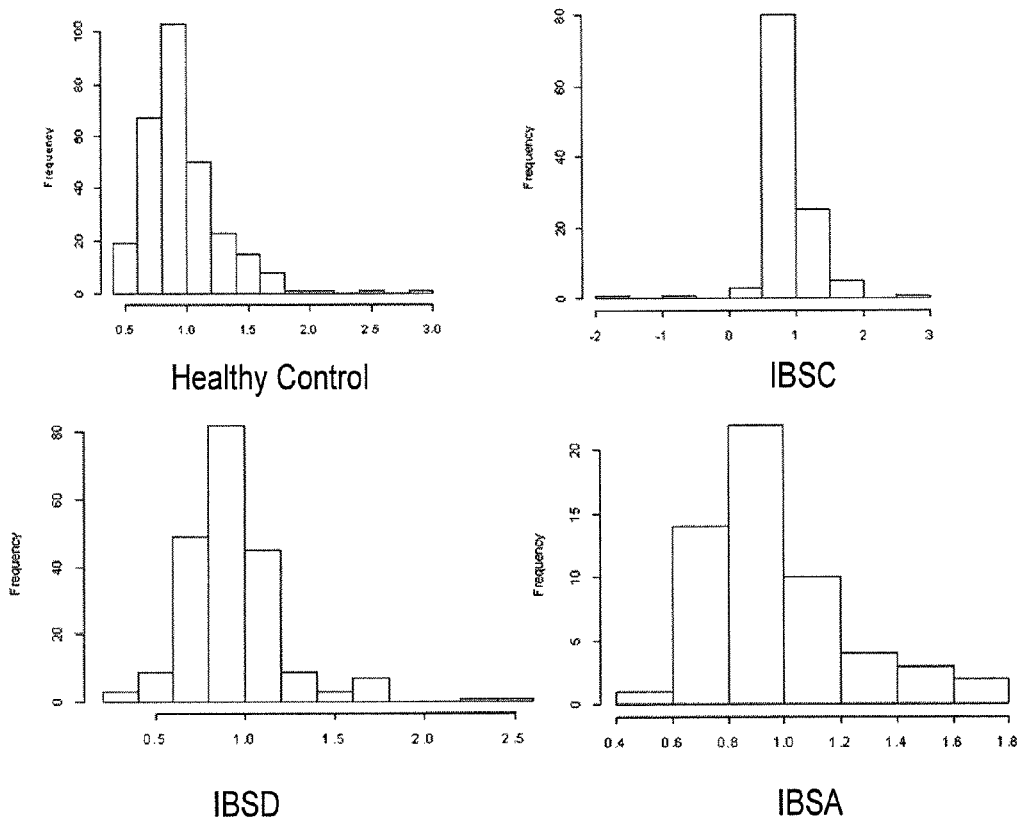
FIG. 5 illustrates a bar graph with tryptase log value distribution.
Figure 6:
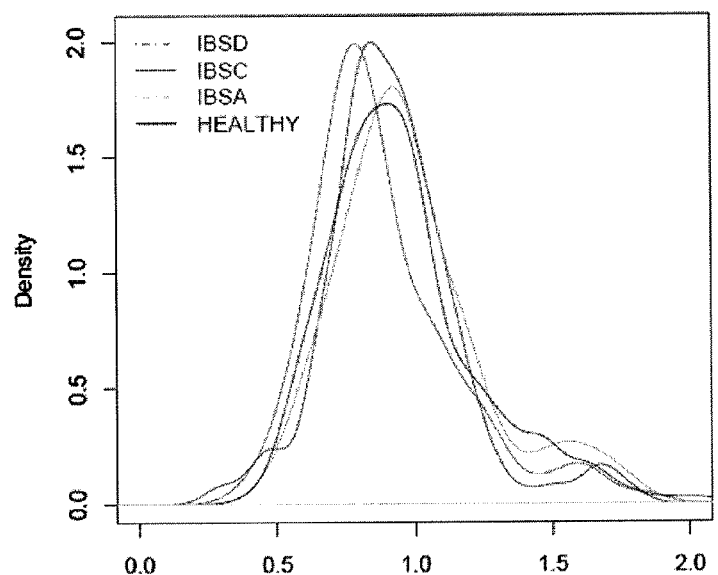
FIG. 6 illustrates a density analysis for tryptase data.
Figure 7:
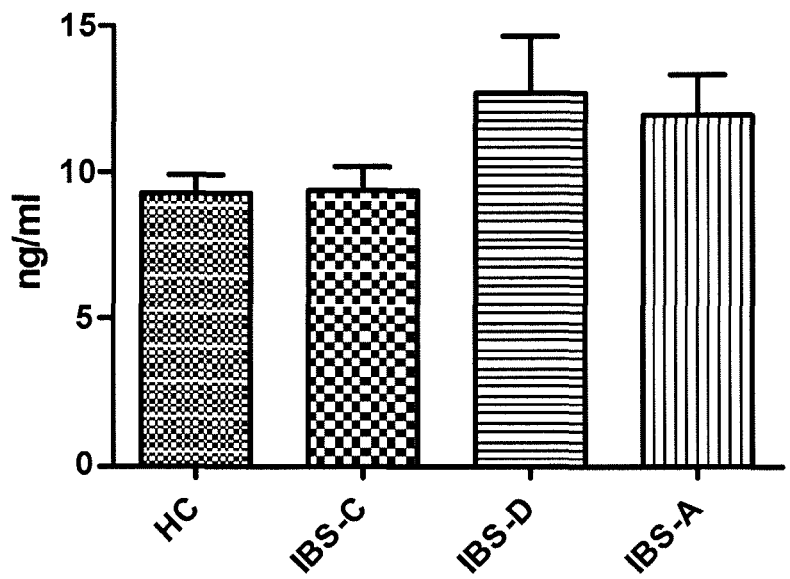
FIG. 7 illustrates a bar graph with tryptase concentrations in serum of GI control, IBS-C, IBS-D and IBS-A.

Several elements in the system shown in FIG. 2 from US Patent Publication No. 2008/0085524 may include conventional, well-known elements that need not be explained in detail here. For example, the intelligence module could be implemented as a desktop personal computer, workstation, mainframe, laptop, etc. Each client system could include a desktop personal computer, workstation, laptop, PDA, cell phone, or any WAP-enabled device or any other computing device capable of interfacing directly or indirectly to the Internet or other network connection. A client system typically runs an HTTP client, e.g., a browsing program, such as Microsoft's Internet Explorer™ browser, Netscape's Navigator™ browser, Opera's browser, or a WAP-enabled browser in the case of a cell phone, PDA or other wireless device, or the like, allowing a user of the client system to access, process, and view information and pages available to it from the intelligence module over the network. Each client system also typically includes one or more user interface devices, such as a keyboard, a mouse, touch screen, pen or the like, for interacting with a graphical user interface (GUI) provided by the browser on a display (e.g., monitor screen, LCD display, etc.) (235) in conjunction with pages, forms, and other information provided by the intelligence module. As discussed above, the present invention is suitable for use with the Internet, which refers to a specific global internetwork of networks. However, it should be understood that other networks can be used instead of the Internet, such as an intranet, an extranet, a virtual private network (VPN), a non-TCP/IP based network, any LAN or WAN, or the like.

According to one embodiment, each client system and all of its components are operator configurable using applications, such as a browser, including computer code run using a central processing unit such as an Intel® Pentium® processor or the like. Similarly, the intelligence module and all of its components might be operator configurable using application(s) including computer code run using a central processing unit (215) such as an Intel Pentium processor or the like, or multiple processor units. Computer code for operating and configuring the intelligence module to process data and test results as described herein is preferably downloaded and stored on a hard disk, but the entire program code, or portions thereof, may also be stored in any other volatile or non-volatile memory medium or device as is well known, such as a ROM or RAM, or provided on any other computer readable medium (260) capable of storing program code, such as a compact disk (CD) medium, digital versatile disk (DVD) medium, a floppy disk, ROM, RAM, and the like.

The computer code for implementing various aspects and embodiments of the present invention can be implemented in any programming language that can be executed on a computer system such as, for example, in C, C++, C#, HTML, Java, JavaScript, or any other scripting language, such as VBScript. Additionally, the entire program code, or portions thereof, may be embodied as a carrier signal, which may be transmitted and downloaded from a software source (e.g., server) over the Internet, or over any other conventional network connection as is well known (e.g., extranet, VPN, LAN, etc.) using any communication medium and protocols (e.g., TCP/IP, HTTP, HTTPS, Ethernet, etc.) as are well known.

According to one embodiment, the intelligence module implements a disease classification process for analyzing patient test results and/or questionnaire responses to determine whether a patient sample is associated with IBS. The data may be stored in one or more data tables or other logical data structures in memory (210) or in a separate storage or database system coupled with the intelligence module. One or more statistical processes are typically applied to a data set including test data for a particular patient. For example, the test data might include a diagnostic marker profile, which comprises data indicating the presence or level of at least one marker in a sample from the patient. The test data might also include a symptom profile, which comprises data indicating the presence or severity of at least one symptom associated with IBS that the patient is experiencing or has recently experienced. In one aspect, a statistical process produces a statistically derived decision classifying the patient sample as an IBS sample or non-IBS sample based upon the diagnostic marker profile and/or symptom profile. In another aspect, a first statistical process produces a first statistically derived decision classifying the patient sample as an IBD sample or non-IBD sample based upon the diagnostic marker profile and/or symptom profile. If the patient sample is classified as a non-IBD sample, a second statistical process is applied to the same or a different data set to produce a second statistically derived decision classifying the non-IBD sample as an IBS sample or non-IBS sample. The first and/or the second statistically derived decision may be displayed on a display device associated with or coupled to the intelligence module, or the decision(s) may be provided to and displayed at a separate system, e.g., a client system (230). The displayed results allow a physician to make a reasoned diagnosis or prognosis.

X. Therapy and Therapeutic Monitoring

Once a sample from an individual has been classified as an IBS sample, the methods, systems, and code of the present invention can further comprise administering to the individual a therapeutically effective amount of a drug useful for treating one or more symptoms associated with IBS (i.e., an IBS drug). For therapeutic applications, the IBS drug can be administered alone or co-administered in combination with one or more additional IBS drugs and/or one or more drugs that reduce the side-effects associated with the IBS drug.

IBS drugs can be administered with a suitable pharmaceutical excipient as necessary and can be carried out via any of the accepted modes of administration. Thus, administration can be, for example, intravenous, topical, subcutaneous, transcutaneous, transdermal, intramuscular, oral, buccal, sublingual, gingival, palatal, intra-joint, parenteral, intra-arteriole, intradermal, intraventricular, intracranial, intraperitoneal, intralesional, intranasal, rectal, vaginal, or by inhalation. By "co-administer" it is meant that an IBS drug is administered at the same time, just prior to, or just after the administration of a second drug (e.g., another IBS drug, a drug useful for reducing the side-effects of the IBS drug, etc.).

A therapeutically effective amount of an IBS drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an IBS drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the IBS drug.

Methods for preparing such dosage forms are known to those skilled in the art (see, e.g., *REMINGTON'S PHARMACEUTICAL SCIENCES*, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *REMINGTON'S PHARMACEUTICAL SCIENCES*, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an IBS drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An IBS drug can also be formulated into a suppository disposed, for example, in a polyethylene glycol (PEG) carrier.

Liquid dosage forms can be prepared by dissolving or dispersing an IBS drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An IBS drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an IBS drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In therapeutic use for the treatment of IBS, an IBS drug can be administered at the initial dosage of from about 0.001 mg/kg to about 1000 mg/kg daily. A daily dose range of from about 0.01 mg/kg to about 500 mg/kg, from about 0.1 mg/kg to about 200 mg/kg, from about 1 mg/kg to about 100 mg/kg, or from about 10 mg/kg to about 50 mg/kg, can be used. The dosages, however, may be varied depending upon the requirements of the individual, the severity of IBS symptoms, and the IBS drug being employed. For example, dosages can be empirically determined considering the severity of IBS symptoms in an individual classified as having IBS according to the methods described herein. The dose administered to an individual, in the context of the present invention, should be sufficient to affect a beneficial therapeutic response in the individual over time. The size of the dose can also be determined by the existence, nature, and extent of any adverse side-effects that accompany the administration of a particular IBS drug in an individual. Determination of the proper dosage for a particular situation is within the skill of the practitioner. Generally, treatment is initiated with smaller dosages which are less than the optimum dose of the IBS drug. Thereafter, the dosage is increased by small increments until the optimum effect under circumstances is reached. For convenience, the total daily dosage may be divided and administered in portions during the day, if desired.

As used herein, the term "IBS drug" includes all pharmaceutically acceptable forms of a drug that is useful for treating one or more symptoms associated with IBS. For example, the IBS drug can be in a racemic or isomeric mixture, a solid complex bound to an ion exchange resin, or the like. In addition, the IBS drug can be in a solvated form. The term "IBS drug" is also intended to include all pharmaceutically acceptable salts, derivatives, and analogs of the IBS drug being described, as well as combinations thereof. For example, the pharmaceutically acceptable salts of an IBS drug include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of an IBS drug is suitable for use in the methods of the present invention, e.g., a pharmaceutically acceptable salt of an IBS drug, a free base of an IBS drug, or a mixture thereof.

Suitable drugs that are useful for treating one or more symptoms associated with IBS include, but are not limited to, serotonergic agents, antidepressants, chloride channel activators, chloride channel blockers, guanylate cyclase agonists, antibiotics, opioids, neurokinin antagonists, antispasmodic or anticholinergic agents, belladonna alkaloids, barbiturates, glucagon-like peptide-1 (GLP-1) analogs, corticotropin releasing factor (CRF) antagonists, probiotics, free bases thereof, pharmaceutically acceptable salts thereof, derivatives thereof, analogs thereof, and combinations thereof. Other IBS drugs include bulking agents, dopamine antagonists, carminatives, tranquilizers, dextofisopam, phenyloin, timolol, and diltiazem.

Serotonergic agents are useful for the treatment of IBS symptoms such as constipation, diarrhea, and/or alternating constipation and diarrhea. Non-limiting examples of serotonergic agents are described in Cash et al., *Aliment. Pharmacol. Ther.*, 22:1047-1060 (2005), and include 5-HT$_3$ receptor agonists (e.g., MKC-733, etc.), 5-HT$_4$ receptor agonists (e.g., tegaserod (Zelnorm™), prucalopride, AG1-001, etc.), 5-HT$_3$ receptor antagonists (e.g., alosetron (Lotronex®), cilansetron, ondansetron, granisetron, dolasetron, ramosetron, palonosetron, E-3620, DDP-225, DDP-733, etc.), mixed 5-HT$_3$ receptor antagonists/5-HT$_4$ receptor agonists (e.g., cisapride, mosapride, renzapride, etc.), free bases thereof, pharmaceutically acceptable salts thereof, derivatives thereof, analogs thereof, and combinations thereof. Additionally, amino acids like glutamine and glutamic acid which regulate intestinal permeability by affecting neuronal or glial cell signaling can be administered to treat patients with IBS.

Antidepressants such as selective serotonin reuptake inhibitor (SSRI) or tricyclic antidepressants are particularly useful for the treatment of IBS symptoms such as abdominal pain, constipation, and/or diarrhea. Non-limiting examples of SSRI antidepressants include citalopram, fluvoxamine, paroxetine, fluoxetine, sertraline, free bases thereof, pharmaceutically acceptable salts thereof, derivatives thereof, analogs thereof, and combinations thereof. Examples of tricyclic antidepressants include, but are not limited to, desipramine, nortriptyline, protriptyline, amitriptyline, clomipramine, doxepin, imipramine, trimipramine, maprotiline, amoxapine, clomipramine, free bases thereof, pharmaceutically acceptable salts thereof, derivatives thereof, analogs thereof, and combinations thereof.

Chloride channel activators are useful for the treatment of IBS symptoms such as constipation. A non-limiting example of a chloride channel activator is lubiprostone (Amitiza™), a free base thereof, a pharmaceutically acceptable salt thereof, a derivative thereof, or an analog thereof. In addition, chloride channel blockers such as crofelemer are useful for the treatment of IBS symptoms such as diarrhea. Guanylate cyclase agonists such as MD-1100 are useful for the treatment of constipation associated with IBS (see, e.g., Bryant et al., *Gastroenterol.*, 128:A-257 (2005)). Antibiotics such as neomycin can also be suitable for use in treating constipation associated with IBS (see, e.g., Park et al., *Gastroenterol.*, 128:A-258 (2005)). Non-absorbable antibiotics like rifaximin (Xifaxan™) are suitable to treat small bowel bacterial overgrowth and/or constipation associated with IBS (see, e.g., Sharara et al., *Am. J. Gastroenterol.*, 101:326-333 (2006)).

Opioids such as kappa opiods (e.g., asimadoline) may be useful for treating pain and/or constipation associated with IBS. Neurokinin (NK) antagonists such as talnetant, saredutant, and other NK2 and/or NK3 antagonists may be useful for treating IBS symptoms such as oversensitivity of the muscles in the colon, constipation, and/or diarrhea. Antispasmodic or anticholinergic agents such as dicyclomine may be useful for treating IBS symptoms such as spasms in the muscles of the gut and bladder. Other antispasmodic or anticholinergic agents such as belladonna alkaloids (e.g., atropine, scopolamine, hyoscyamine, etc.) can be used in combination with barbiturates such as phenobarbital to reduce bowel spasms associated with IBS. GLP-1 analogs such as GTP-010 may be useful for treating IBS symptoms such as constipation. CRF antagonists such as astressin and probiotics such as VSL#3® may be useful for treating one or more IBS symptoms. One skilled in the art will know of additional IBS drugs currently in use or in development that are suitable for treating one or more symptoms associated with IBS.

An individual can also be monitored at periodic time intervals to assess the efficacy of a certain therapeutic regimen once a sample from the individual has been classified as an IBS sample. For example, the levels of certain markers change based on the therapeutic effect of a treatment such as a drug. The patient is monitored to assess response and understand the effects of certain drugs or treatments in an individualized approach. Additionally, patients may not respond to a drug, but the markers may change, suggesting that these patients belong to a special population (not responsive) that can be identified by their marker levels. These patients can be discontinued on their current therapy and alternative treatments prescribed.

XI. Examples

The following examples are offered to illustrate, but not to limit, the claimed invention.

The Examples from US Patent Publication No. 2008/0085524, filed Aug. 14, 2007, are herein incorporated by reference in their entirety for all purposes.

A. Example 1

A Tryptase ELISA for Predicting IBS

This example describes a sensitive ELISA for detecting the presence or level of mast cell β-tryptase. See also, FIGS. 1-7.

Background: Mast cells play an important role in the pathogenesis of irritable bowel syndrome (IBS). Increased mast cell infiltration and activation in distal gut segments are associated with symptom onset and severity of IBS. Mast cells have been implicated in the elevated response of visceral afferent nerves to mucosal stimulus in IBS patients. Measurement of mast cell markers can have important implication in clinical diagnosis of IBS. However this effort was hindered due to lack of sensitive assays.

Methods: Here we report the development and validation of a highly sensitive two-side ELISA assay to measure tryptase level in human serum samples (detection limit 0.019 ng/ml). The assay is precise, robust, and reproducible. Serum tryptase concentration in healthy controls and IBS patients was measured using this assay.

Results: The average serum tryptase level in healthy controls was 9.32±2.1 ng/ml (n=156). IBS-D and IBS-A patients showed significant higher serum tryptase concentration (12.71 ng/ml (n=209) for IBS-D and 11.94 ng/ml (n=57) for IBS-A, p<0.01); while the average tryptase level is 9.34 ng/ml (n=118) for IBS-C, which has no significant difference from healthy controls for IBS-C.

Conclusion: This is the first biomarker developed so far that differentiates IBS-D and IBS-A patients from IBS-C patients and healthy controls. Combining serum tryptase level with other Prometheus IBS biomarkers, we were able to improve the accuracy of diagnosing IBS-D and IBS-A patients.

An ELISA assay was developed for the determination of serum mast cell β-tryptase level using rabbit anti-tryptase as capture antibody and alkaline phosphatase conjugated G3 as detecting antibody. Luminescent substrate CPSD (disodium 3-(4-methoxyspiro{1,2-dioxetane-3,2'-(5'-chloro)tricyclo[3.3.1.13,7]decan}-4-yl)phenyl phosphate), was used to enhance the assay sensitivity. Linear dose-response curve was observed over the standard range of 1-1000 ng/ml for β-tryptase in buffer with 5% BSA and 10% normal human serum. The low limit of the assay was 0.019 ng/ml, the intra-assay and inter-assay coefficients of variation were below 15% at 1 ng/ml and 1000 ng/ml tryptase concentrations. The recovery of known amounts of purified tryptase added to serum was 88%. The immunoassay was utilized to examine serum levels of tryptase from healthy controls, IBS-C and IBS-D patients. Average serum tryptase level in healthy control was 7.0+2.1 ng/ml (n=113). The average tryptase level in IBS-C and IBS-D were 9.6 ng/ml (n=116) and 12.7 (n=209) respectively. Using the cutoff value of 11.4 ng/ml (average+ 2SD), the assay specificity for GI healthy control was 82% (n=156), the assay sensitivity for IBS-C and IBS-D were 21.5% and 24.9% respectively. Combine with symptoms of the patient and other markers for IBS, serum tryptase levels may help differentiate IBS-D from other types of irritable bowel syndrome.

B. Example 2

Evaluation of the Diagnostic Utility of Serum Tryptase Levels in IBS

Background: Mast cells play an important role in the pathogenesis of irritable bowel syndrome (IBS). Increased mast cell infiltration and activation in distal gut segments are associated with symptom onset and severity of IBS. Mast cells have been implicated in the elevated response of visceral afferent nerves to mucosal stimulus in IBS patients. Measurement of mast cell markers can have important implications in clinical diagnosis of IBS. However, this effort was hindered due to lack of sensitive assays.

Methods: Here we report the development and validation of a highly sensitive two-site ELISA assay to measure tryptase level in human serum samples (detection limit 0.019 ng/ml). The assay is precise, robust, and reproducible. Serum tryptase concentrations in healthy controls and IBS patients was measured using this assay.

Results: The average serum tryptase level in healthy controls was 7.1±2.5 ng/ml. IBS-D and IBS-A patients showed higher serum tryptase concentrations (10.3±8.7 ng/ml for IBS-D and 12.1±10.7 ng/ml for IBS-A) than the healthy control subjects, while the average tryptase level was 9.6±9.4 ng/ml for IBS-C. There was a statistical difference of serum tryptase levels between the IBS-C and IBS-D groups ($p<0.01$).

Conclusion: Serum tryptase concentration is the first biomarker developed so far that differentiates IBS-D from IBS-C patients. Serum tryptase levels can be combined with other IBS biomarkers to improve the accuracy of diagnosing IBS.

Figure 8:
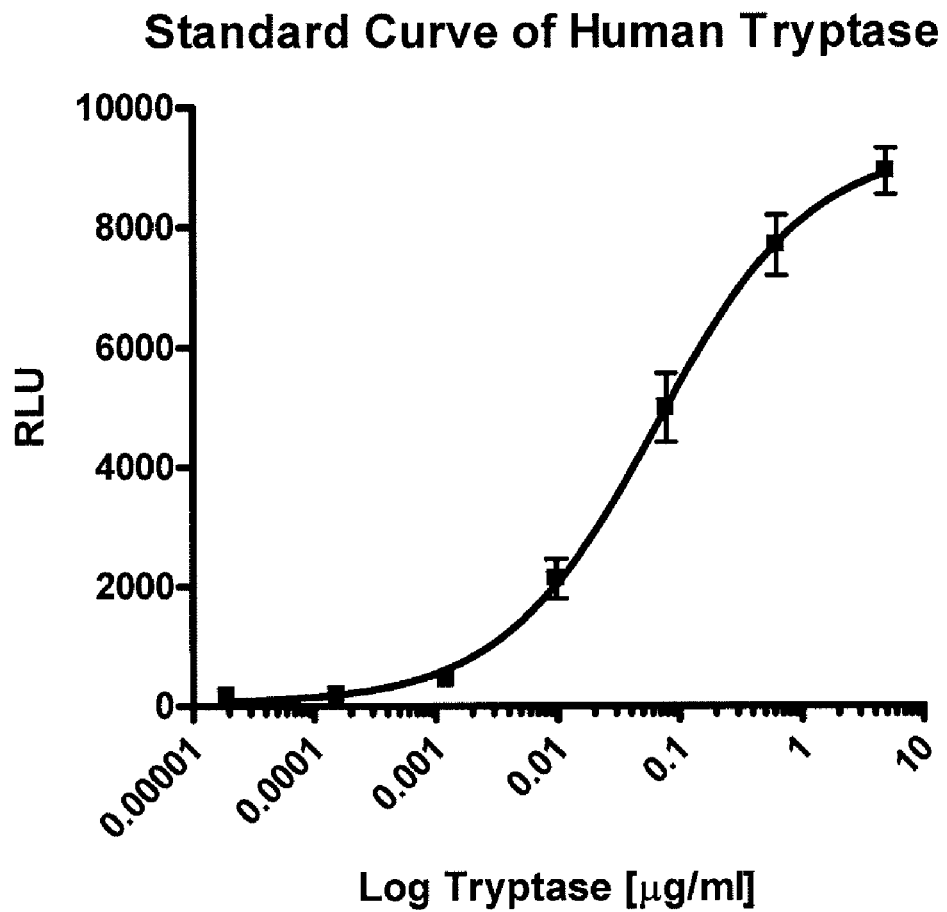
FIG. 8 illustrates the dose response curve of human tryptase in one embodiment of the present invention.

FIG. 8 shows the dose-dependent responses of human tryptase in the tryptase ELISA described herein. Protocol: A 96-well microtiter plate was coated with 100 ml of 2 mg/ml of anti-human tryptase antibody in sodium carbonate (pH 9.6) at 4° C. overnight. After washing with PBST, the plate was incubated with 300 ml/well of blocking/assay buffer (5% BSA in PBS) at room temperature (RT) for 30 minutes with gentle agitation. After washing, 100 ml/well of serially diluted (1:8 in assay buffer) human tryptase were added to the plate. After incubating at RT for another 2 hours, the plate was washed, and then incubated with 100 ml of AP-conjugated anti-human tryptase at an optimized dilution in assay buffer. The plate was incubated for 2 hours with gentle agitation and then washed. 100 ml of Tropix CSPD substrate was added to each well and incubated in the dark for 30 minutes before reading the luminescence with a luminescence plate reader. The Relative Luminescent Unit (RLU) and the tryptase concentration was plotted with the Prism Graphpad Program. Tryptase detection range=0.019-5000 ng/ml. EC50=65 ng/ml. Recovery was 81.5% with 20 ng spiked in normal pooled serum.

Figure 9A:
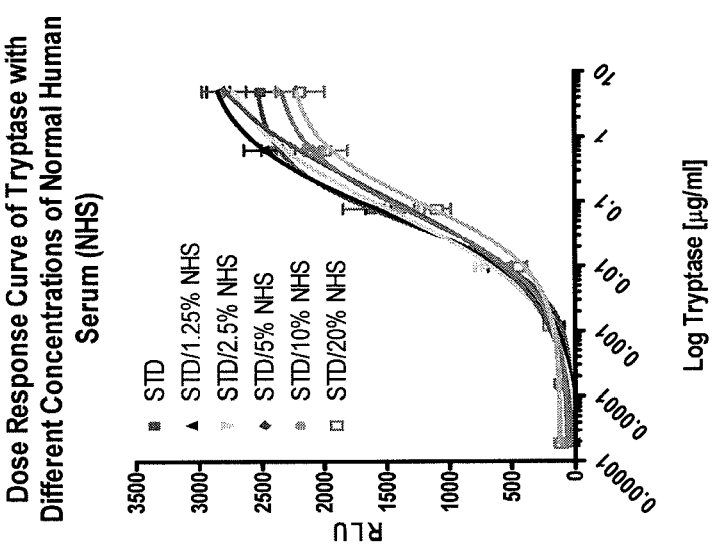
FIG. 9 illustrates the optimization of the tryptase ELISA. (A) Comparison of tryptase standard curve with different amount of capture antibody. (B) Optimization of detecting antibody dilutions. (C) Comparison of tryptase standard curves in the presence of different amounts of normal human serum (NHS).
Figure 9B:
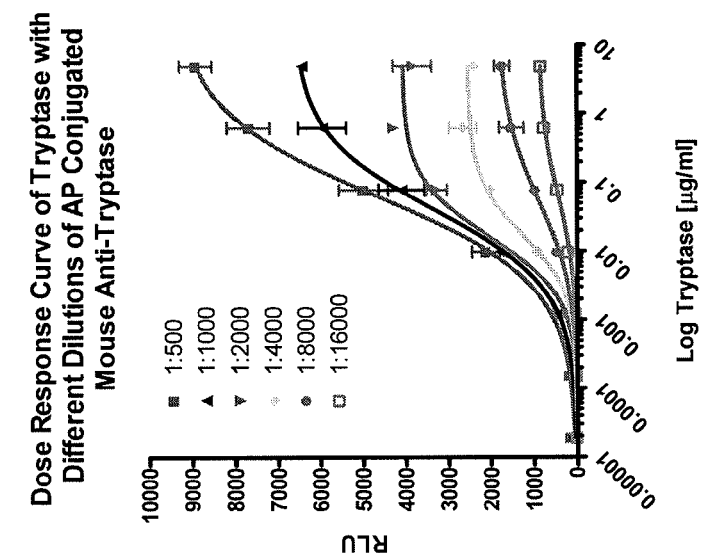
Figure 9C:
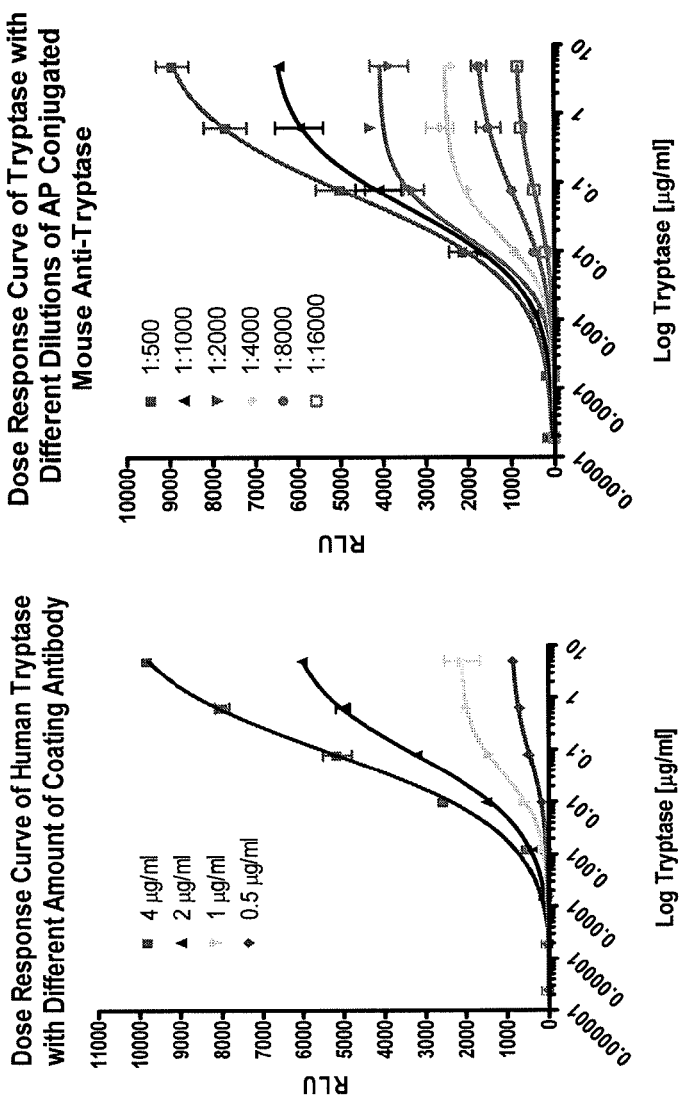
Figure 10:
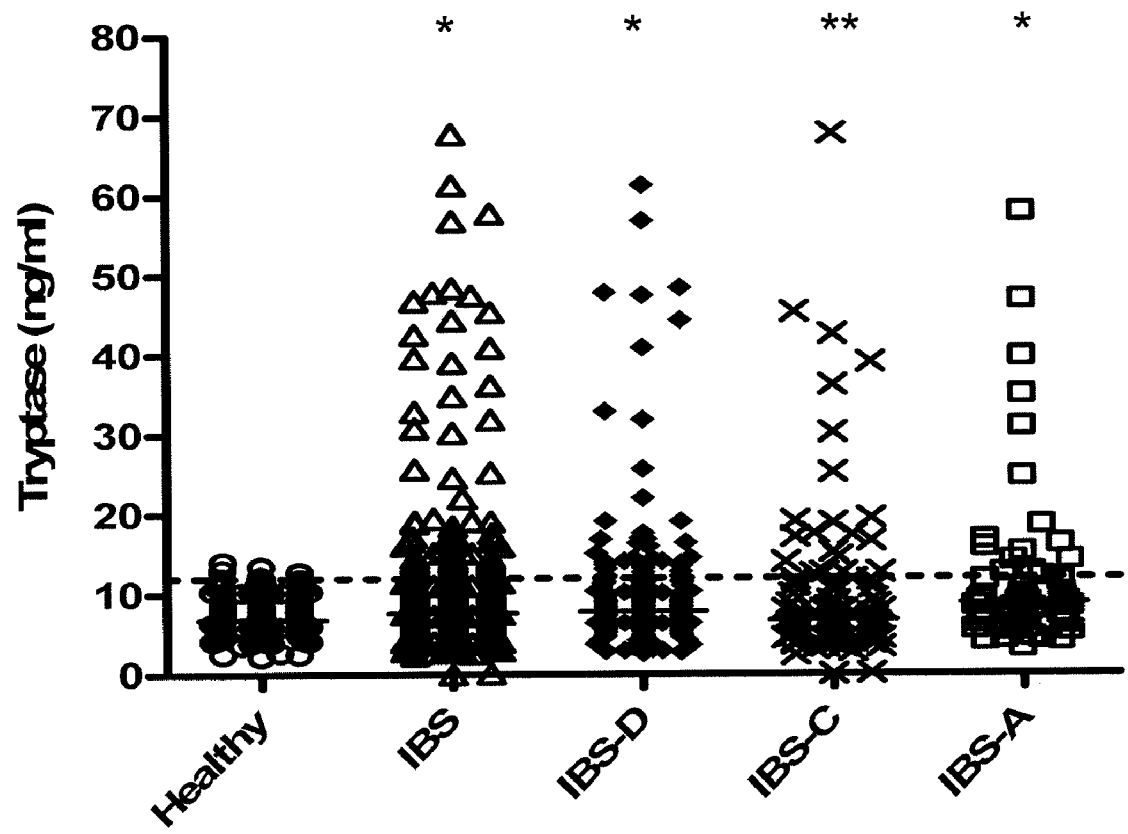
FIG. 10 illustrates tryptase levels in serum from healthy controls (n=139) and from subjects with IBS (n=378).

FIG. 9 shows the optimization of the tryptase ELISA described herein. FIG. 10 shows tryptase levels in serum from healthy controls (n=139) and from subjects with IBS (n=378). Tryptase levels were measured by ELISA in serum samples diluted 10 times with assay buffer. IBS patients are also shown according to its subtypes: IBS-D (n=206): diarrhea predominant; IBS-C (n=116): constipation predominant; IBS-A (n=56): alternating symptoms. Each value is the average of duplicate determinations. Solid lines are the median value from each group. The cutoff value of 12 ng/ml was calculated from healthy subjects with median plus 2SD (dotted line). *p<0.0001 vs healthy subjects; **p<0.0001 vs IBS-D; Mann Whitney U test. Table 2 provides a summary of tryptase levels in IBS Subtypes and healthy subjects (cutoff=12.0 ng/ml).

TABLE 2

Tryptase levels (ng/ml) in IBS Subtypes and healthy subjects (cutoff = 12.0 ng/ml).

|  | Healthy Control | IBS | IBS-D | IBS-C | IBS-A |
|---|---|---|---|---|---|
| Subjects (n) | 139 | 381 | 209 | 116 | 56 |
| Mean (ng/ml) | 7.1 | 10.3 | 10.3 | 9.6 | 12.1 |
| STDEV | 2.4 | 9.2 | 8.7 | 9.4 | 10.7 |
| Positive | 9 | 82 | 44 | 22 | 16 |

FIG. 11 shows the increased serum level of histamine and $PGE_2$ in IBS patients vs healthy controls. $PGE_2$ was measured in 50 µl of serum by ELISA using a kit from Cayman. Histamine was measured in 10 µl of serum using an Immunotech EIA kit. The samples were tested in duplicate. The solid line is the median of each group. As such, in certain aspects, IBS-D may be diagnosed or distinguished from other clinical subtypes of IBS by detecting a higher level of $PGE_2$ relative to healthy control, IBS-A, and/or IBS-C samples or standards. In certain other aspects, IBS-D or IBS-A may be diagnosed or distinguished from IBS-C by detecting a higher level of histamine relative to healthy control and/or IBS-C samples or standards.

Conclusions: (1) A sandwich ELISA method was developed that can measure serum tryptase level with high sensitivity, accuracy, and precision. The assay has a high degree of reproducibility and is suitable for routine testing of a large number of human sera. (2) Using this ELISA, we found significant differences in serum tryptase levels between healthy controls and IBS patients. Among the IBS patients, IBS-D and IBS-A patients had statistically higher tryptase levels compared to IBS-C patients. (3) Additional mast cell markers, histamine and $PGE_2$, were also found to be aberrant in IBS patient serum samples. Combining these markers with tryptase resulted in improved diagnostic accuracy of IBS.

C. Example 3

Questionnaire for Identifying the Presence or Severity of Symptoms Associated with IBS This example illustrates a questionnaire that is useful for identifying the presence or severity of one or more IBS-related symptoms in an individual. The questionnaire can be completed by the individual at the clinic or physician's office, or can be brought home and submitted when the individual returns to the clinic or physician's office, e.g., to have his or her blood drawn.

In some embodiments, the questionnaire comprises a first section containing a set of questions asking the individual to provide answers regarding the presence or severity of one or more symptoms associated with IBS. The questionnaire generally includes questions directed to identifying the presence, severity, frequency, and/or duration of IBS-related symptoms such as chest pain, chest discomfort, heartburn, uncomfortable fullness after having a regular-sized meal, inability to finish a regular-sized meal, abdominal pain, abdominal discomfort, constipation, diarrhea, bloating, and/or abdominal distension.

In certain instances, the first section of the questionnaire includes all or a subset of the questions from a questionnaire developed by the Rome Foundation Board based on the Rome III criteria, available at http://www.romecriteria.org/questionnaires/. For example, the questionnaire can include all or a subset of the 93 questions set forth on pages 920-936 of the Rome III Diagnostic Questionnaire for the Adult Functional GI Disorders (Appendix C), available at http://www.romecriteria.org/pdfs/AdultFunctGIQ.pdf. Preferably, the first section of the questionnaire contains 16 of the 93 questions set forth in the Rome III Diagnostic Questionnaire (see, Table 3). Alternatively, the first section of the questionnaire can contain a subset (e.g., 1, 2, 3, 4, 5, 6, 7, 8, 9, 10, 11, 12, 13, 14, or 15) of the 16 questions shown in Table 3. As a non-limiting example, the following 10 questions set forth in Table 3 can be included in the questionnaire: Question Nos. 2, 3, 5, 6, 9, 10, 11, 13, 15, and 16. One skilled in the art will appreciate that the first section of the questionnaire can comprise questions similar to the questions shown in Table 3 regarding pain, discomfort, and/or changes in stool consistency.

TABLE 3

Exemplary first section of a questionnaire for identifying the presence or severity of IBS-related symptoms.

1. In the last 3 months, how often did you have pain or discomfort in the middle of your chest (not related to heart problems)?
   - (0) Never
   - (1) Less than one day a month
   - (2) One day a month
   - (3) Two to three days a month
   - (4) One day a week
   - (5) More than one day a week
   - (6) Every day 2. In the last 3 months, how often did you have heartburn (a burning discomfort or burning pain in your chest)?
   - (0) Never
   - (1) Less than one day a month
   - (2) One day a month
   - (3) Two to three days a month
   - (4) One day a week
   - (5) More than one day a week
   - (6) Every day 3. In the last 3 months, how often did you feel uncomfortably full after a regular-sized meal?
   - (0) Never →
   - (1) Less than one day a month
   - (2) One day a month
   - (3) Two to three days a month
   - (4) One day a week
   - (5) More than one day a week
   - (6) Every day 4. In the last 3 months, how often were you unable to finish a regular size meal?
   - (0) Never →
   - (1) Less than one day a month
   - (2) One day a month
   - (3) Two to three days a month
   - (4) One day a week
   - (5) More than one day a week
   - (6) Every day 5. In the last 3 months, how often did you have pain or burning in the middle of your abdomen, above your belly button but not in your chest?
   - (0) Never →
   - (1) Less than one day a month
   - (2) One day a month
   - (3) Two to three days a month
   - (4) One day a week
   - (5) More than one day a week
   - (6) Every day 6. In the last 3 months, how often did you have discomfort or pain anywhere in your abdomen?
   - (0) Never →
   - (1) Less than one day a month
   - (2) One day a month
   - (3) Two to three days a month
   - (4) One day a week
   - (5) More than one day a week
   - (6) Every day 7. In the last 3 months, how often did you have fewer than three bowel movements (0-2) a week?
   - (0) Never or rarely
   - (1) Sometimes
   - (2) Often
   - (3) Most of the time
   - (4) Always TABLE 3-continued Exemplary first section of a questionnaire for identifying the presence or severity of IBS-related symptoms.

| | |
|---|---|
| 8. In the last 3 months, how often did you have hard or lumpy stools? | (0) Never or rarely<br>(1) Sometimes (25% of the time)<br>(2) Often (50% of the time)<br>(3) Most of the time (75% of the time)<br>(4) Always |
| 9. In the last 3 months, how often did you strain during bowel movements? | (0) Never or rarely<br>(1) Sometimes<br>(2) Often<br>(3) Most of the time<br>(4) Always |
| 10. In the last 3 months, how often did you have a feeling of incomplete emptying after bowel movements? | (0) Never or rarely<br>(1) Sometimes<br>(2) Often<br>(3) Most of the time<br>(4) Always |
| 11. In the last 3 months, how often did you have a sensation that the stool could not be passed, (i.e., blocked), when having a bowel movement? | (0) Never or rarely<br>(1) Sometimes<br>(2) Often<br>(3) Most of the time<br>(4) Always |
| 12. In the last 3 months, how often did you press on or around your bottom or remove stool in order to complete a bowel movement? | (0) Never or rarely<br>(1) Sometimes<br>(2) Often<br>(3) Most of the time<br>(4) Always |
| 13. Did any of the symptoms of constipation listed in questions 27-32 above begin more than 6 months ago? | (0) No<br>(1) Yes |
| 14. In the last 3 months, how often did you have loose, mushy or watery stools? | (0) Never or rarely →<br>(1) Sometimes (25% of the time)<br>(2) Often (50% of the time)<br>(3) Most of the time (75% of the time)<br>(4) Always |
| 15. In the last 3 months, how often did you have bloating or distension? | (0) Never →<br>(1) Less than one day a month<br>(2) One day a month<br>(3) Two to three days a month<br>(4) One day a week<br>(5) More than one day a week<br>(6) Every day |
| 16. Did your symptoms of bloating or distention begin more than 6 months ago? | (0) No<br>(1) Yes |

In other embodiments, the questionnaire comprises a second section containing a set of questions asking the individual to provide answers regarding the presence or severity of negative thoughts or feelings associated with having IBS-related pain or discomfort. For example, the questionnaire can include questions directed to identifying the presence, severity, frequency, and/or duration of anxiety, fear, nervousness, concern, apprehension, worry, stress, depression, hopelessness, despair, pessimism, doubt, and/or negativity when the individual is experiencing pain or discomfort associated with one or more symptoms of IBS.

In certain instances, the second section of the questionnaire includes all or a subset of the questions from a questionnaire described in Sullivan et al., The Pain Catastrophizing Scale: Development and Validation, *Psychol. Assess.*, 7:524-532 (1995). For example, the questionnaire can include a set of questions to be answered by an individual according to a Pain Catastrophizing Scale (PCS), which indicates the degree to which the individual has certain negative thoughts and feelings when experiencing pain: 0=not at all; 1=to a slight degree; 2=to a moderate degree; 3=to a great degree; 4=all the time. The second section of the questionnaire can contain 1, 2, 3, 4, 5, 6, 7, 8, 9, 10, 11, 12, 13, 14, 15, or more questions or statements related to identifying the presence or severity of negative thoughts or feelings associated with having IBS-related pain or discomfort. As a non-limiting example, an individual can be asked to rate the degree to which he or she has one or more of the following thoughts and feelings when experiencing pain: "I worry all the time about whether the pain will end"; "I feel I can't stand it anymore"; "I become afraid that the pain will get worse"; "I anxiously want the pain to go away"; and "I keep thinking about how much it hurts." One skilled in the art will understand that the questionnaire can comprise similar questions regarding negative thoughts or feelings associated with having IBS-related pain or discomfort.

In some embodiments, the questionnaire includes only questions from the first section of the questionnaire or a subset thereof (see, e.g., Table 3). In other embodiments, the questionnaire includes only questions from the second section of the questionnaire or a subset thereof.

Upon completion of the questionnaire by the individual, the numbers corresponding to the answers to each question can be summed and the resulting value can be combined with the analysis of one or more diagnostic markers in a sample from the individual and processed using the statistical algorithms described herein to increase the accuracy of predicting IBS.

Alternatively, a "Yes" or "No" answer from the individual to the following question: "Are you currently experiencing any symptoms?" can be combined with the analysis of one or more of the biomarkers described herein and processed using a single statistical algorithm or a combination of statistical algorithms to increase the accuracy of predicting IBS.

D. Example 4

Blood Based Diagnostic Assay for the Diagnosis of Irritable Bowel Syndrome (IBS)

The present example describes the first blood-based biomarker test for Irritable Bowel Syndrome (IBS). This test can aid clinicians in the diagnosis of IBS. The IBS Diagnostic described below was validated using well-characterized IBS samples collected from recognized IBS experts and GI clinics. The samples were either Rome II or Rome III positive and the patients had a diagnosis of IBS for greater than one year. The test has a sensitivity of 50%, specificity of 88% with an overall accuracy of 70%.

The total cohort used to develop the present assay consisted of 1,721 serum samples. The validation cohort used consisted of 516 serum samples, of which 50% were diagnosed with IBS according to Rome II or Rome III criteria; 36% were Non-IBS disease controls; and 14% were normal healthy controls. The sensitivity of the assay is 50% and the specificity is 88%. When ruling in IBS, wherein the physician has determined that there is about a 75% probability of disease in the patient, 94% of the positive test results are true positives, while 38% of the negative test results are true negatives. When ruling out IBS, wherein the physician has determined that there is about a 25% probability of disease in the patient, 86% of the negative test results are true negatives, while 61% of the positive test results are true positives.

The assay involves the quantitative analysis of bio-markers combined with a two learning statistical classifier system consisting of a random forest classifier and a neural network classifier.

The specimen requirements for the assay consist of the physician obtaining 2.0 ml of separated serum in, for example, an SST tube. For best results, the sample should be centrifuges and refrigerates within 2 hours of collection. When samples need to be shipped prior to assay detection, the samples should be refrigerated or frozen. For best results, the samples should be stored, prior to use, for no more than 7 days at 4° C. or 30 days if frozen.

Briefly, enzyme-linked immunosorbent assays (ELISAs) are performed with antibodies specific for the IBS biomarkers ASCA-IgA, CBir1, ANCA, and tTG. Additionally, chemiluminescent assays are performed for the IBS biomarkers BDNF, NGAL, TWEAK, GRO-α, IL-1β, and TIMP-1. Reference values for the normal range of these markers in healthy subjects are provided in Table 4.

TABLE 4

Reference values for the markers detected in the IBS assay.

| Marker | Reference Level |
| --- | --- |
| BDNF (Brain-Derived Neurotrophic Factor) | 7536.5-31324.4 pg/ml |
| NGAL (Neutrophil Gelatinase-Associated Lipocalin) | 28.3-272.5 ng/ml |
| TWEAK (TNF-related Weak Inducer of Apoptosis | 351.6-1751.7 pg/ml |
| GRO-α (Growth-Regulated Oncogene Alpha) | 26.4-499.3 pg/ml |
| IL-1β (Interleukin-1 Beta) | 279.5-1358.6 fg/ml |
| TIMP-1 (Tissue Inhibitor of Metalloproteinase-1) | 156.1-410.6 ng/ml |
| ASCA-IgA (Anti-*Saccharomyces cerevisiae* Anitbody) | <20.0 EU/ml |
| CBir1 (Anti-CBir1 Antibody) | <21.0 EU/ml |
| ANCA (Anti-Human Neutrophil Cytoplasmic Antibody) | <12.1 EU/ml |
| tTG (Anti-Human Tissue Transglutaminase IgA) | <4.0 U/ml |

In certain instances, information from the detection of the IBS biomarkers described above can be combined with symptom information provided by the patient. For example, the patient may fill out a checklist of their symptoms, the information from which can be combined with the information from the IBS biomarkers to further aid the clinician in the diagnosis of IBS. An example of a checklist that may be used in this fashion is provided in Table 5.

TABLE 5

Example patient checklist of symptoms commonly associated with IBS.
IBS Symptom Checklist Fill out and bring to your next appointment.
Your Name _____
Appointment Date _____
Place a check mark next to any symptoms you are currently having or have had in the past. Note how often these symptoms are present.
_____ Recurrent abdominal pain or discomfort
_____ Abnormal stool frequency (greater than 3 bowel movements/day or less than 3 bowel movements/week)
_____ Abnormal stool form (lumpy/hard or loose/watery stool)
_____ Abnormal stool passage (straining, urgency, or feeling of incomplete bowel movement)
_____ Passage of mucus
_____ Bloating or feeling of abdominal distension
_____ Gassiness
_____ Feelings of urgency (the need to find a restroom fast)

E. References

1. Barbara G and Cremon C. Serine proteases: new players in diarrhoea-predominant irritable bowel syndrome. Gut. 2008 May; 57(5):591-9.

2. Barbara G, Wang B, Stanghellini V, et al. Mast Cell-Dependent Excitation of Visceral-Nociceptive Sensory Neurons in Irritable Bowel Syndrome. Gastroenterology 2007; 132:26-37.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for aiding in the diagnosis of irritable bowel syndrome (IBS) in a subject, said method comprising:
    (a) contacting a blood or serum sample from the subject with a β-tryptase binding moiety under conditions suitable to transform β-tryptase present in the sample into a complex comprising β-tryptase and the β-tryptase binding moiety; and
    (b) determining the level of said complex, thereby determining the level of β-tryptase present in the sample.

2. The method of claim 1, wherein the method further comprises:
    (c) comparing the level of β-tryptase present in the sample to a control level, wherein a difference in the level of β-tryptase present in the sample relative to the control level is indicative of an increased likelihood of said subject having IBS.

3. The method of claim 2, wherein the control level is the level of β-tryptase present in a blood or serum sample from a healthy subject.

4. The method of claim 3, wherein an increased level of β-tryptase present in the sample relative to the control level is indicative of an increased likelihood of said subject having IBS.

5. The method of claim 3, wherein the same or a reduced level of β-tryptase present in the sample relative to the control level is indicative of an increased likelihood of said subject not having IBS.

6. The method of claim 2, wherein the control level is the level of β-tryptase present in a blood or serum sample from a subject with IBS.

7. The method of claim 6, wherein the same or an increased level of β-tryptase present in the sample relative to the control level is indicative of an increased likelihood of said subject having IBS.

8. The method of claim 6, wherein a reduced level of β-tryptase present in the sample relative to the control level is indicative of an increased likelihood of said subject not having IBS.

9. The method of claim 1, wherein the method further comprises determining the level of histamine and/or prostaglandin $E_2$ ($PGE_2$) present in the sample.

10. A method for monitoring the progression or regression of irritable bowel syndrome (IBS) in a subject, the method comprising:
    (a) contacting a first blood or serum sample taken from the subject at a first time with a β-tryptase binding moiety under conditions suitable to transform β-tryptase present in the sample into a complex comprising β-tryptase and the β-tryptase binding moiety;
    (b) determining the level of said complex, thereby determining the level of β-tryptase present in the first sample;
    (c) contacting a second blood or serum sample taken from the subject at a second time with a β-tryptase binding moiety under conditions suitable to transform β-tryptase present in the sample into a complex comprising β-tryptase and the β-tryptase binding moiety;
(d) determining the level of said complex, thereby determining the level of β-tryptase present in the second sample; and
(e) comparing the level of β-tryptase present in the first sample to the level of β-tryptase present in the second sample, wherein a higher level of β-tryptase in the second sample relative to the first sample is indicative of the progression of IBS in the subject and a lower level of β-tryptase in the second sample relative to the first sample is indicative of the regression of IBS in the subject.

\* \* \* \* \*